United States Patent
Gani et al.

(10) Patent No.: US 11,890,462 B2
(45) Date of Patent: *Feb. 6, 2024

(54) STIMULATION SYSTEMS AND RELATED USER INTERFACES

(71) Applicant: Lungpacer Medical Inc., Vancouver (CA)

(72) Inventors: Matthew J. Gani, Seattle, WA (US); Kaitlin Taylor, Exton, PA (US); Viral S Thakkar, Chester Springs, PA (US); Douglas G. Evans, Downingtown, PA (US)

(73) Assignee: Lungpacer Medical Inc., Vancouver (CA)

( * ) Notice: Subject to any disclaimer, the term of this patent is extended or adjusted under 35 U.S.C. 154(b) by 879 days.

This patent is subject to a terminal disclaimer.

(21) Appl. No.: 16/677,794

(22) Filed: Nov. 8, 2019

(65) Prior Publication Data
US 2020/0147364 A1 May 14, 2020

Related U.S. Application Data

(60) Provisional application No. 62/757,576, filed on Nov. 8, 2018.

(51) Int. Cl.
*A61N 1/36* (2006.01)
*A61N 1/05* (2006.01)
(Continued)

(52) U.S. Cl.
CPC .............. *A61N 1/05* (2013.01); *A61M 25/00* (2013.01); *A61N 1/3601* (2013.01); *A61N 1/365* (2013.01);
(Continued)

(58) Field of Classification Search
CPC ... A61N 1/36135; A61N 1/365; A61N 1/0476
See application file for complete search history.

(56) References Cited

U.S. PATENT DOCUMENTS 1,693,734 A 12/1928 Waggoner
2,532,788 A 12/1950 Sarnoff
(Continued)

FOREIGN PATENT DOCUMENTS

CN 1652839 A 8/2005
CN 102143781 A 8/2011
(Continued)

OTHER PUBLICATIONS

International Search Report issued in corresponding International Application No. PCT/US2019/060268 dated Mar. 5, 2020 (2 pages).
(Continued)

*Primary Examiner* — Alyssa M Alter
(74) *Attorney, Agent, or Firm* — Bookoff McAndrews, PLLC

(57) ABSTRACT

A system for stimulating body tissue may include a user interface and a control unit. The control unit may include a processor and non-transitory computer readable medium. The non-transitory computer readable medium may store instructions that, when executed by the processor, causes the processor to identify an electrode combination and determine a threshold charge for use in stimulating the body tissue. The processors identifications and determinations may be based at least partially on input received via the user interface.

20 Claims, 9 Drawing Sheets

(51) Int. Cl.
*G06F 9/54* (2006.01)
*A61M 25/00* (2006.01)
*A61N 1/372* (2006.01)
*A61N 1/365* (2006.01)

(52) U.S. Cl.
CPC ..... *A61N 1/36135* (2013.01); *A61N 1/37247* (2013.01); *G06F 9/542* (2013.01)

(56) References Cited

U.S. PATENT DOCUMENTS

| | | |
|---|---|---|
| 2,664,880 A | 1/1954 | Wales, Jr. |
| 3,348,548 A | 10/1967 | Chardack |
| 3,470,876 A | 10/1969 | John |
| 3,769,984 A | 11/1973 | Muench |
| 3,804,098 A | 4/1974 | Friedman |
| 3,817,241 A | 6/1974 | Grausz |
| 3,835,864 A | 9/1974 | Rasor et al. |
| 3,847,157 A | 11/1974 | Caillouette et al. |
| 3,851,641 A | 12/1974 | Toole et al. |
| 3,896,373 A | 7/1975 | Zelby |
| 3,938,502 A | 2/1976 | Bom |
| 3,983,881 A | 10/1976 | Wickham |
| 4,054,881 A | 10/1977 | Raab |
| 4,072,146 A | 2/1978 | Howes |
| 4,114,601 A | 9/1978 | Abels |
| 4,173,228 A | 11/1979 | Childress et al. |
| 4,249,539 A | 2/1981 | Mezrich et al. |
| 4,317,078 A | 2/1982 | Weed et al. |
| 4,380,237 A | 4/1983 | Newbower |
| 4,407,294 A | 10/1983 | Vilkomerson |
| 4,416,289 A | 11/1983 | Bresler |
| 4,431,005 A | 2/1984 | Mccormick |
| 4,431,006 A | 2/1984 | Trimmer et al. |
| 4,445,501 A | 5/1984 | Bresler |
| RE31,873 E | 4/1985 | Howes |
| 4,573,481 A | 3/1986 | Bullara |
| 4,586,923 A | 5/1986 | Gould et al. |
| 4,587,975 A | 5/1986 | Salo et al. |
| 4,643,201 A | 2/1987 | Stokes |
| 4,674,518 A | 6/1987 | Salo |
| 4,681,117 A | 7/1987 | Brodman et al. |
| 4,683,890 A | 8/1987 | Hewson |
| 4,697,595 A | 10/1987 | Breyer et al. |
| 4,706,681 A | 11/1987 | Breyer et al. |
| 4,771,788 A | 9/1988 | Millar |
| 4,819,662 A | 4/1989 | Heil, Jr. et al. |
| 4,827,935 A | 5/1989 | Geddes et al. |
| 4,830,008 A | 5/1989 | Meer |
| 4,840,182 A | 6/1989 | Carlson |
| 4,852,580 A | 8/1989 | Wood |
| 4,860,769 A | 8/1989 | Fogarty et al. |
| 4,905,698 A | 3/1990 | Strohl, Jr. et al. |
| 4,911,174 A | 3/1990 | Pederson et al. |
| 4,934,049 A | 6/1990 | Kiekhafer et al. |
| 4,944,088 A | 7/1990 | Doan et al. |
| 4,951,682 A | 8/1990 | Petre |
| 4,957,110 A | 9/1990 | Vogel et al. |
| 4,989,617 A | 2/1991 | Memberg et al. |
| 5,005,587 A | 4/1991 | Scott |
| 5,036,848 A | 8/1991 | Hewson |
| 5,042,143 A | 8/1991 | Holleman et al. |
| 5,056,519 A | 10/1991 | Vince |
| 5,115,818 A | 5/1992 | Holleman et al. |
| 5,146,918 A | 9/1992 | Kallok et al. |
| 5,170,802 A | 12/1992 | Mehra |
| 5,184,621 A | 2/1993 | Vogel et al. |
| 5,224,491 A | 7/1993 | Mehra |
| 5,243,995 A | 9/1993 | Maier |
| 5,265,604 A | 11/1993 | Vince |
| 5,267,569 A | 12/1993 | Lienhard |
| 5,314,463 A | 5/1994 | Camps et al. |
| 5,316,009 A | 5/1994 | Yamada |
| 5,324,322 A | 6/1994 | Grill, Jr. et al. |
| 5,330,522 A | 7/1994 | Kreyenhagen |
| 5,345,936 A | 9/1994 | Pomeranz et al. |
| 5,383,923 A | 1/1995 | Webster, Jr. |
| 5,411,025 A | 5/1995 | Webster, Jr. |
| 5,417,208 A | 5/1995 | Winkler |
| 5,451,206 A | 9/1995 | Young |
| 5,456,254 A | 10/1995 | Pietroski et al. |
| 5,465,717 A | 11/1995 | Imran et al. |
| 5,476,498 A | 12/1995 | Ayers |
| 5,486,159 A | 1/1996 | Mahurkar |
| 5,507,725 A | 4/1996 | Savage et al. |
| 5,524,632 A | 6/1996 | Stein et al. |
| 5,527,358 A | 6/1996 | Mehmanesh et al. |
| 5,531,686 A | 7/1996 | Lundquist et al. |
| 5,549,655 A | 8/1996 | Erickson |
| 5,555,618 A | 9/1996 | Winkler |
| 5,567,724 A | 10/1996 | Kelleher et al. |
| 5,584,873 A | 12/1996 | Shoberg et al. |
| 5,604,231 A | 2/1997 | Smith et al. |
| 5,665,103 A | 9/1997 | Lafontaine et al. |
| 5,678,535 A | 10/1997 | Dimarco |
| 5,683,370 A | 11/1997 | Luther et al. |
| 5,709,853 A | 1/1998 | Iino et al. |
| 5,716,392 A | 2/1998 | Bourgeois et al. |
| 5,733,255 A | 3/1998 | Dinh et al. |
| 5,755,765 A | 5/1998 | Hyde et al. |
| 5,776,111 A | 7/1998 | Tesio |
| 5,779,732 A | 7/1998 | Amundson |
| 5,782,828 A | 7/1998 | Chen et al. |
| 5,785,706 A | 7/1998 | Bednarek |
| 5,788,681 A | 8/1998 | Weaver et al. |
| 5,813,399 A | 9/1998 | Isaza et al. |
| 5,814,086 A | 9/1998 | Hirschberg et al. |
| RE35,924 E | 10/1998 | Winkler |
| 5,824,027 A | 10/1998 | Hoffer et al. |
| 5,827,192 A | 10/1998 | Gopakumaran et al. |
| 5,916,163 A | 6/1999 | Panescu et al. |
| 5,944,022 A | 8/1999 | Nardella et al. |
| 5,954,761 A | 9/1999 | Machek et al. |
| 5,967,978 A | 10/1999 | Littmann et al. |
| 5,971,933 A | 10/1999 | Gopakumaran et al. |
| 5,983,126 A | 11/1999 | Wittkampf |
| 6,006,134 A | 12/1999 | Hill et al. |
| 6,024,702 A | 2/2000 | Iversen |
| 6,096,728 A | 8/2000 | Collins et al. |
| 6,120,476 A | 9/2000 | Fung et al. |
| 6,123,699 A | 9/2000 | Webster, Jr. |
| 6,126,649 A | 10/2000 | Vantassel et al. |
| 6,136,021 A | 10/2000 | Tockman et al. |
| 6,157,862 A | 12/2000 | Brownlee et al. |
| 6,161,029 A | 12/2000 | Spreigl et al. |
| 6,166,048 A | 12/2000 | Bencherif |
| 6,171,277 B1 | 1/2001 | Ponzi |
| 6,183,463 B1 | 2/2001 | Webster, Jr. |
| 6,198,970 B1 | 3/2001 | Freed et al. |
| 6,198,974 B1 | 3/2001 | Webster, Jr. |
| 6,201,994 B1 | 3/2001 | Warman et al. |
| 6,208,881 B1 | 3/2001 | Champeau |
| 6,210,339 B1 | 4/2001 | Kiepen et al. |
| 6,212,435 B1 | 4/2001 | Lattner et al. |
| 6,216,045 B1 | 4/2001 | Black et al. |
| 6,236,892 B1 | 5/2001 | Feler |
| 6,240,320 B1 | 5/2001 | Spehr et al. |
| 6,249,708 B1 | 6/2001 | Nelson et al. |
| 6,251,126 B1 | 6/2001 | Ottenhoff et al. |
| 6,269,269 B1 | 7/2001 | Ottenhoff et al. |
| 6,292,695 B1 | 9/2001 | Webster, Jr. et al. |
| 6,295,475 B1 | 9/2001 | Morgan |
| 6,360,740 B1 | 3/2002 | Ward et al. |
| 6,397,108 B1 | 5/2002 | Camps et al. |
| 6,400,976 B1 | 6/2002 | Champeau |
| 6,415,183 B1 | 7/2002 | Scheiner et al. |
| 6,415,187 B1 | 7/2002 | Kuzma et al. |
| 6,438,427 B1 | 8/2002 | Rexhausen et al. |
| 6,445,953 B1 | 9/2002 | Bulkes et al. |
| 6,449,507 B1 | 9/2002 | Hill et al. |
| 6,463,327 B1 | 10/2002 | Lurie et al. |
| 6,493,590 B1 | 12/2002 | Wessman et al. |
| 6,508,802 B1 | 1/2003 | Rosengart et al. |
| 6,526,321 B1 | 2/2003 | Spehr |

(56) References Cited

U.S. PATENT DOCUMENTS

| | | |
|---|---|---|
| 6,569,114 B2 | 5/2003 | Ponzi et al. |
| 6,584,362 B1 | 6/2003 | Scheiner et al. |
| 6,585,718 B2 | 7/2003 | Hayzelden et al. |
| 6,587,726 B2 | 7/2003 | Lurie et al. |
| 6,602,242 B1 | 8/2003 | Fung et al. |
| 6,610,713 B2 | 8/2003 | Tracey |
| 6,630,611 B1 | 10/2003 | Malowaniec |
| 6,643,552 B2 | 11/2003 | Edell et al. |
| 6,651,652 B1 | 11/2003 | Waard |
| 6,682,526 B1 | 1/2004 | Jones et al. |
| 6,702,780 B1 | 3/2004 | Gilboa et al. |
| 6,718,208 B2 | 4/2004 | Hill et al. |
| 6,721,603 B2 | 4/2004 | Zabara et al. |
| 6,757,970 B1 | 7/2004 | Kuzma et al. |
| 6,778,854 B2 | 8/2004 | Puskas |
| 6,779,257 B2 | 8/2004 | Kiepen et al. |
| 6,844,713 B2 | 1/2005 | Steber et al. |
| RE38,705 E | 2/2005 | Hill et al. |
| 6,881,211 B2 | 4/2005 | Schweikert et al. |
| 6,885,888 B2 | 4/2005 | Rezai |
| 6,907,285 B2 | 6/2005 | Denker et al. |
| 6,934,583 B2 | 8/2005 | Weinberg et al. |
| 6,981,314 B2 | 1/2006 | Black et al. |
| 6,999,820 B2 | 2/2006 | Jordan |
| 7,018,374 B2 | 3/2006 | Schon et al. |
| 7,047,627 B2 | 5/2006 | Black et al. |
| 7,071,194 B2 | 7/2006 | Teng |
| 7,072,720 B2 | 7/2006 | Puskas |
| 7,077,823 B2 | 7/2006 | Mcdaniel |
| 7,082,331 B1 | 7/2006 | Park et al. |
| 7,130,700 B2 | 10/2006 | Gardeski et al. |
| 7,142,903 B2 | 11/2006 | Rodriguez et al. |
| 7,149,585 B2 | 12/2006 | Wessman et al. |
| 7,155,278 B2 | 12/2006 | King et al. |
| 7,167,751 B1 | 1/2007 | Whitehurst et al. |
| 7,168,429 B2 | 1/2007 | Matthews et al. |
| 7,184,829 B2 | 2/2007 | Hill et al. |
| 7,206,636 B1 | 4/2007 | Turcott |
| 7,212,867 B2 | 5/2007 | Van et al. |
| 7,225,016 B1 | 5/2007 | Koh |
| 7,225,019 B2 | 5/2007 | Jahns et al. |
| 7,229,429 B2 | 6/2007 | Martin et al. |
| 7,231,260 B2 | 6/2007 | Wallace et al. |
| 7,235,070 B2 | 6/2007 | Vanney |
| 7,269,459 B1 | 9/2007 | Koh |
| 7,277,757 B2 | 10/2007 | Casavant et al. |
| 7,283,875 B2 | 10/2007 | Larsson et al. |
| 7,340,302 B1 | 3/2008 | Falkenberg et al. |
| 7,363,085 B1 | 4/2008 | Benser et al. |
| 7,363,086 B1 | 4/2008 | Koh et al. |
| 7,371,220 B1 | 5/2008 | Koh et al. |
| 7,416,552 B2 | 8/2008 | Paul et al. |
| 7,421,296 B1 | 9/2008 | Benser et al. |
| 7,454,244 B2 | 11/2008 | Kassab et al. |
| 7,519,425 B2 | 4/2009 | Benser et al. |
| 7,519,426 B1 | 4/2009 | Koh et al. |
| 7,522,953 B2 | 4/2009 | Gharib et al. |
| 7,553,305 B2 | 6/2009 | Honebrink et al. |
| 7,555,349 B2 | 6/2009 | Wessman et al. |
| 7,569,029 B2 | 8/2009 | Clark et al. |
| 7,591,265 B2 | 9/2009 | Lee et al. |
| 7,593,760 B2 | 9/2009 | Rodriguez et al. |
| 7,613,524 B2 | 11/2009 | Jordan |
| 7,636,600 B1 | 12/2009 | Koh |
| 7,670,284 B2 | 3/2010 | Padget et al. |
| 7,672,728 B2 | 3/2010 | Libbus et al. |
| 7,672,729 B2 | 3/2010 | Koh et al. |
| 7,676,275 B1 | 3/2010 | Farazi et al. |
| 7,676,910 B2 | 3/2010 | Kiepen et al. |
| 7,697,984 B2 | 4/2010 | Hill et al. |
| 7,747,323 B2 | 6/2010 | Libbus et al. |
| 7,771,388 B2 | 8/2010 | Olsen et al. |
| 7,783,362 B2 | 8/2010 | Whitehurst et al. |
| 7,794,407 B2 | 9/2010 | Rothenberg |
| 7,797,050 B2 | 9/2010 | Libbus et al. |
| 7,813,805 B1 | 10/2010 | Farazi |
| 7,819,883 B2 | 10/2010 | Westlund et al. |
| 7,840,270 B2 | 11/2010 | Ignagni et al. |
| 7,853,302 B2 | 12/2010 | Rodriguez et al. |
| 7,869,865 B2 | 1/2011 | Govari et al. |
| 7,891,085 B1 | 2/2011 | Kuzma et al. |
| 7,925,352 B2 | 4/2011 | Stack et al. |
| 7,949,409 B2 | 5/2011 | Bly et al. |
| 7,949,412 B1 | 5/2011 | Harrison et al. |
| 7,962,215 B2 | 6/2011 | Ignagni et al. |
| 7,970,475 B2 | 6/2011 | Tehrani et al. |
| 7,972,323 B1 | 7/2011 | Bencini et al. |
| 7,974,693 B2 | 7/2011 | David et al. |
| 7,974,705 B2 | 7/2011 | Zdeblick et al. |
| 7,979,128 B2 | 7/2011 | Tehrani et al. |
| 7,994,655 B2 | 8/2011 | Bauer et al. |
| 8,000,765 B2 | 8/2011 | Rodriguez et al. |
| 8,019,439 B2 | 9/2011 | Kuzma et al. |
| 8,021,327 B2 | 9/2011 | Selkee |
| 8,036,750 B2 | 10/2011 | Caparso et al. |
| 8,050,765 B2 | 11/2011 | Lee et al. |
| 8,052,607 B2 | 11/2011 | Byrd |
| 8,104,470 B2 | 1/2012 | Lee et al. |
| 8,116,872 B2 | 2/2012 | Tehrani et al. |
| 8,121,692 B2 | 2/2012 | Haefner et al. |
| 8,135,471 B2 | 3/2012 | Zhang et al. |
| 8,140,164 B2 | 3/2012 | Tehrani et al. |
| 8,147,486 B2 | 4/2012 | Honour et al. |
| 8,160,701 B2 | 4/2012 | Zhao et al. |
| 8,160,711 B2 | 4/2012 | Tehrani et al. |
| 8,195,297 B2 | 6/2012 | Penner |
| 8,200,336 B2 | 6/2012 | Tehrani et al. |
| 8,206,343 B2 | 6/2012 | Racz |
| 8,224,456 B2 | 7/2012 | Daglow et al. |
| 8,233,987 B2 | 7/2012 | Gelfand et al. |
| 8,233,993 B2 | 7/2012 | Jordan |
| 8,239,037 B2 | 8/2012 | Glenn et al. |
| 8,244,358 B2 | 8/2012 | Tehrani et al. |
| 8,244,359 B2 | 8/2012 | Gelfand et al. |
| 8,244,378 B2 | 8/2012 | Bly et al. |
| 8,255,056 B2 | 8/2012 | Tehrani |
| 8,256,419 B2 | 9/2012 | Sinderby et al. |
| 8,265,736 B2 | 9/2012 | Sathaye et al. |
| 8,265,759 B2 | 9/2012 | Tehrani et al. |
| 8,275,440 B2 | 9/2012 | Rodriguez et al. |
| 8,280,513 B2 | 10/2012 | Tehrani et al. |
| 8,315,713 B2 | 11/2012 | Burnes et al. |
| 8,321,808 B2 | 11/2012 | Goetz et al. |
| 8,335,567 B2 | 12/2012 | Tehrani et al. |
| 8,340,783 B2 | 12/2012 | Sommer et al. |
| 8,348,941 B2 | 1/2013 | Tehrani |
| 8,369,954 B2 | 2/2013 | Stack et al. |
| 8,374,704 B2 | 2/2013 | Desai et al. |
| 8,388,541 B2 | 3/2013 | Messerly et al. |
| 8,388,546 B2 | 3/2013 | Rothenberg |
| 8,391,956 B2 | 3/2013 | Zellers et al. |
| 8,401,640 B2 | 3/2013 | Zhao et al. |
| 8,401,651 B2 | 3/2013 | Caparso et al. |
| 8,406,883 B1 | 3/2013 | Barker |
| 8,406,885 B2 | 3/2013 | Ignagni et al. |
| 8,412,331 B2 | 4/2013 | Tehrani et al. |
| 8,412,350 B2 | 4/2013 | Bly |
| 8,428,711 B2 | 4/2013 | Lin et al. |
| 8,428,726 B2 | 4/2013 | Ignagni et al. |
| 8,428,730 B2 | 4/2013 | Stack et al. |
| 8,433,412 B1 | 4/2013 | Westlund et al. |
| 8,442,638 B2 | 5/2013 | Libbus et al. |
| 8,457,764 B2 | 6/2013 | Ramachandran et al. |
| 8,467,876 B2 | 6/2013 | Tehrani |
| 8,473,068 B2 | 6/2013 | Farazi |
| 8,478,412 B2 | 7/2013 | Ignagni et al. |
| 8,478,413 B2 | 7/2013 | Karamanoglu et al. |
| 8,478,426 B2 | 7/2013 | Barker |
| 8,483,834 B2 | 7/2013 | Lee et al. |
| 8,504,158 B2 | 8/2013 | Karamanoglu et al. |
| 8,504,161 B1 | 8/2013 | Kornet et al. |
| 8,509,901 B2 | 8/2013 | Tehrani |
| 8,509,902 B2 | 8/2013 | Cho et al. |
| 8,509,919 B2 | 8/2013 | Yoo et al. |

(56) References Cited

U.S. PATENT DOCUMENTS

| | | |
|---|---|---|
| 8,512,256 B2 | 8/2013 | Rothenberg |
| 8,522,779 B2 | 9/2013 | Lee et al. |
| 8,527,036 B2 | 9/2013 | Jalde et al. |
| 8,532,793 B2 | 9/2013 | Morris et al. |
| 8,554,323 B2 | 10/2013 | Haefner et al. |
| 8,560,072 B2 | 10/2013 | Caparso et al. |
| 8,560,086 B2 | 10/2013 | Just et al. |
| 8,571,662 B2 | 10/2013 | Hoffer |
| 8,571,685 B2 | 10/2013 | Daglow et al. |
| 8,615,297 B2 | 12/2013 | Sathaye et al. |
| 8,617,228 B2 | 12/2013 | Wittenberger et al. |
| 8,620,412 B2 | 12/2013 | Griffiths et al. |
| 8,620,450 B2 | 12/2013 | Tockman et al. |
| 8,626,292 B2 | 1/2014 | Mccabe et al. |
| 8,630,707 B2 | 1/2014 | Zhao et al. |
| 8,644,939 B2 | 2/2014 | Wilson et al. |
| 8,644,952 B2 | 2/2014 | Desai et al. |
| 8,646,172 B2 | 2/2014 | Kuzma et al. |
| 8,650,747 B2 | 2/2014 | Kuzma et al. |
| 8,676,323 B2 | 3/2014 | Ignagni et al. |
| 8,676,344 B2 | 3/2014 | Desai et al. |
| 8,694,123 B2 | 4/2014 | Wahlstrand et al. |
| 8,696,656 B2 | 4/2014 | Abboud et al. |
| 8,706,223 B2 | 4/2014 | Zhou et al. |
| 8,706,235 B2 | 4/2014 | Karamanoglu et al. |
| 8,706,236 B2 | 4/2014 | Ignagni et al. |
| 8,718,763 B2 | 5/2014 | Zhou et al. |
| 8,725,259 B2 | 5/2014 | Kornet et al. |
| 8,738,154 B2 | 5/2014 | Zdeblick et al. |
| 8,755,889 B2 | 6/2014 | Scheiner |
| 8,774,907 B2 | 7/2014 | Rothenberg |
| 8,781,578 B2 | 7/2014 | Mccabe et al. |
| 8,781,582 B2 | 7/2014 | Ziegler et al. |
| 8,781,583 B2 | 7/2014 | Cornelussen et al. |
| 8,801,693 B2 | 8/2014 | He et al. |
| 8,805,511 B2 | 8/2014 | Karamanoglu et al. |
| 8,838,245 B2 | 9/2014 | Lin et al. |
| 8,858,455 B2 | 10/2014 | Rothenberg |
| 8,863,742 B2 | 10/2014 | Blomquist et al. |
| 8,886,277 B2 | 11/2014 | Kim et al. |
| 8,886,322 B2 | 11/2014 | Meadows et al. |
| 8,897,879 B2 | 11/2014 | Karamanoglu et al. |
| 8,903,507 B2 | 12/2014 | Desai et al. |
| 8,903,509 B2 | 12/2014 | Tockman et al. |
| 8,909,341 B2 | 12/2014 | Gelfand et al. |
| 8,914,113 B2 | 12/2014 | Zhang et al. |
| 8,918,169 B2 | 12/2014 | Kassab et al. |
| 8,918,987 B2 | 12/2014 | Kuzma et al. |
| 8,923,971 B2 | 12/2014 | Haefner et al. |
| 8,942,823 B2 | 1/2015 | Desai et al. |
| 8,942,824 B2 | 1/2015 | Yoo et al. |
| 8,948,884 B2 | 2/2015 | Ramachandran et al. |
| 8,968,299 B2 | 3/2015 | Kauphusman et al. |
| 8,972,015 B2 | 3/2015 | Stack et al. |
| 8,983,602 B2 | 3/2015 | Sathaye et al. |
| 9,008,775 B2 | 4/2015 | Sathaye et al. |
| 9,026,231 B2 | 5/2015 | Hoffer |
| 9,037,264 B2 | 5/2015 | Just et al. |
| 9,042,981 B2 | 5/2015 | Yoo et al. |
| 9,072,864 B2 | 7/2015 | Putz |
| 9,072,899 B1 | 7/2015 | Nickloes |
| 9,108,058 B2 | 8/2015 | Hoffer |
| 9,108,059 B2 | 8/2015 | Hoffer |
| 9,125,578 B2 | 9/2015 | Grunwald |
| 9,138,580 B2 | 9/2015 | Ignagni et al. |
| 9,138,585 B2 | 9/2015 | Saha et al. |
| 9,144,680 B2 | 9/2015 | Kaula et al. |
| 9,149,642 B2 | 10/2015 | Mccabe et al. |
| 9,168,377 B2 | 10/2015 | Hoffer |
| 9,174,046 B2 | 11/2015 | Francois et al. |
| 9,205,258 B2 | 12/2015 | Simon et al. |
| 9,216,291 B2 | 12/2015 | Lee et al. |
| 9,220,898 B2 | 12/2015 | Hoffer |
| 9,226,688 B2 | 1/2016 | Jacobsen et al. |
| 9,226,689 B2 | 1/2016 | Jacobsen et al. |
| 9,242,088 B2 | 1/2016 | Thakkar et al. |
| 9,259,573 B2 | 2/2016 | Tehrani et al. |
| 9,295,846 B2 | 3/2016 | Westlund et al. |
| 9,314,618 B2 | 4/2016 | Imran et al. |
| 9,333,363 B2 | 5/2016 | Hoffer et al. |
| 9,345,422 B2 | 5/2016 | Rothenberg |
| 9,370,657 B2 | 6/2016 | Tehrani et al. |
| 9,398,931 B2 | 7/2016 | Wittenberger et al. |
| 9,415,188 B2 | 8/2016 | He et al. |
| 9,427,566 B2 | 8/2016 | Reed et al. |
| 9,427,588 B2 | 8/2016 | Sathaye et al. |
| 9,474,894 B2 | 10/2016 | Mercanzini et al. |
| 9,485,873 B2 | 11/2016 | Shah et al. |
| 9,498,625 B2 | 11/2016 | Bauer et al. |
| 9,498,631 B2 | 11/2016 | Demmer et al. |
| 9,504,837 B2 | 11/2016 | Demmer et al. |
| 9,532,724 B2 | 1/2017 | Grunwald et al. |
| 9,533,160 B2 | 1/2017 | Brooke et al. |
| 9,539,429 B2 | 1/2017 | Brooke et al. |
| 9,545,511 B2 | 1/2017 | Thakkar et al. |
| 9,561,369 B2 | 2/2017 | Burnes et al. |
| 9,566,436 B2 | 2/2017 | Hoffer et al. |
| 9,572,982 B2 | 2/2017 | Burnes et al. |
| 9,597,509 B2 | 3/2017 | Hoffer et al. |
| 9,615,759 B2 | 4/2017 | Hurezan et al. |
| 9,623,239 B2 | 4/2017 | Francois et al. |
| 9,623,252 B2 | 4/2017 | Sathaye et al. |
| 9,662,494 B2 | 5/2017 | Young et al. |
| 9,682,235 B1 | 6/2017 | O'Mahony et al. |
| 9,694,185 B2 | 7/2017 | Bauer |
| 9,717,899 B2 | 8/2017 | Kuzma et al. |
| 9,724,018 B2 | 8/2017 | Cho et al. |
| 9,744,351 B1 | 8/2017 | Gelfand et al. |
| 9,776,005 B2 | 10/2017 | Meyyappan et al. |
| 9,861,817 B2 | 1/2018 | Cho et al. |
| 9,872,989 B2 | 1/2018 | Jung et al. |
| 9,884,178 B2 | 2/2018 | Bouton et al. |
| 9,884,179 B2 | 2/2018 | Bouton et al. |
| 9,919,149 B2 | 3/2018 | Imran et al. |
| 9,931,504 B2 | 4/2018 | Thakkar et al. |
| 9,950,167 B2 | 4/2018 | Hoffer et al. |
| 9,956,132 B2 | 5/2018 | Francois et al. |
| 9,956,396 B2 | 5/2018 | Young et al. |
| 9,968,785 B2 | 5/2018 | Hoffer et al. |
| 9,968,786 B2 | 5/2018 | Bauer et al. |
| 10,022,546 B2 | 7/2018 | Hoffer et al. |
| 10,035,017 B2 | 7/2018 | Thakkar et al. |
| 10,039,920 B1 | 8/2018 | Thakkar et al. |
| 10,195,429 B1 | 2/2019 | Thakkar et al. |
| 10,293,164 B2 | 5/2019 | Nash et al. |
| 10,369,361 B2 | 8/2019 | Bauer et al. |
| 10,391,314 B2 | 8/2019 | Hoffer et al. |
| 10,406,367 B2 | 9/2019 | Meyyappan |
| 10,413,203 B2 | 9/2019 | Saha et al. |
| 10,448,995 B2 | 10/2019 | Olson |
| 10,987,511 B2 * | 4/2021 | Gani .................. A61N 1/3611 |
| 2001/0052345 A1 | 12/2001 | Niazi |
| 2002/0026228 A1 | 2/2002 | Schauerte |
| 2002/0056454 A1 | 5/2002 | Samzelius |
| 2002/0065544 A1 | 5/2002 | Smits et al. |
| 2002/0087156 A1 | 7/2002 | Maguire et al. |
| 2002/0128546 A1 | 9/2002 | Silver |
| 2002/0188325 A1 | 12/2002 | Hill et al. |
| 2003/0078623 A1 | 4/2003 | Weinberg et al. |
| 2003/0195571 A1 | 10/2003 | Burnes et al. |
| 2004/0003813 A1 | 1/2004 | Banner et al. |
| 2004/0010303 A1 | 1/2004 | Bolea et al. |
| 2004/0030362 A1 | 2/2004 | Hill et al. |
| 2004/0044377 A1 | 3/2004 | Larsson et al. |
| 2004/0064069 A1 | 4/2004 | Reynolds et al. |
| 2004/0077936 A1 | 4/2004 | Larsson et al. |
| 2004/0088015 A1 | 5/2004 | Casavant et al. |
| 2004/0111139 A1 | 6/2004 | Mccreery |
| 2004/0186543 A1 | 9/2004 | King et al. |
| 2004/0210261 A1 | 10/2004 | King et al. |
| 2005/0004565 A1 | 1/2005 | Vanney |
| 2005/0013879 A1 | 1/2005 | Lin et al. |
| 2005/0021102 A1 | 1/2005 | Ignagni et al. |
| 2005/0027338 A1 | 2/2005 | Hill |

(56) References Cited

U.S. PATENT DOCUMENTS

| | | |
|---|---|---|
| 2005/0033136 A1 | 2/2005 | Govari et al. |
| 2005/0033137 A1 | 2/2005 | Oral et al. |
| 2005/0043765 A1 | 2/2005 | Williams et al. |
| 2005/0065567 A1 | 3/2005 | Lee et al. |
| 2005/0070981 A1 | 3/2005 | Verma |
| 2005/0075578 A1 | 4/2005 | Gharib et al. |
| 2005/0085865 A1 | 4/2005 | Tehrani |
| 2005/0085866 A1 | 4/2005 | Tehrani |
| 2005/0085867 A1 | 4/2005 | Tehrani et al. |
| 2005/0085868 A1 | 4/2005 | Tehrani et al. |
| 2005/0085869 A1 | 4/2005 | Tehrani et al. |
| 2005/0096710 A1 | 5/2005 | Kieval |
| 2005/0109340 A1 | 5/2005 | Tehrani |
| 2005/0113710 A1 | 5/2005 | Stahmann et al. |
| 2005/0115561 A1 | 6/2005 | Stahmann et al. |
| 2005/0131485 A1 | 6/2005 | Knudson et al. |
| 2005/0138791 A1 | 6/2005 | Black et al. |
| 2005/0138792 A1 | 6/2005 | Black et al. |
| 2005/0143787 A1 | 6/2005 | Boveja et al. |
| 2005/0165457 A1 | 7/2005 | Benser et al. |
| 2005/0182454 A1 | 8/2005 | Gharib et al. |
| 2005/0187584 A1 | 8/2005 | Denker et al. |
| 2005/0192655 A1 | 9/2005 | Black et al. |
| 2005/0251238 A1 | 11/2005 | Wallace et al. |
| 2005/0251239 A1 | 11/2005 | Wallace et al. |
| 2005/0288728 A1 | 12/2005 | Libbus et al. |
| 2005/0288730 A1 | 12/2005 | Deem et al. |
| 2006/0030894 A1 | 2/2006 | Tehrani |
| 2006/0035849 A1 | 2/2006 | Spiegelman et al. |
| 2006/0058852 A1 | 3/2006 | Koh et al. |
| 2006/0074449 A1 | 4/2006 | Denker et al. |
| 2006/0122661 A1 | 6/2006 | Mandell |
| 2006/0122662 A1 | 6/2006 | Tehrani et al. |
| 2006/0130833 A1 | 6/2006 | Younes |
| 2006/0142815 A1 | 6/2006 | Tehrani et al. |
| 2006/0149334 A1 | 7/2006 | Tehrani et al. |
| 2006/0155222 A1 | 7/2006 | Sherman et al. |
| 2006/0167523 A1 | 7/2006 | Tehrani et al. |
| 2006/0188325 A1 | 8/2006 | Dolan |
| 2006/0195159 A1 | 8/2006 | Bradley et al. |
| 2006/0217791 A1 | 9/2006 | Spinka et al. |
| 2006/0024222 A1 | 10/2006 | Bradley et al. |
| 2006/0224209 A1 | 10/2006 | Meyer |
| 2006/0229677 A1 | 10/2006 | Moffitt et al. |
| 2006/0247729 A1 | 11/2006 | Tehrani et al. |
| 2006/0253161 A1 | 11/2006 | Libbus et al. |
| 2006/0253182 A1 | 11/2006 | King |
| 2006/0258667 A1 | 11/2006 | Teng |
| 2006/0259107 A1 | 11/2006 | Caparso et al. |
| 2006/0282131 A1 | 12/2006 | Caparso et al. |
| 2006/0287679 A1 | 12/2006 | Stone |
| 2007/0005053 A1 | 1/2007 | Dando |
| 2007/0021795 A1 | 1/2007 | Tehrani |
| 2007/0027448 A1 | 2/2007 | Paul et al. |
| 2007/0087314 A1 | 4/2007 | Gomo |
| 2007/0093875 A1 | 4/2007 | Chavan et al. |
| 2007/0106357 A1 | 5/2007 | Denker et al. |
| 2007/0112402 A1 | 5/2007 | Grill et al. |
| 2007/0112403 A1 | 5/2007 | Moffitt et al. |
| 2007/0118183 A1 | 5/2007 | Gelfand et al. |
| 2007/0150006 A1 | 6/2007 | Libbus et al. |
| 2007/0168007 A1 | 7/2007 | Kuzma et al. |
| 2007/0173900 A1 | 7/2007 | Siegel et al. |
| 2007/0191908 A1 | 8/2007 | Jacob et al. |
| 2007/0196780 A1 | 8/2007 | Ware et al. |
| 2007/0203549 A1 | 8/2007 | Demarais et al. |
| 2007/0208388 A1 | 9/2007 | Jahns et al. |
| 2007/0221224 A1 | 9/2007 | Pittman et al. |
| 2007/0240718 A1 | 10/2007 | Daly |
| 2007/0250056 A1 | 10/2007 | Vanney |
| 2007/0250162 A1 | 10/2007 | Royalty |
| 2007/0255379 A1 | 11/2007 | Williams et al. |
| 2007/0265611 A1 | 11/2007 | Ignagni et al. |
| 2007/0288076 A1 | 12/2007 | Bulkes et al. |
| 2008/0039916 A1 | 2/2008 | Colliou et al. |
| 2008/0065002 A1 | 3/2008 | Lobl et al. |
| 2008/0125828 A1 | 5/2008 | Ignagni et al. |
| 2008/0161878 A1 | 7/2008 | Tehrani et al. |
| 2008/0167695 A1 | 7/2008 | Tehrani et al. |
| 2008/0177347 A1 | 7/2008 | Tehrani et al. |
| 2008/0183186 A1 | 7/2008 | Bly et al. |
| 2008/0183187 A1 | 7/2008 | Bly |
| 2008/0183239 A1 | 7/2008 | Tehrani et al. |
| 2008/0183240 A1 | 7/2008 | Tehrani et al. |
| 2008/0183253 A1 | 7/2008 | Bly |
| 2008/0183254 A1 | 7/2008 | Bly et al. |
| 2008/0183255 A1 | 7/2008 | Bly et al. |
| 2008/0183259 A1 | 7/2008 | Bly et al. |
| 2008/0183264 A1 | 7/2008 | Bly et al. |
| 2008/0183265 A1 | 7/2008 | Bly et al. |
| 2008/0188903 A1 | 8/2008 | Tehrani et al. |
| 2008/0215106 A1 | 9/2008 | Lee et al. |
| 2008/0288010 A1 | 11/2008 | Tehrani et al. |
| 2008/0288015 A1 | 11/2008 | Tehrani et al. |
| 2008/0312712 A1 | 12/2008 | Penner |
| 2008/0312725 A1 | 12/2008 | Penner |
| 2009/0024047 A1 | 1/2009 | Shipley et al. |
| 2009/0036947 A1 | 2/2009 | Westlund et al. |
| 2009/0118785 A1 | 5/2009 | Ignagni et al. |
| 2009/0275956 A1 | 11/2009 | Burnes et al. |
| 2009/0275996 A1 | 11/2009 | Burnes et al. |
| 2009/0276022 A1 | 11/2009 | Burnes et al. |
| 2009/0318993 A1 | 12/2009 | Eidenschink et al. |
| 2010/0022950 A1 | 1/2010 | Anderson et al. |
| 2010/0036451 A1 | 2/2010 | Hoffer |
| 2010/0077606 A1 | 4/2010 | Black et al. |
| 2010/0094376 A1 | 4/2010 | Penner |
| 2010/0114227 A1 | 5/2010 | Cholette |
| 2010/0114254 A1 | 5/2010 | Kornet |
| 2010/0198296 A1 | 8/2010 | Ignagni et al. |
| 2010/0204766 A1 | 8/2010 | Zdeblick et al. |
| 2010/0249865 A1* | 9/2010 | Zhang ............... A61B 5/14535 607/17 |
| 2010/0268311 A1 | 10/2010 | Cardinal et al. |
| 2010/0319691 A1 | 12/2010 | Lurie et al. |
| 2011/0060381 A1 | 3/2011 | Ignagni et al. |
| 2011/0077726 A1 | 3/2011 | Westlund et al. |
| 2011/0093032 A1 | 4/2011 | Boggs, II et al. |
| 2011/0118815 A1 | 5/2011 | Kuzma et al. |
| 2011/0230932 A1 | 9/2011 | Tehrani et al. |
| 2011/0230935 A1 | 9/2011 | Zdeblick |
| 2011/0230945 A1 | 9/2011 | Ohtaka et al. |
| 2011/0270358 A1 | 11/2011 | Davis et al. |
| 2011/0288609 A1 | 11/2011 | Tehrani et al. |
| 2012/0035684 A1 | 2/2012 | Thompson et al. |
| 2012/0053654 A1 | 3/2012 | Tehrani et al. |
| 2012/0078320 A1 | 3/2012 | Schotzko et al. |
| 2012/0130217 A1 | 5/2012 | Kauphusman et al. |
| 2012/0158091 A1 | 6/2012 | Tehrani et al. |
| 2012/0209284 A1 | 8/2012 | Westlund et al. |
| 2012/0215278 A1 | 8/2012 | Penner |
| 2012/0271382 A1 | 10/2012 | Arcot-Krishnamurthy et al. |
| 2012/0323293 A1 | 12/2012 | Tehrani et al. |
| 2013/0018247 A1 | 1/2013 | Glenn et al. |
| 2013/0018427 A1 | 1/2013 | Pham et al. |
| 2013/0023972 A1 | 1/2013 | Kuzma et al. |
| 2013/0030496 A1 | 1/2013 | Karamanoglu et al. |
| 2013/0030497 A1 | 1/2013 | Karamanoglu et al. |
| 2013/0030498 A1 | 1/2013 | Karamanoglu et al. |
| 2013/0060245 A1 | 3/2013 | Grunewald et al. |
| 2013/0116743 A1 | 5/2013 | Karamanoglu et al. |
| 2013/0123891 A1 | 5/2013 | Swanson |
| 2013/0131743 A1 | 5/2013 | Yamasaki et al. |
| 2013/0158625 A1 | 6/2013 | Gelfand et al. |
| 2013/0165989 A1 | 6/2013 | Gelfand et al. |
| 2013/0167372 A1 | 7/2013 | Black et al. |
| 2013/0197601 A1 | 8/2013 | Tehrani et al. |
| 2013/0237906 A1 | 9/2013 | Park et al. |
| 2013/0268018 A1 | 10/2013 | Brooke et al. |
| 2013/0289686 A1 | 10/2013 | Masson et al. |
| 2013/0296964 A1 | 11/2013 | Tehrani |
| 2013/0296973 A1 | 11/2013 | Tehrani et al. |
| 2013/0317587 A1 | 11/2013 | Barker |
| 2013/0333696 A1 | 12/2013 | Lee et al. |

(56) References Cited

U.S. PATENT DOCUMENTS

| | | |
|---|---|---|
| 2014/0067032 A1 | 3/2014 | Morris et al. |
| 2014/0088580 A1 | 3/2014 | Wittenberger et al. |
| 2014/0114371 A1 | 4/2014 | Westlund et al. |
| 2014/0121716 A1 | 5/2014 | Casavant et al. |
| 2014/0128953 A1 | 5/2014 | Zhao et al. |
| 2014/0148780 A1 | 5/2014 | Putz |
| 2014/0316486 A1 | 10/2014 | Zhou et al. |
| 2014/0324115 A1 | 10/2014 | Ziegler et al. |
| 2014/0378803 A1 | 12/2014 | Geistert et al. |
| 2015/0018839 A1 | 1/2015 | Morris et al. |
| 2015/0034081 A1 | 2/2015 | Tehrani et al. |
| 2015/0045810 A1 | 2/2015 | Hoffer et al. |
| 2015/0045848 A1 | 2/2015 | Cho et al. |
| 2015/0119950 A1 | 4/2015 | Demmer et al. |
| 2015/0165207 A1 | 6/2015 | Karamanoglu |
| 2015/0196354 A1 | 7/2015 | Haverkost et al. |
| 2015/0196356 A1 | 7/2015 | Kauphusman et al. |
| 2015/0202448 A1 | 7/2015 | Hoffer et al. |
| 2015/0231348 A1 | 8/2015 | Lee et al. |
| 2015/0250982 A1 | 9/2015 | Osypka et al. |
| 2015/0265833 A1 | 9/2015 | Meyyappan et al. |
| 2015/0283340 A1 | 10/2015 | Zhang et al. |
| 2015/0290476 A1 | 10/2015 | Krocak et al. |
| 2015/0359487 A1 | 12/2015 | Coulombe |
| 2015/0374252 A1 | 12/2015 | De La Rama et al. |
| 2015/0374991 A1 | 12/2015 | Morris et al. |
| 2016/0001072 A1 | 1/2016 | Gelfand et al. |
| 2016/0144078 A1 | 5/2016 | Young et al. |
| 2016/0193460 A1 | 7/2016 | Xu et al. |
| 2016/0228696 A1 | 8/2016 | Imran et al. |
| 2016/0239627 A1 | 8/2016 | Cerny et al. |
| 2016/0256692 A1 | 9/2016 | Baru |
| 2016/0310730 A1 | 10/2016 | Martins et al. |
| 2016/0331326 A1 | 11/2016 | Xiang et al. |
| 2016/0367815 A1 | 12/2016 | Hoffer |
| 2017/0007825 A1 | 1/2017 | Thakkar et al. |
| 2017/0013713 A1 | 1/2017 | Shah et al. |
| 2017/0021166 A1 | 1/2017 | Bauer et al. |
| 2017/0028191 A1 | 2/2017 | Mercanzini et al. |
| 2017/0036017 A1 | 2/2017 | Tehrani et al. |
| 2017/0050033 A1 | 2/2017 | Wechter |
| 2017/0143973 A1 | 5/2017 | Tehrani |
| 2017/0143975 A1 | 5/2017 | Hoffer et al. |
| 2017/0196503 A1 | 7/2017 | Narayan et al. |
| 2017/0224993 A1 | 8/2017 | Sathaye et al. |
| 2017/0232250 A1 | 8/2017 | Kim et al. |
| 2017/0252558 A1 | 9/2017 | O'Mahony et al. |
| 2017/0291023 A1 | 10/2017 | Kuzma et al. |
| 2017/0296812 A1 | 10/2017 | O'Mahony et al. |
| 2017/0312006 A1 | 11/2017 | Mcfarlin et al. |
| 2017/0312507 A1 | 11/2017 | Bauer et al. |
| 2017/0312508 A1 | 11/2017 | Bauer et al. |
| 2017/0312509 A1 | 11/2017 | Bauer et al. |
| 2017/0326359 A1 | 11/2017 | Gelfand et al. |
| 2017/0347921 A1 | 12/2017 | Haber et al. |
| 2018/0001086 A1 | 1/2018 | Bartholomew et al. |
| 2018/0008821 A1 | 1/2018 | Gonzalez et al. |
| 2018/0110562 A1 | 4/2018 | Govari et al. |
| 2018/0117334 A1 | 5/2018 | Jung |
| 2018/0256440 A1 | 9/2018 | Francois et al. |
| 2021/0077807 A1* | 3/2021 | Gani ............ A61N 1/3611 |

FOREIGN PATENT DOCUMENTS

| | | |
|---|---|---|
| EP | 0993840 A1 | 4/2000 |
| EP | 1304135 A2 | 4/2003 |
| EP | 0605796 B1 | 8/2003 |
| EP | 2489395 A1 | 8/2012 |
| EP | 3180073 B1 | 3/2020 |
| FR | 2801509 A1 | 6/2001 |
| JP | H08510677 A | 11/1996 |
| JP | 2003503119 A | 1/2003 |
| JP | 2010516353 A | 5/2010 |
| JP | 2011200571 A | 10/2011 |
| JP | 2012000195 A | 1/2012 |
| WO | WO-9407564 A2 | 4/1994 |
| WO | WO-9508357 A1 | 3/1995 |
| WO | WO-9964105 A1 | 12/1999 |
| WO | WO-9965561 A1 | 12/1999 |
| WO | WO-0100273 A1 | 1/2001 |
| WO | WO-02058785 A1 | 8/2002 |
| WO | WO-03005887 A2 | 1/2003 |
| WO | WO-03094855 A1 | 11/2003 |
| WO | WO-2006110338 A1 | 10/2006 |
| WO | WO-2006115877 A1 | 11/2006 |
| WO | WO-2007053508 A1 | 5/2007 |
| WO | WO-2008092246 A1 | 8/2008 |
| WO | WO-2008094344 A1 | 8/2008 |
| WO | WO-2009006337 A1 | 1/2009 |
| WO | WO-2009134459 A2 | 11/2009 |
| WO | WO-2010029842 A1 | 3/2010 |
| WO | WO-2010148412 A1 | 12/2010 |
| WO | WO-2011094631 A1 | 8/2011 |
| WO | WO-2011158410 A1 | 12/2011 |
| WO | WO-2012106533 A2 | 8/2012 |
| WO | WO-2013131187 A1 | 9/2013 |
| WO | WO-2013188965 A1 | 12/2013 |
| WO | WO-2014008171 A1 | 1/2014 |
| WO | WO-2015075548 A1 | 5/2015 |
| WO | WO-2015109401 A1 | 7/2015 |
| WO | 2016025912 A1 | 2/2016 |
| WO | WO-2019154834 A1 | 8/2019 |
| WO | WO-2019154837 A1 | 8/2019 |
| WO | WO-2019154839 A1 | 8/2019 |

OTHER PUBLICATIONS

Antonica A., et al., "Vagal Control of Lymphocyte Release from Rat Thymus," Journal of the Autonomic Nervous System, Elsevier, vol. 48(3), Aug. 1994, pp. 187-197.

Ayas N.T., et al., "Prevention of Human Diaphragm Atrophy with Short periods of Electrical Stimulation," American Journal of Respiratory and Critical Care Medicine, Jun. 1999, vol. 159(6), pp. 2018-2020.

Borovikova, et al., "Role of the Vagus Nerve in the Anti-Inflammatory Effects of CNI-1493," Proceedings of the Annual Meeting of Professional Research Scientists: Experimental Biology 2000, Abstract 97.9, Apr. 15-18, 2000.

Borovikova L.V., et al., "Role of Vagus Nerve Signaling in CNI-1493-Mediated Suppression of Acute Inflammation," Autonomic Neuroscience: Basic and Clinical, vol. 85 (1-3), Dec. 20, 2000, pp. 141-147.

Borovikova L.V., et al., "Vagus Nerve Stimulation Attenuates the Systemic Inflammatory Response to Endotoxin," Nature, Macmillan Magazines Ltd, vol. 405, May 25, 2000, pp. 458-462.

Chinese Search Report for Application No. CN2013/80023357.5, dated Jul. 24, 2015.

Co-pending U.S. Appl. No. 15/606,867, filed May 26, 2017.

Daggeti, W.M. et al., "Intracaval Electrophrenic Stimulation. I. Experimental Application during Barbiturate Intoxication Hemorrhage and Gang," Journal of Thoracic and Cardiovascular Surgery, 1966, vol. 51 (5), pp. 676-884.

Daggeti, W.M. et al., "Intracaval electrophrenic stimulation. II. Studies on Pulmonary Mechanics Surface Tension Urine Flow and Bilateral Ph," Journal of Thoracic and Cardiovascular Surgery, 1970, vol. 60(1 ), pp. 98-107.

De Gregorio, M.A. et al., "The Gunther Tulip Retrievable Filter: Prolonged Temporary Filtration by Repositioning within the Inferior Vena Cava," Journal of Vascular and Interventional Radiology, 2003, vol. 14, pp. 1259-1265.

Deng Y-J et al., "The Effect of Positive Pressure Ventilation Combined with Diaphragm Pacing on Respiratory Mechanics in Patients with Respiratory Failure; Respiratory Mechanics," Chinese critical care medicine, Apr. 2011, vol. 23(4), pp. 213-215.

Escher, Doris J.W. et al., "Clinical Control of Respiration by Transvenous Phrenic Pacing," American Society for Artificial Internal Organs: Apr. 1968—vol. 14—Issue 1—pp. 192-197.

European Search Report for U.S. Appl. No. 13/758,363, dated Nov. 12, 2015.

(56) References Cited

OTHER PUBLICATIONS

European Search Report for Application No. EP17169051.4, dated Sep. 8, 2017, 7 pages.
Extended European Search Report for Application No. 14864542.7, dated Jun. 2, 2017, 8 pages.
Extended European Search Report for Application No. 15740415.3, dated Jul. 7, 2017.
Fleshner M., et al., "Thermogenic and Corticosterone Responses to Intravenous Cytokines (IL-1β and TNF-α) are Attenuated by Subdiaphragmatic Vagotomy," Journal of Neuroimmunology, vol. 86, Jun. 1998, pp. 134-141.
Frisch S., "A Feasibility Study of a Novel Minimally Invasive Approach for Diaphragm Pacing," Master of Science Thesis, Simon Fraser University, 2009, p. 148.
Furman, S., "Transvenous Stimulation of the Phrenic Nerves," Journal of Thoracic and Cardiovascular Surgery, 1971, vol. 62 (5), pp. 743-751.
Gaykema R.P.A. et al., "Subdiaphragmatic Vagotomy Suppresses Endotoxin-Induced Activation of Hypothalamic Corticotropin-Releasing Hormone Neurons and ACTH Secretion," Endocrinology, The Endocrine Society, vol. 136 (10), 1995, pp. 4717-4720.
Gupta A.K., "Respiration Rate Measurement Based on Impedance Pneumography," Data Acquisition Products, Texas Instruments, Application Report, SBAA181, Feb. 2011, 11 pages.
Guslandi M., "Nicotine Treatment for Ulcerative Colitis," The British Journal of Clinical Pharmacology, Blackwell Science Ltd, vol. 48, 1999, pp. 481-484.
Hoffer J.A. et al., "Diaphragm Pacing with Endovascular Electrodes", IFESS 2010—International Functional Electrical Stimulation Society, 15th Anniversary Conference, Vienna, Austria, Sep. 2010.
Huffman, William J. et al., "Modulation of Neuroinflammation and Memory Dysfunction Using Percutaneous Vagus Nerve Stimulation in Mice," Brain Stimulation, 2018.
Ishii, K. et al., "Effects of Bilateral Transvenous Diaphragm Pacing on Hemodynamic Function in Patients after Cardiac Operations," J. Thorac. Cardiovasc. Surg., 1990.
Japanese Office Action in corresponding Japanese Application No. 2014-560202, dated Dec. 6, 2016, 4 pages.
Japanese Office Action in corresponding Japanese Application No. 2014-560202, dated Oct. 17, 2017, 5 pages.
Kawashima K., et al., "Extraneuronal Cholinergic System in Lymphocytes," Pharmacology & Therapeutics, Elsevier, vol. 86, 2000, pp. 29-48.
Levine S., et al., "Rapid disuse atrophy of diaphragm fibers in mechanically ventilated humans," New England Journal of Medicine, 2008, vol. 358, pp. 1327-1335.
Lungpacer: Therapy, News .< http://lungpacer.com>. Accessed Dec. 27, 2016.
Madretsma, G.S., et al., "Nicotine Inhibits the In-vitro Production of Interleukin 2 and Tumour Necrosis Factor-α by Human Mononuclear Cells," Immunopharmacology, Elsevier, vol. 35(1), Oct. 1996, pp. 47-51.
Marcy, T.W. et al., "Diaphragm Pacing for Ventilatory Insufficiency," Journal of Intensive Care Medicine, 1987, vol. 2 (6), pp. 345-353.
Meyyappan R., "Diaphragm Pacing during Controlled Mechanical Ventilation: Pre-Clinical Observations Reveal A Substantial Improvement In Respiratory Mechanics", 17th Biennial Canadian Biomechanics Society Meeting, Burnaby, BC, Jun. 6-9, 2012.
Nabutovsky, Y., et al., "Lead Design and Initial Applications of a New Lead for Long-Term Endovascular Vagal Stimulation," PACE, Blackwell Publishing, Inc, vol. 30(1), Jan. 2007, pp. S215-S218.
Notification of Reasons for Rejection and English language translation issued in corresponding Japanese Patent Application No. 2015-517565, dated Mar. 28, 2017, 6 pages.
Onders R.,, "A Diaphragm Pacing as a Short-Term Assist to Positive Pressure Mechanical Ventilation in Critical Care Patients," Chest, Oct. 24, 2007, vol. 132(4), pp. 571S-572S.

Onders R.,, "Diaphragm Pacing for Acute Respiratory Failure," Difficult Decisions in Thoracic Surgery, Chapter 37, Springer-Verlag, 2011, M.K. Ferguson (ed.), pp. 329-335.
Onders R, et al., "Diaphragm Pacing with Natural Orifice Transluminal Endoscopic Surgery: Potential for Difficult-To-Wean Intensive Care Unit Patients," Surgical Endoscopy, 2007, vol. 21, pp. 475-479.
Pavlovic D., et al., "Diaphragm Pacing During Prolonged Mechanical Ventilation of the Lungs could Prevent from Respiratory Muscle Fatigue," Medical Hypotheses, vol. 60 (3), 2003, pp. 398-403.
Planas R.F., et al., "Diaphragmatic Pressures: Transvenous vs. Direct Phrenic Nerve Stimulation," Journal of Applied Physiology, vol. 59(1), 1985, pp. 269-273.
Romanovsky, A.A., et al., "The Vagus Nerve in the Thermoregulatory Response to Systemic Inflammation," American Journal of Physiology, vol. 273 (1 Pt 2), 1997, pp. R407-R413.
Salmela L., et al., "Verification of the Position of a Central Venous Catheter by Intra-Atrial ECG. When does this method fail?," Acta Anasthesiol Scand, vol. 37 (1), 1993, pp. 26-28.
Sandborn W.J., "Transdermal Nicotine for Mildly to Moderately Active Ulcerative Colitis," Annals of Internal Medicine, vol. 126 (5), Mar. 1, 1997, pp. 364-371.
Sandoval R., "A Catch/Ike Property-Based Stimulation Protocol for Diaphragm Pacing", Master of Science Coursework project, Simon Fraser University, Mar. 2013.
Sarnoff, S.J. et al., "Electrophrenic Respiration," Science, 1948, vol. 108, p. 482.
Sato E., et al., "Acetylcholine Stimulates Alveolar Macrophages to Release Inflammatory Cell Chemotactic Activity," American Journal of Physiology, vol. 274 (Lung Cellular and Molecular Physiology 18), 1998, pp. L970-L979.
Sato, K.Z., et al., "Diversity of mRNA Expression for Muscarinic Acetylcholine Receptor Subtypes and Neuronal Nicotinic Acetylcholine Receptor Subunits in Human Mononuclear Leukocytes and Leukemic Cell Lines," Neuroscience Letters, vol. 266 (1), 1999, pp. 17-20.
Schauerte P., et al., "Transvenous Parasympathetic Nerve Stimulation in the Inferior Vena Cava and Atrioventricular Conduction," Journal of Cardiovascular Electrophysiology, vol. 11 (1), Jan. 2000, pp. 64-69.
Schauerte P.N., et al., "Transvenous Parasympathetic Cardiac Nerve Stimulation: An Approach for Stable Sinus Rate Control," Journal of Cardiovascular Electrophysiology, vol. 10 (11), Nov. 1999, pp. 1517-1524.
Scheinman R.I., et al., "Role of Transcriptional Activation of IκBα in Mediation of Immunosuppression by Glucocorticoids," Science, vol. 270, Oct. 13, 1995, pp. 283-286.
Sher, M.E., et al., "The Influence of Cigarette Smoking on Cytokine Levels in Patients with Inflammatory Bowel Disease," Inflammatory Bowel Diseases, vol. 5 (2), May 1999, pp. 73-78.
Steinlein, O., "New Functions for Nicotinic Acetylcholine Receptors? ," Behavioural Brain Research, vol. 95, 1998, pp. 31-35.
Sternberg E.M., (Series Editor) "Neural-Immune Interactions in Health and Disease," The Journal of Clinical Investigation, vol. 100 (11), Dec. 1997, pp. 2641-2647.
Sykes., A.P., et al., "An Investigation into the Effect and Mechanisms of Action of Nicotine in Inflammatory Bowel Disease," Inflammation Research, vol. 49, 2000, pp. 311-319.
Toyabe S., et al., "Identification of Nicotinic Acetylcholine Receptors on Lymphocytes in the Periphery as well as Thymus in Mice," Immunology, vol. 92, 1997, pp. 201-205.
Van Dijk A.P.M., et al., "Transdermal Nicotine Inhibits Interleukin 2 Synthesis by Mononuclear Cells Derived from Healthy Volunteers," European Journal of Clinical Investigation, vol. 28, 1998, pp. 664-671.
Wanner, A. et al., "Trasvenous Phrenic Nerve Stimulation in Anesthetized Dogs," Journal of Applied Physiology, 1973, vol. 34 (4), pp. 489-494.
Watkins L.R., et al., "Blockade of Interleukin-1 Induced Hyperthermia by Subdiaphragmatic Vagotomy: Evidence for Vagal Mediation of Immune-Brain Communication," Neuroscience Letters, vol. 183, 1995, pp. 27-31.

(56) References Cited

OTHER PUBLICATIONS

Watkins L.R., et al., "Implications of Immune-to-Brain Communication for Sickness and Pain," PNAS (Proceedings of the National Academy of Sciences of the USA), vol. 96 (14), Jul. 6, 1999, pp. 7710-7713.

Whaley K., et al., "C2 Synthesis by Human Monocytes is Modulated by a Nicotinic Cholinergic Receptor," Nature, vol. 293, Oct. 15, 1981, pp. 580-582 (and reference page).

PCT Search Report dated Oct. 26, 2018 for PCT Application No. PCT/IB2018/000603, 7 pages.

PCT Search Report and Written Opinion dated Oct. 17, 2018 for PCT Application No. PCT/US2018/043661, 13 pages.

Non-Final Office Action in U.S. Appl. No. 16/906,154, dated Jul. 16, 2020 (49 pages).

\* cited by examiner

STIMULATION SYSTEMS AND RELATED USER INTERFACES

CROSS-REFERENCE TO RELATED APPLICATION

This application claims priority to U.S. Provisional Application No. 62/757,576, filed on Nov. 8, 2018, which is hereby incorporated by reference in its entirety. All publications, patent applications, and patents mentioned in this specification are herein incorporated by reference in their entirety to the same extent as if each individual document was specifically individually indicated to be incorporated by reference.

TECHNICAL FIELD

Embodiments this disclosure relate to systems, methods, and associated graphical user interfaces for stimulations of a body. Embodiments of this disclosure generally relate to methods and devices (including systems) for the stimulation of nerves and/or muscles, including a user interface for se during the stimulation of muscles and/or nerves. In embodiments, systems may restore, enhance, and/or modulate of diminished neurophysiological functions using electrical stimulation. Some embodiments provide methods for mapping and selecting the electrodes proximate to one or more target nerves. Non-limiting embodiments include systems, electrode structures, electrode positions, mapping methodologies, sensors arrangements, and associated graphical user interfaces for interfacing with systems described herein.

BACKGROUND

Critical care patients, particularly those requiring invasive mechanical ventilation (MV), are known to experience higher levels of diaphragm, lung, brain, heart, and other organ injury. The respiratory muscles (e.g., diaphragm, sternocleidomastoid, scalenes, pectoralis minor, external intercostals, internal intercostals, abdominals, quadratus, etc.) are known to rapidly lose mass and strength during MV. The lungs suffer from ventilator-induced trauma, including both high and low pressure injuries. Cognitive effects of MV are believed to be caused by several factors, including aberrant neuro-signaling and inflammatory responses. To prevent these negative side effects, it is important to keep patients on MV for as short a time as possible. However, rapid respiratory muscle atrophy in MV patients makes it challenging to transition many patients away from a dependency on MV. Options are limited for strengthening the respiratory muscles of critical care patients, particularly for those that are on MV, so that they can quickly regain the ability to breathe without external respiratory support.

SUMMARY

Embodiments of the present disclosure relate to, among other things, systems, devices, and methods for applying stimulation to one or more anatomical targets. Embodiments of the systems, methods, and user interfaces for the systems and methods described herein, may be used with alternatives and/or supplements to MV, such as, for example, stimulation of respiratory nerves and/or respiratory muscles. Each of the embodiments disclosed herein may include one or more of the features described in connection with any of the other disclosed embodiments.

In one example, a system for stimulating body tissue may comprise a user interface and a control unit including a processor and a non-transitory computer readable medium storing instructions. The instructions, when executed by the processor, may cause the processor to identify an electrode combination and determine a threshold charge for use in stimulating the body tissue, based at least partially on input received via the user interface.

Any of the systems disclosed herein may include any of the following features. The instructions stored in the non-transitory computer readable medium may cause the processor, when identifying the electrode combination, to select a set of electrode combinations from a domain of electrode combinations, stimulate from all selected electrode combinations, and receive input on whether a requisite stimulation was detected for each stimulation. The instructions stored in the non-transitory computer readable medium may cause the processor, when identifying the electrode combination, to individually select an electrode combination from the set of electrode combinations which provided the requisite stimulation, stimulate from the individually selected electrode combination, and for each stimulation, receive input on whether the requisite stimulation was detected. Receiving input on whether the requisite stimulation was detected may include prompting a user to provide feedback via the user interface on whether the requisite stimulation was detected. The instructions stored in the non-transitory computer readable medium may cause the processor, when determining a threshold charge, to determine a coarse threshold charge and a fine threshold charge. Further, when identifying a coarse threshold charge, the instructions stored in the non-transitory computer readable medium may cause the processor to perform an electrode sweep at a first charge, receive input on whether a requisite stimulation was detected, and if the requisite stimulation was detected, set the coarse threshold charge at a charge of the most recent electrode sweep, or, if the requisite stimulation was not detected, perform an electrode sweep at a second charge greater than the first charge. When identifying a fine threshold charge, the instructions stored in the non-transitory computer readable medium may cause the processor to select a charge level that corresponds to a determined coarse threshold, determine a domain of charges based on the determined coarse threshold, deliver stimulation at the charge level corresponding to the determined coarse threshold, and receive input on whether the requisite stimulation was detected. Systems for stimulating body tissue described herein may include one or more stimulation arrays supported on an intravenous catheter, and the body tissue is a muscle that activates a lung or nerve that innervates a muscle that activates a lung. The user interface may include an anatomical indication window, one or more phase buttons, and one or more stimulation level indication windows.

An example system for stimulating body tissue may comprise one or more sensors, a stimulation array, a user interface, and a control unit including a processor and a non-transitory computer readable medium. The sensors may be configured to be affixed to, or inserted in, a body to measure one or more physiological parameters of the body. The non-transitory computer readable medium may store instructions that, when executed by the processor, causes the processor to assess a position of the stimulation array, determine an electrode combination of the stimulation array for use in stimulating body tissue, and determine a threshold charge for use in stimulating the body tissue.

Any of the systems or methods disclosed herein may include any of the following features. The instructions stored in the non-transitory computer readable medium may cause the processor, when identifying the electrode combination, to select a set of electrode combinations form a domain of electrode combinations, stimulate from all selected electrode combinations, receive input on whether requisite stimulation was detected during stimulation from all selected electrode combinations, individually select an electrode combination from the set of electrode combinations which provided requisite stimulation, stimulate from the individually selected electrode combination, and receive input on whether the requisite stimulation was detected during stimulation from the individually selected electrode combination. The instructions stored in the non-transitory computer readable medium may cause the processor, when determining a threshold charge, to perform an electrode sweep at a first charge, receive input on whether requisite stimulation was detected, and if requisite stimulation was detected, set the coarse threshold charge at the charge of the most recent electrode sweep, or if requisite stimulation was not detected, perform an electrode sweep at a second charge, wherein the second charge is greater than the first charge. One or more sensors of a system for stimulating body tissue may include sensors configured to detect airway pressure, airway flowrate, transpulmonary pressure, tidal volume, blood gas levels, heart rate, breathing rate, impedance, lung gas distribution, electromyographic activity, transdiaphragmatic pressure, or a combinations thereof. The instructions stored in the non-transitory computer readable medium may cause the processor to assist a user in determining if the one or more stimulation arrays are correctly placed, relative to a patient, and/or schedule a number of stimulations within a set time interval. The stimulation array may include at least two groups of electrodes. Identifying an electrode combination may include identifying an electrode combination for each group of electrodes and identifying a threshold charge may include identifying a threshold charge for each group of electrodes. The instructions stored in the non-transitory computer readable medium may cause the processor, when prompted by a user, to terminate the delivery of stimulation energy. The instructions stored in the non-transitory computer readable medium may cause the processor to determine whether a stimulation would exceed a maximum allowable charge.

In one example, a system for stimulating body tissue may include a catheter, a user interface, and a control unit. The catheter may include a plurality of electrodes. The control unit may include a processor and a non-transitory computer readable medium storing instructions that, when executed by the processor, causes the processor to, based on input received via the user interface, determine a coarse threshold suitable for stimulating the body tissue, identify and electrode combination from the plurality of electrodes, and determine a fine threshold suitable for stimulating the body tissue via the identified electrode combination. The body tissue may be a phrenic nerve and the electrode combination may be used to deliver stimulation to the phrenic nerve.

Any of the systems or methods disclosed herein may include any of the following features. The instructions stored in the non-transitory computer readable medium may cause the processor to determine whether the catheter is placed in a position, relative to a body, suitable for delivering stimulation to the body tissue. The instructions stored in the non-transitory computer readable medium may cause the processor, when prompted by a user, to schedule a number of stimulations within a set time interval, where each stimulation of the number of stimulations is delivered via the identified electrode combination, and the number of stimulations and the duration of the time interval are parameters adjustable via the user interface.

BRIEF DESCRIPTION OF THE DRAWINGS

The accompanying drawings, which are incorporated in and constitute a part of this specification, illustrate non-limiting embodiments of the present disclosure and together with the description serve to explain the principles of the disclosure.

DETAILED DESCRIPTION

Throughout the following description, specific details are set forth to provide a more thorough understanding to persons skilled in the art. The following description of examples of the technology is not intended to be exhaustive or to limit the system to the precise forms of any example embodiment. Accordingly, the description and drawings are to be regarded in an illustrative sense, rather than a restrictive sense.

Further aspects of the disclosures and features of example embodiments are illustrated in the appended drawings and/or described in the text of this specification and/or described in the accompanying claims. It may be understood that both the foregoing general description and the following detailed description are exemplary and explanatory only and are not restrictive of the invention, as claimed. As used herein, the terms "comprises," "comprising," "including," "having," or other variations thereof, are intended to cover a non-exclusive inclusion such that a process, method, article, or apparatus that comprises a list of elements does not include only those elements, but may include other elements not expressly listed or inherent to such a process, method, article, or apparatus. Additionally, the term "exemplary" is used herein in the sense of "example," rather than "ideal."

As used herein, the term "proximal" means a direction closer to an operator and the term "distal" means a direction further from an operator. The term "approximately" or like terms (e.g., "about," "substantially") encompass values within 10% of the stated value.

Reference will now be made in detail to examples of the present disclosure described above and illustrated in the

Lung Control Unit (LCU)

In one or more embodiments, a system may include one or more stimulation arrays, such as for example, electrode arrays, connected (e.g., via a wired or wireless connection), to one or more circuits, processors, devices, systems, subsystems, applications, units, or controllers. Each stimulation array of the one or more stimulation arrays may include one or more nodes for delivering stimulation (e.g., one or more electrodes for delivering stimulation). The one or more stimulation arrays may be configured to be placed on, or inserted into, a patient (e.g., a neck, torso, blood vessel, etc., of the patient). In some embodiments, the one or more stimulation arrays may be supported on a catheter (e.g., a catheter configured for insertion into the patient, such as, for example, an intravenous catheter).

One or more user interfaces, as described below, may be used in combination with one or more systems, catheters, apparatuses, stimulation arrays, and electrodes, such as, for example, a Lung Control Unit (LCU). One exemplary LCU architecture is shown in FIG. 1.

Figure 1:
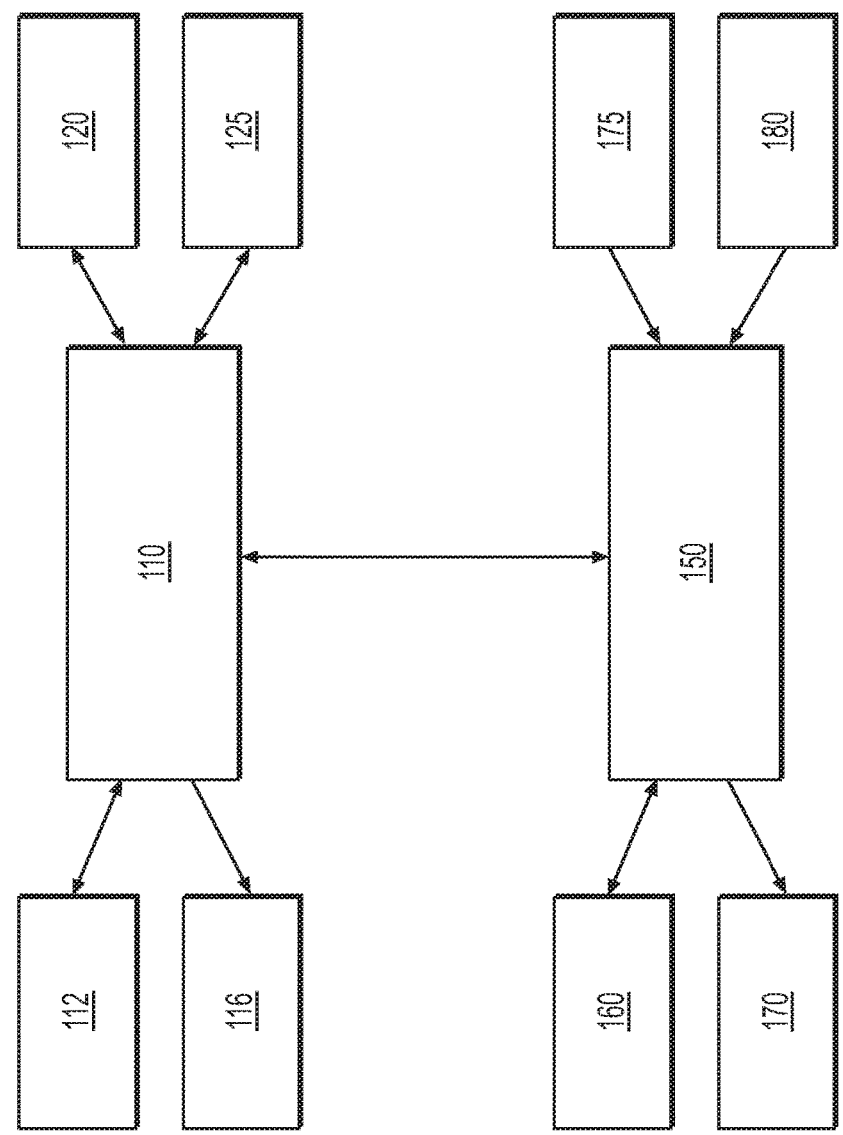
FIG. 1 illustrates a schematic view of a system including a GUI engine and an application engine, according to various embodiments of the present disclosure.

As shown in FIG. 1, an LCU 100 may include a GUI engine 110 which may be in communication with an application engine 150. The GUI engine 110 is primarily responsible for interfaces to the user and is used for configuring and monitoring system operation. A user interface 120 may be used to facilitate communication between a user and the GUI engine 110 and may include, for example, one of the user interfaces 120 described herein (e.g., placement mode GUI 200, mapping mode GUI 300, or therapy mode GUI 400). The GUI engine 110 may include an off-the-shelf single board computer (SBC). The GUI engine 110 may interface to one or more of a user interface 120, which may include a touchscreen, a video monitor, a remote controller, image display, tablet, smartphone, remote controller, and/or a touch sensor. Any of the user interfaces may provide visual, audible, or tactile information to the user. One or more touchscreens and/or video monitors may be in communication with the GUI engine 110 via, for example, a video graphics array (VGA) connector. One or more touch sensors may be in communication with the GUI engine 110 via, for example, a serial communication interface (e.g., RS-232). Other inputs to the GUI engine 110 may be transmitted via USB connection 125 (e.g., inputs from external communication tools, inputs from remote control devices). GUI engine 110 may also output data (e.g., data related to one or more stimulation parameters, one or more physiological parameters of a patient, or one or more operating parameters of a stimulation engine 170) to one or more other devices (e.g., a mechanical ventilator). In some embodiments, the GUI engine 110 may be in communication with a speaker 116 (e.g., a buzzer integrated into an SBC) and may be configured to output audio via speaker 116. The GUI engine 110 may be in communication with a mass storage device 112 (e.g., a solid-state drive (SSD)) via a serial interface (e.g., a serial AT attachment (SATA), such as, for example, a mini-SATA (m-SATA) interface).

The GUI engine 110 may be in two-way communication with an application engine 150 via a serial port (e.g., an isolated serial port). The application engine 150 may include one or more microcontrollers that control the stimulation and monitoring (e.g., an applications controller and/or a system health monitor 160). An application controller may control interfaces to a subject and therapy delivery. For example, the application controller may convert, modify, and/or translate signals or instructions from application engine 150 to electrical signals (e.g., stimulation pulses) delivered by stimulation engine 160. Accordingly, the application controller may facilitate bidirectional communication from the application engine 150 to the GUI engine 110, bidirectional communication from the application engine 150 to a system health monitor 160, stimulation voltage and current measurements, and/or bidirectional communication from the application engine 150 to the stimulation engine 170. The application engine 150 and the system health monitor 160 may be in communication via, for example, an asynchronous serial interface (e.g., a universal asynchronous receiver-transmitter (UART)) or general-purpose input/output (GPIO). The application engine 150 may interface with one or more voltage or current measuring devices (e.g., a stimulation monitor 175) via an analog-to-digital converter (ADC). The application engine 150 and the stimulation engine 170 may be in communication via, for example, a synchronous serial interface (e.g., a serial peripheral interface (SPI)) or GPIO.

The system health monitor 160 is primarily responsible for ensuring the delivery of therapy is safe and meets internal and external safety parameters. The system health monitor 160 interfaces with the stimulation electronics, e.g., stimulation engine 170, including the means for providing stimulation (e.g., one or more stimulation arrays, one or more electrodes, or a catheter/needle including one or more electrodes, or other stimulation device), for example, via application engine 150. In some embodiments, the stimulation monitoring unit 175 may monitor one or more aspects of the delivered stimulation, such as, identity of stimulation array (e.g., electrode(s) or electrode array(s)) delivering stimulation, stimulation amplitude, stimulation pulse width, stimulation frequency, stimulation duration, total charge delivered, etc., and communicate these aspects to system health monitor 160 (e.g., via application engine 150). System health monitor 160 may also monitor one or more aspects of the patient's health, such as, configured to detect airway pressure, airway flowrate, transpulmonary pressure, tidal volume, blood gas levels, heart rate, impedance, electromyographic activity, transdiaphragmatic pressure, and/or breathing rate and timing, via one or more sensors configured to monitor a physiological or other characteristic of the patient. The one or more sensors, such as, for example, sensors configured to detect airway pressure, airway flowrate, transpulmonary pressure, tidal volume, blood gas levels, heart rate, breathing rate, impedance (e.g., sensors configured for electrical impedance tomography), lung gas distribution, electromyographic activity, transdiaphragmatic pressure, or a combination thereof, may be configured to be affixed to a patient or inserted into a patient.

The stimulation engine 170 facilitates delivering stimulation to one or more anatomical targets (e.g., lung-accessories such as nerves and/or muscles related to respiration) via, for example, a single electrode combination (two, three, or more electrodes in a multi-polar configuration) at a given point in time. The stimulation may be delivered as a result of a request from the application controller. As used herein, delivered stimulation may refer to a finite number of stimulation pulses (in placement, mapping, or therapy modes) to be delivered to an anatomical target via an individual electrode combination. In some embodiments, the number and/or properties of stimulation pulses in delivered stimulation may depend on the stimulation duration, pulse frequency, stimulation frequency, stimulation pulse width, stimulation amplitude (current), any of which could be a selectable or programmable parameter via user interface 120.

The stimulation engine 170 may control stimulation timing and/or charge for delivered stimulation according to parameters passed from the application engine 150 prior to the commencement of stimulation delivery. In therapy mode, as described in greater detail below, the application controller may instruct the stimulation engine 170 to deliver repeated stimulation upon request from the user. In placement mode or mapping mode, the application controller may instruct the stimulation engine 170 to deliver multiple stimulation pulses, each consisting of a single stimulation pulse or series of finite pulses to a given electrode combination in order to achieve the stimulation deliveries required for placement mode and mapping mode. The frequency of the series of finite pulses in delivered stimulation may be different in different modes, for example in mapping or placement mode the frequency could be approximately 1 Hz to approximately 4 Hz and in the therapy mode the frequency could be approximately 8 Hz, approximately 10 Hz, approximately 11 Hz, approximately 15 Hz, approximately 20 Hz, approximately 25 Hz, approximately 40 Hz or other similar frequency.

One or more stimulation arrays may include one or more groups of electrodes. The electrodes may be configured to deliver stimulation as monopolar, bipolar, tripolar, or multipolar electrodes. As used herein, a stimulation being transmitted by an electrode may refer to an electrical signal being transmitted by a single electrode (anode) on the catheter to the ground reference (cathode) that is placed away from the anode to generate a larger electrical field (monopolar electrical stimulation), an electrical signal being transmitted from a anode electrode to cathode electrode on the catheter (bipolar stimulation), or an electrical signal being transmitted from one or more electrodes to one or more other electrodes (multipolar electrical stimulation) (e.g., from a cathode to two anodes, from two cathodes to an anode, or from a cathode to three or more anodes). As any of these electrode combinations and configurations are contemplated, for clarity when referring to one or more processes, methods, or modes of operation, such types of electrical signal transmission may all be referred to as a stimulation being transmitted by an electrode or an electrode combination.

As described above, one or more embodiments may include a computer system, such as, for example, computer systems that include a processor, e.g., a central processing unit (CPU), a graphics processing unit (GPU), or both. The processor may be a component in a variety of systems. For example, the processor may be part of a standard personal computer or a workstation. The processor may be one or more general processors, digital signal processors, application specific integrated circuits, field programmable gate arrays, servers, networks, digital circuits, analog circuits, combinations thereof, or other now known or later developed devices for analyzing and processing data. The processor may implement a software program, such as code generated manually (i.e., programmed).

A controller (e.g., application controller) may include a processor that is generally configured to accept information from one or more other components of an LCU 100, and process the information according to various algorithms to produce control signals for controlling the other components of LCU 100, such as, for example, stimulation engine 170. For example, the processor may accept information from the system and system components (e.g., user interface 120 or system health monitor 160), process the information according to various algorithms, and produce information signals that may be directed to visual indicators, digital displays, audio tone generators, or other indicators of, e.g., a user interface, in order to inform a user of the system status, component status, procedure status or any other information that is being monitored by the system. The processor may be a digital IC processor, analog processor or any other suitable logic or control system that carries out the control algorithms Further, one or more computer systems (e.g., LCU 100) described herein may include a memory. The memory may be a main memory, a static memory, or a dynamic memory (e.g., mass storage device 112). The memory may include, but is not limited to computer readable storage media such as various types of volatile and non-volatile storage media, including but not limited to random access memory, read-only memory, programmable read-only memory, electrically programmable read-only memory, electrically erasable read-only memory, flash memory, magnetic tape or disk, optical media and the like. In one implementation, the memory includes a cache or random-access memory for the processor. In alternative implementations, the memory is separate from the processor, such as a cache memory of a processor, the system memory, or other memory. The memory may be an external storage device or database for storing data. Examples include a hard drive, compact disc ("CD"), digital video disc ("DVD"), memory card, memory stick, floppy disc, universal serial bus ("USB") memory device, mass storage device 112, or any other device operative to store data. The memory is operable to store instructions executable by the processor. The functions, acts or tasks illustrated in the figures (e.g., FIGS. 5, and 7-9) or described herein may be performed by the programmed processor executing the instructions stored in the memory. The functions, acts or tasks are independent of the particular type of instructions set, storage media, processor or processing strategy and may be performed by software, hardware, integrated circuits, firm-ware, micro-code and the like, operating alone or in combination. Likewise, processing strategies may include multiprocessing, multitasking, parallel processing and the like.

In some systems, a computer-readable medium includes instructions or receives and executes instructions responsive to a propagated signal so that a device connected to a network can communicate voice, video, audio, images, or any other data over the network. Further, the instructions may be transmitted or received over the network via a communication port or interface. The communication port or interface may be a part of the processor or may be a separate component. The communication port may be created in software or may be a physical connection in hardware. The communication port may be configured to connect with a network, external media, user interface 120, or any other components in LCU 100, or combinations thereof. The connection with the network may be a physical connection, such as a wired Ethernet connection or may be established wirelessly. Likewise, the additional connections with other components of the LCU 100 may be physical connections or may be established wirelessly.

While the computer-readable medium is shown to be a single medium, the term "computer-readable medium" may include a single medium or multiple media, such as a centralized or distributed database, and/or associated caches and servers that store one or more sets of instructions. The term "computer-readable medium" may also include any medium that is capable of storing, encoding, or carrying a set of instructions for execution by a processor or that cause a computer system to perform any one or more of the methods or operations disclosed herein. The computer-readable medium may be non-transitory, and may be tangible.

User Interface

Figure 2:
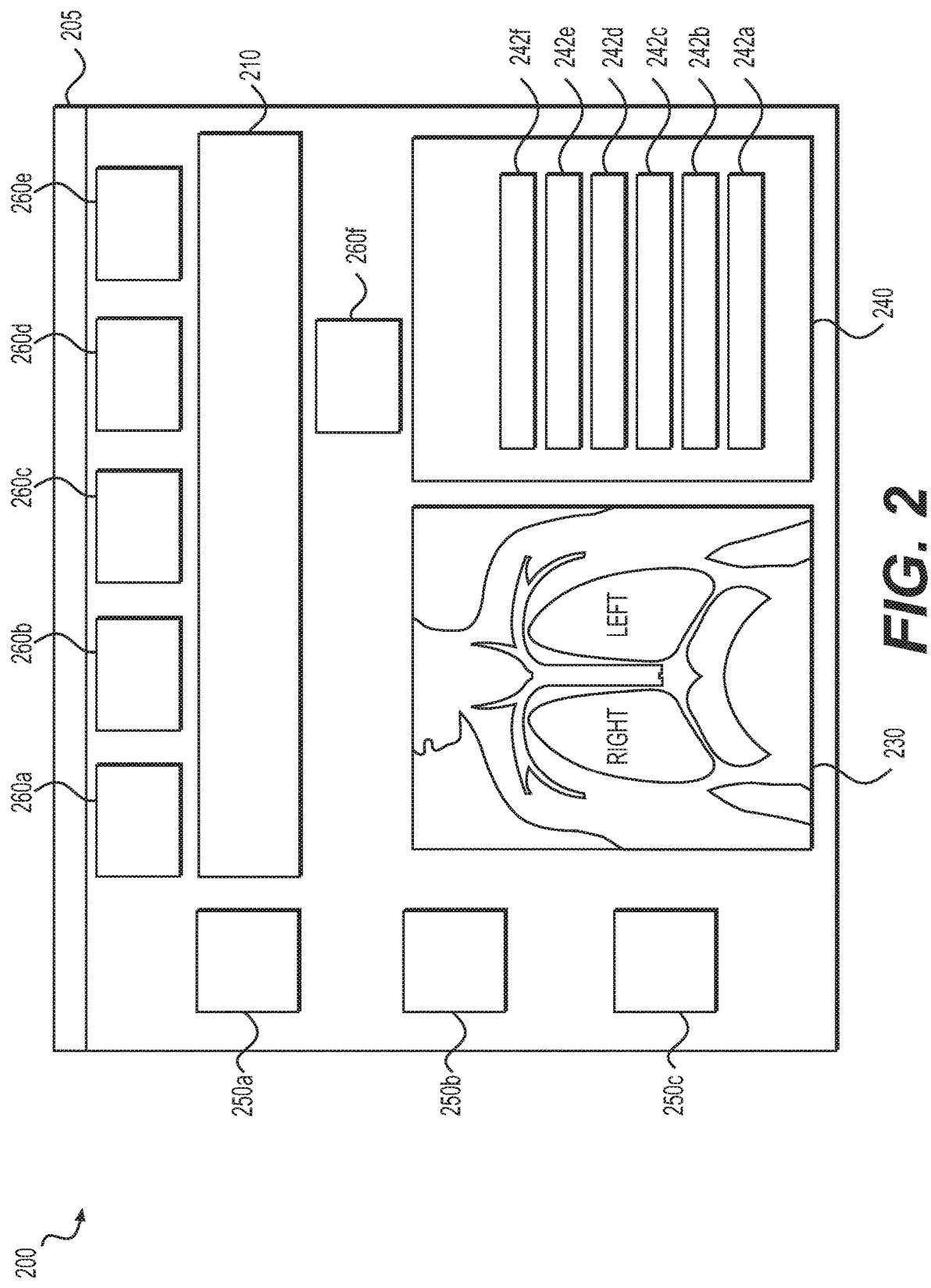
FIG. 2 illustrates a schematic view of a graphic user interface for placement mode operations, according to one or more embodiments of the present disclosure.
Figure 3:
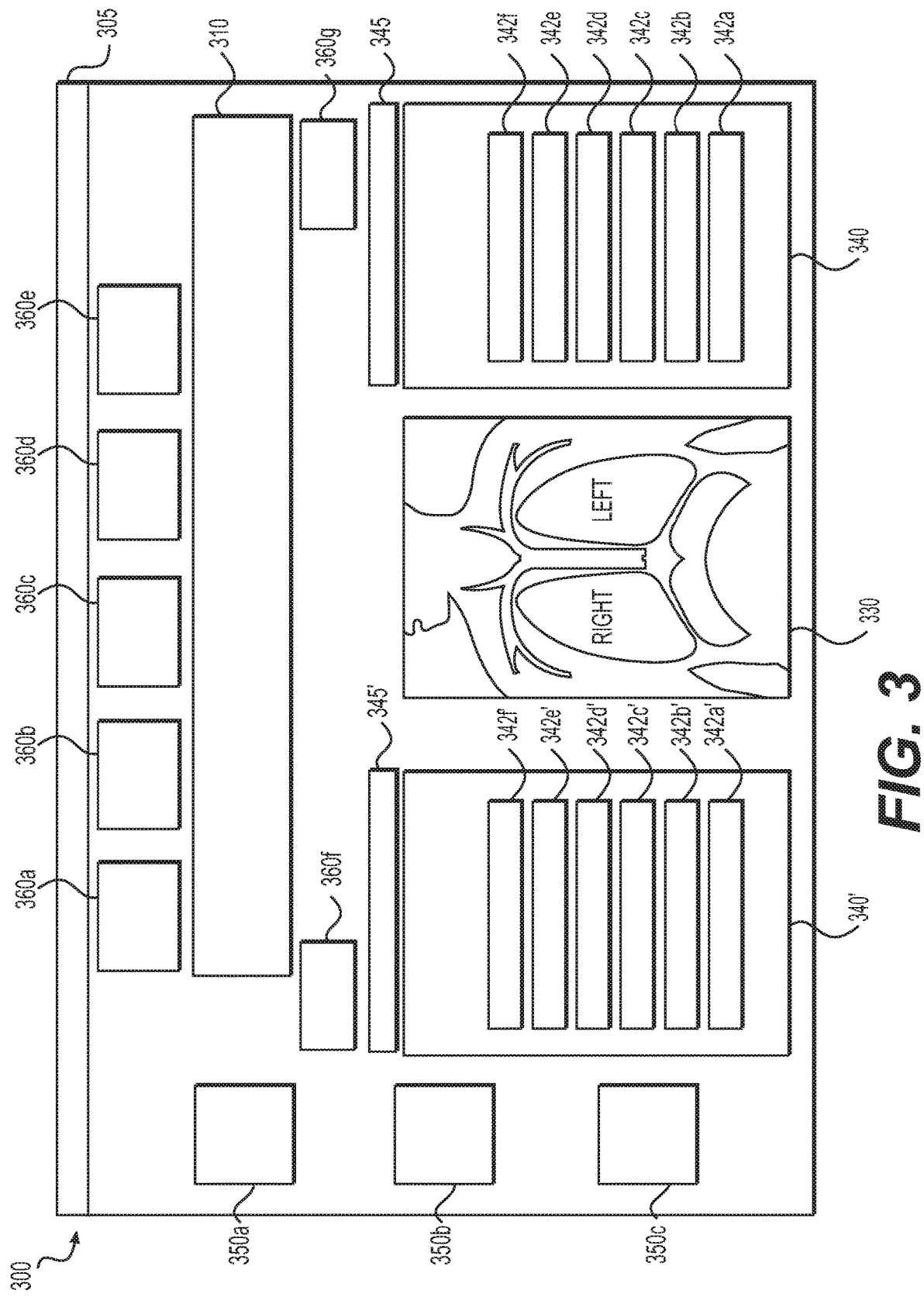
FIG. 3 illustrates a schematic view of a graphic user interface for mapping mode operations, according to various embodiments.
Figure 4:
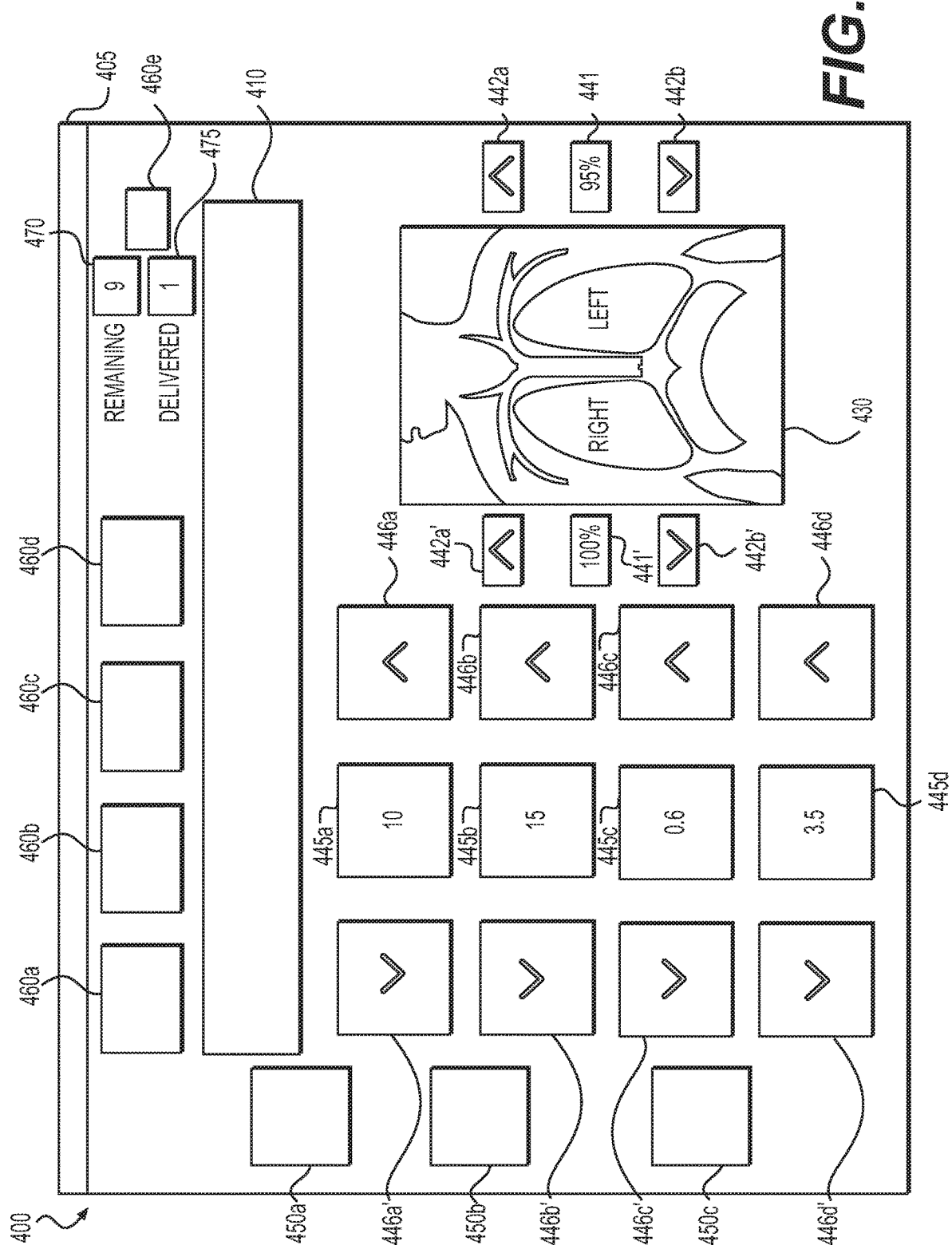
FIG. 4 illustrates a schematic view of a graphic user interface for therapy mode operations, according to one or more embodiments.

Systems and methods described herein may fall generally within three phases of operation: placement mode, mapping mode, and therapy mode. User interface 120 may change during each phase of operation or a user may be able to select between and/or navigate between each phase of operation. Arrangements of features of user interface 120 as they apply to each phase of operation may be described below, according to one or more embodiments. It should be understood that features of a user interface 120 according to one embodiment may be interchanged or used in combination with features of a user interface 120 according to one or more other embodiments. Further, although one or more buttons, zones, regions, displays, or other features of user interfaces 120 are shown in FIGS. 2-4 to be rectangular in shape, this is for clarity of illustration only. The one or more buttons, zones, regions, displays, or other features of the user interfaces 120 described herein may be of any shape (e.g., circular, ovular, oblong, triangular, etc.), size, color, orientation, or relative position.

Placement mode may be used just after the one or more stimulation arrays (e.g., supported on a catheter or other stimulation delivery system) has been inserted into, or placed in proximity to, a patient or adjusted relative to the patient. Placement mode may include executing a subset of left side mapping operations (e.g., left coarse threshold assessment, a coarse threshold assessment process 1100) where the user can quickly check for, as an example, contractions of one or more muscles associated with respiration to verify placement of a stimulation catheter.

In some embodiments, placement mode may include sensing the position of a catheter (e.g., a catheter supporting one or more stimulation arrays) within the body of a patient and providing feedback on such position to LCU 100. By way of non-limiting example, one or more sensors (e.g., an electrode supported on the catheter), may be used to detect a signal from the body (e.g., cardiac signals). Based on the characteristics of one or more detected signals, the LCU 100 may determine an appropriate placement of the catheter, relative to the body of the patient. During such operations, one or more components of a user interface 120 (e.g., an anatomical indication window 230 of placement mode GUI 200) may include a pictorial representation of the catheter in the patient, such as, for example, color signals (e.g. red, yellow, green) in select geographic shapes (e.g. circle, rectangle, oval, etc.) indicating a proximity to a target location. Additionally or in the alternative, sounds or other cues may be used to indicate placement or movement of a catheter.

Referring to FIG. 2, an exemplary user interface 120 for a user to interface with the LCU 100 during placement mode is shown, e.g., a placement mode GUI 200. Placement mode GUI 200 may be displayed on a touchscreen display, or other display means that allows for interactivity.

Placement mode GUI 200 may include a status bar 205, a notification box 210, an anatomical indication window 230, a stimulation indication window 240, one or more phase buttons 250a, 250b, 250c, and/or one or more action buttons 260a to 260e. Status bar 205 may be placed along an edge of placement mode GUI 200, such as, for example, along the top edge of placement mode GUI 200. Status bar 205 may display information (e.g., via graphic, text, or a combination thereof) related to the operation of the LCU 100. For example, status bar 205 may display information relating to the phase of operation (e.g., placement mode), date, time, parameters of stimulation, parameters of the patient, parameters of another device (e.g., a mechanical ventilator), session ID, LCU ID, or combinations thereof.

Notification box 210 may display information relating to operations of the LCU 100, such as, for example, a summary of stimulations recently delivered to a patient, instructions to a user, or a summary of parameters of stimulation. In some embodiments, notification box 210 is the primary means of placement mode GUI 200 to communicate instructions to the user regarding placement mode operations. For example, text or graphic instructions within notification box 210 may include instructions for the user to use LCU 100 through the placement mode phase of operations.

Anatomical indication window 230 may display graphics or text indicative of one or more anatomical structures, delivered electrical stimulation, or electrical stimulation delivered to one or more anatomical structures. For example, anatomical indication window 230 may include one or more images or renderings of a patient, a single lung, a pair of lungs, a diaphragm, one or two hemi-diaphragms, one or more blood vessels (e.g., jugular vein, subclavian vein, superior vena cava, subclavian artery, aorta, carotid artery), one or more nerves (e.g., left phrenic nerve, right phrenic nerve, vagus nerve, one or more cervical nerves), one or more electrodes, one or more stimulation arrays, a catheter supporting one or more stimulation arrays, or a combination thereof. Anatomical indication window 230 may also include text indicative of one or more anatomical structures, delivered electrical stimulation, or electrical stimulation delivered to one or more anatomical structures, such as, for example, left and right side designations. Various parts of anatomical indication window 230 may light up, change color, or otherwise be indicated when stimulation is being applied to one or more afferents of the indicated part. For example, during placement mode operations, stimulation may be delivered to nerves and/or muscles that are connected to or associated with the left lung. During the delivery of such stimulation to accessory anatomical structures of the left lung, a left lung part of anatomical indication window 230 (e.g., a left portion of the diaphragm and/or the left lung) may light up, change color, or otherwise be indicated. Similar indications may be made in anatomical indication window 230 which represent the delivery or placement of an electrode array or electrical stimulus to any anatomical structure (e.g., stimulation affecting a right lung, stimulation proximate to a vein, stimulation from an electrode array positioned proximate a hemi-diaphragm).

Stimulation indication window 240 may provide information to a user regarding one or more stimulation parameters. In some embodiments, stimulation indication window 240 includes one or more stimulation level indicators 242a to 242f For example, still referring to FIG. 2, stimulation indication window 240 may include a plurality of stimulation level indicators 242a, 242b, 242c, 242d, 242e, 242f. Each stimulation level indicator 242a-f may include a number or letter indicating an order of stimulation level indicators 242a-f. For example, each stimulation level indicator 242a-f may include a number or letter, and each stimulation level indicator 242a-f may be arranged in numerical or alphabetical order (e.g., stimulation level indicator 242a may be labeled with a "1," stimulation level indicator 242b may be labeled with a "2," etc.; stimulation level indicator 242f may be labeled with a "1," stimulation level indicator 242e may be leveled with a "2," etc.; stimulation level indicator 242a may be labeled with an "A," stimulation level indicator 242*b* may be labeled with a "B," etc.; or stimulation level indicator 242*f* may be labeled with an "A," stimulation level indicator 242*e* may be leveled with a "B," etc.). Although stimulation indication window 240 is shown in FIG. 2 as including six stimulation level indicators 242*a-f*, this is only one example. Stimulation indication window 240 may have any amount of stimulation level indicators 242*a-f* suitable for placement operations.

Each stimulation level indicator 242*a-f* of stimulation indication window 240 may represent a different value of a stimulation parameter. For example, each stimulation level indicator 242*a-f* may represent a different stimulation amplitude, stimulation pulse width, stimulation frequency, stimulation duration, stimulation charge, or electrode combination delivering stimulation. For example, stimulation level indicator 242*a* could represent stimulation with an amplitude of 1 milliampere (mA), stimulation level indicator 242*b* could represent stimulation with a charge of 3 mA, stimulation level indicator 242*c* could represent a stimulation with a charge of 5 mA, etc. As stimulations are delivered with varying stimulation parameters (e.g., stimulation delivered with increasing charge, stimulation delivered with increasing pulse width, stimulation delivered from different electrodes, etc.), the stimulation level indicator 242 which corresponds to the stimulation parameter delivered, may be highlighted, light up, change color, or otherwise indicated. Referring to the previous example, if stimulation level indicator 242*a* represents stimulation with a charge of 1 mA, stimulation level indicator 242*b* represents stimulation with a charge of 3 mA, and stimulation level indicator 242*c* represents a stimulation with a charge of 5 mA, then, as a 1 mA charge is delivered, stimulation level indicator 242*a* will become highlighted, light up, change color, or otherwise be indicated. As placement mode or another mode of operation progresses, a stimulation with a charge of 3 mA may be delivered and stimulation level indicator 242*b* may then become highlighted, light up, change color, or otherwise be indicated.

Still referring to FIG. 2, a user interface 120 (e.g., placement mode GUI 200) may include one or more phase buttons 250*a*, 250*b*, 250*c*. In some embodiments, each phase button 250*a-c* refers to a phase of operation. For example, phase button 250*a* may be labeled as "Placement Mode" and may correspond to placement mode, phase button 250*b* may be labeled as "Mapping Mode" and may correspond to mapping mode, and phase button 250*c* may be labeled "Therapy Mode" and may correspond to therapy mode. Referring to the previous example, when the LCU 100 is in placement mode, phase button 250*a* of placement mode GUI 200 may be highlighted, lit up, of a different color phase buttons 250*b* and 250*c*, or otherwise indicated.

Each phase button 250*a-c*, when selected, may cause the operation of LCU 100 to switch phases to the corresponding phase, or vice versa (operating in a particular mode switches highlighting, color indications, etc. of the corresponding phase button 250*a-c*). For example, for an LCU 100, operating in placement mode, when a user presses phase button 250*b*, the LCU 100 may switch operation from placement mode to mapping mode. When LCU 100 switches phases of operation, the phase button 250*a-c* corresponding to the new phase may be highlighted, lit up, of a different color than other phase buttons 250, or otherwise indicated. The switching of phases of operation, along with the switching of indicated phase button 250*a-c*, may, in some embodiments, be functionally similar to a tabbed operation, where each phase button 250*a-c* acts as a tab for its corresponding phase of operation. In some embodiments, each phase button 250*a-c* is inactive while operations are being performed. Stated another way, some operations of LCU 100 (e.g., operations that are a part of placement phase or mapping phase) may lock-out other phases of operation, or prevent a user from changing the phase of operation.

Still referring to FIG. 2, a user interface 120 (e.g., a placement mode GUI 200) may include one or more action buttons 260*a*, 260*b*, 260*c*, 260*d*, and 206*e*. The one or more action buttons 260 may allow a user to instruct the LCU 100 to begin, resume, pause, start, modify, or end one or more processes related to stimulation. In one or more embodiments, a user interface 120 (e.g., a placement mode GUI 200) may include one or more of: an "enable" action button, a "start" action button, a "response" action button, a "retry" action button, a "next" action button, a "stop" action button, a "completion" action button, an "end session" action button, or a combination thereof. Various types, combinations, and configurations of action buttons 260, according to one or more embodiments, are described below.

For example, a user interface 120 (e.g., a placement mode GUI 200) may include one or more action buttons 260*a-f* that enable a user to activate and/or deactivate the LCU 100 system and/or user interface 120 (e.g., an "enable" action button). For example, according to one or more embodiments, one or more action buttons 260*a-f* may function as an enabling toggle switch, that varies in one of two states. The two states may be represented by a color change, an accent, or other modification that indicates the switch (e.g., an "enable" action button) has changed states. In one state of the toggle switch, the LCU 100 system is able to deliver stimulation, and the user interface 120 (e.g., placement mode GUI 200) is able to accept commands. In the other state of the toggle switch, the LCU 100 system is not able to deliver stimulation and the user interface 120 is blocked or inactivated from receiving input (e.g., input other than the action button 260*a-f* functioning as the toggle switch).

According to one or more embodiments, a user interface 120 (e.g., a placement mode GUI 200) may include one or more action buttons 260*a-f* that allow a user to start the selected phase of operation (e.g., a "start" action button). As described in greater detail herein, each phase of operation (e.g., placement mode, mapping mode, or therapy mode) may include one or more associated processes. In some embodiments, a user interface 120 (e.g., a placement mode GUI 200) may guide a user through one or more processes related to stimulation, such as, for example, confirming placement of one or more stimulation arrays. In some embodiments, by pressing a "start" action button, one or more components of the LCU 100 (e.g., a user interface 120 and/or one or more stimulation arrays), may be triggered to begin one or more processes related to stimulation and/or begin guiding the user through one or more processes related to stimulation.

In some embodiments, a user interface 120 (e.g., a placement mode GUI 200) may include one or more action buttons 260*a-f* that allow a user to indicate whether a desired result of stimulation is occurring (e.g., a "response" action button). For example, one or more processes related to stimulation may require feedback from a user regarding whether a result of stimulation is occurring. In some embodiments, this result may be some type of indication that a nerve and/or a muscle is being stimulated. According to one or more embodiments, a user interface 120 (e.g., a placement mode GUI 200) may prompt a user to confirm a nerve and/or muscle is being stimulated, and the user may confirm the stimulation via a "response" action button. In some embodiments, a user interface 120 may have one action button 260*a-f* for an affirmative response and another action button 260*a-f* for a negative response. In other embodiments, a user interface 120 may include an action button 260*a-f* for affirmative responses only.

In some embodiments, a user interface 120 (e.g., a placement mode GUI 200) may include one or more action buttons 260*a-f* that allow a user to progress to a subsequent step of one or more processes related to stimulation (e.g., a "next" action button). As described above, one or more processes related to stimulation may include a user interface 120 (e.g., a placement mode GUI 200) prompting and/or guiding a user through a series of steps (e.g., instances where a user input is required). In some embodiments, a user interface 120 may include a "next" action button that allows a user to progress to a subsequent step of an ongoing process. In addition or alternatively, a "next" action button may allow a user to progress so a subsequent process of an ongoing phase of operation (e.g., placement mode, mapping mode, therapy mode).

According to one or more embodiments, a user interface 120 (e.g., a placement mode GUI 200) may include one or more action buttons 260*a-f* that allow a user to reiterate a previous step (e.g., a "retry" action button) of one or more processes related to stimulation. As described above, one or more processes related to stimulation may include a user interface 120 (e.g., a placement mode GUI 200) prompting and/or guiding a user through a series of steps (e.g., instances where a user input is required). A user may select the "retry" action button to repeat, redo, or reiterate a previous step or series of steps of a process. For example, one or more processes may include a stimulation delivered, and a prompt for the user to respond whether a nerve and/or muscle was stimulated. The user may select a "retry" action button to redo the stimulation. In some embodiments, a user can reiterate a process (e.g., a process of mapping mode) by pressing the "retry" action button.

In some embodiments, a user interface 120 (e.g., a placement mode GUI 200) may include one or more action buttons 260*a-f* that allow a user to end a phase of operation (e.g., a "completion" action button). A user may select a "completion" action button when a process or a sub-process of a phase of operation is complete, or the user is done with that process or sub-process. For example, selecting the "completion" action button may trigger one or more components of the LCU 100 (e.g., a user interface 120 or one or more stimulation arrays) to stop a current process or current step of a process. A user may select a "completion" action button even when the current process is incomplete or unsuccessfully completed. In some embodiments, a user selecting a "completion" action button when a current process is incomplete or unsuccessfully completed, will trigger a notification to the user.

According to one or more embodiments, a user interface 120 (e.g., a placement mode GUI 200) may include one or more action buttons 260*a-f* that allow a user to stop all processes being executed by LCU 100 (e.g., a "stop" action button). For example, when a user selects a "stop" action button, one or more components of LCU 100 (e.g., one or more stimulation arrays, user interface 120, system health monitor 160) may cease current operations. In some embodiments, one or more components of LCU 100 may finish their current operation or current step of a process before ceasing their operation. For example, for an LCU 100 operating in placement mode, one or more electrical pulses may be emitted from one or more stimulation arrays. In some embodiments, a user selecting a "stop" action button would cause the one or more stimulation arrays to cease transmitting electrical signals immediately. In other embodiments, a user selecting a "stop" action button would cause the one or more stimulation arrays to cease transmitting electrical signals after the current pulse. A "stop" action button may be configured to act as a type of safety enhancement switch which, when selected, cuts power to one or more components of an LCU 100 in contact with a patient.

In some embodiments, a user interface 120 (e.g., a placement mode GUI 200) may include one or more action buttons 260*a-f* (e.g., an "end session" action button) that allow a user to stop the current phase of operation and return to a previous screen of the user interface 120 (e.g., a main menu). For example, when a user selects an "end session" action button, one or more processes may terminate and the current phase of operation (e.g., placement mode, mapping mode, or therapy mode) may end. The selection of an "end session" action button may trigger the user interface 120 to display a menu or other splash page that allows a user to select a new phase of operation (e.g., placement mode, mapping mode, or therapy mode).

Referring now to FIG. 3, an exemplary user interface 120 for mapping mode is shown, e.g., a mapping mode GUI 300. Similar to placement mode GUI 200, mapping mode GUI 300 may be displayed on a touchscreen display, or other display means that allows for interactivity.

Mapping mode GUI 300 may include a status bar 305, a notification box 310, an anatomical indication window 330, one or more stimulation indication windows 340, 340', one or more progress bars 345, 345', one or more phase buttons 350*a-c*, one or more action buttons 360*a-g*. Status bar 305 may function similarly to status bar 205 of placement mode GUI 200. For example, status bar 305 may display information (e.g., via graphic, text, or a combination thereof) related to the operation of the LCU 100.

Similarly, notification box 310 may function similarly to notification box 210 of placement mode GUI 200. For example, notification box 310 may display information relating to operations of the LCU 100, such as, for example, a summary of stimulations recently delivered to a patient, instructions to a user, or a summary of parameters of stimulation. Text or graphic instructions within notification box 310 may include instructions for the user to use LCU 100 through the mapping mode phase of operations.

Anatomical indication window 330 may be functionally similar to anatomical indication window 230. For example, anatomical indication window 330 may display graphics or text indicative of one or more anatomical structures, delivered electrical stimulation, or electrical stimulation delivered to one or more anatomical structures. In one or more embodiments, anatomical indication window 330 may include one or more images or renderings of a patient, a single lung, a pair of lungs, a diaphragm, one or two hemi-diaphragms, one or more blood vessels (e.g., jugular vein, subclavian vein, superior vena cava, subclavian artery, aorta, carotid artery), one or more nerves (e.g., left phrenic nerve, right phrenic nerve, vagus nerve, one or more cervical nerves), one or more electrodes, one or more stimulation arrays, a catheter supporting one or more stimulation arrays, or a combination thereof. Anatomical indication window 330 may also include text indicative of one or more anatomical structures, delivered electrical stimulation, or electrical stimulation delivered to one or more anatomical structures, such as, for example, left and right side designations. Various parts of anatomical indication window 330 may light up, change color, or otherwise be indicated when stimulation is being applied to one or more afferents of the indicated part. For example, during mapping mode operations, during some processes, stimulation may be delivered to nerves and/or muscles that are connected or associated with the left lung while during other processes, stimulation may be delivered to nerves and/or muscles that are connected or associated with the right lung. During the delivery of stimulation to the anatomical structures associated with the left lung, a left lung part of anatomical indication window 330 and/or a left hemi-diaphragm may light up, change color, or otherwise be indicated. Similar indications may be made in anatomical indication window 330 to the right lung and/or right hemi-diaphragm parts when stimulation is delivered to anatomical structures associated with the right lung.

A mapping mode GUI 300 may include one or more stimulation indication windows (e.g., stimulation indication window 340 and stimulation indication window 340'). Each stimulation indication window 340, 340' may provide information to a user regarding one or more stimulation parameters. According to one or more embodiments, such as the one shown in FIG. 3, a first stimulation indication window 340 may correspond to a left side of a patient's anatomy, and a second stimulation indication window 340' may correspond to a right side of a patient's anatomy.

In some embodiments, each stimulation indication window 340, 340' includes one or more stimulation level indicators 342a-f, 342a'-f. For example, still referring to FIG. 3, stimulation indication window 340 may include a plurality of stimulation level indicators 342a-f, and stimulation indication window 340' may include a plurality of stimulation level indicators 342a'-f. Each stimulation indication window 340, 340' and its component stimulation level indicators 342a-f, 342a'-f may be functionally similar to stimulation indication window 240 and its component stimulation level indicators 242a-f of placement mode GUI 200. For example, each stimulation level indicator 342a-f, 342a'-f may include a number or letter and each stimulation level indicator 342a-f, 342a'-f may be arranged in numerical or alphabetical order within its stimulation indication window 340, 340' (e.g., stimulation level indicators 342a, 342a' may be labeled with a "1", stimulation level indicators 342b, 342b' may be labeled with a "2", etc.; stimulation level indicators 342f, 342f' may be labeled with a "1", stimulation level indicators 342e, 342e' may be labeled with a "2", etc.).

Although stimulation indication windows 340, 340' are shown in FIG. 3 as including six stimulation level indicators 342a-f, 342a'-f each, this is only one example. Each stimulation indication window 340, 340' may independently have any amount of stimulation level indicators 342a-f, 342a'-f, suitable for mapping. For example, stimulation indication window 340 may include six stimulation level indicators 342a-f and stimulation indication window 340' may include five stimulation level indications 342a'-e'.

Each stimulation level indicator 342 a-f, 342a'-f of each stimulation indication window 340, 340' may represent a different value of a stimulation parameter. For example, each stimulation level indicator 342a-f, 342a'-f may represent a different stimulation amplitude, stimulation pulse width, stimulation frequency, stimulation duration, stimulation charge, or electrode combination delivering stimulation. For example, stimulation level indicator 342a could represent stimulation from a most distal half of electrodes on one stimulation array, stimulation level indicator 342b could represent stimulation from a the most proximal half of electrodes on one stimulation array, stimulation level indicator 342c could represent stimulation from a medial third of electrodes on one stimulation array, stimulation level indicator 342a' could represent stimulation from a most distal half of electrodes on a second stimulation array, stimulation level indicator 342b' could represent stimulation from a most proximal half of electrodes on the second stimulation array, stimulation level indicator 342c' could represent stimulation from a medial third of electrodes on the second stimulation array, etc. As stimulations are delivered with varying stimulation parameters (e.g., stimulation delivered with increasing charge, stimulation delivered with increasing pulse width, stimulation delivered from different electrodes, etc.), the stimulation level indicator 342a-f, 342a'-f which corresponds to the stimulation parameter delivered, may be highlighted, light up, change color, or otherwise indicated.

Referring to the previous example, if stimulation level indicator 342a represents stimulation from a most distal half of electrodes on one stimulation array, stimulation level indicator 342b represents stimulation from a most proximal half of electrodes on one stimulation array, stimulation level indicator 342c represents stimulation from a medial third of electrodes on one stimulation array, then, as stimulation is delivered from the most distal half of electrodes on one stimulation array, stimulation level indicator 342a will become highlighted, light up, change color, or otherwise be indicated. As mapping mode or another mode of operation progresses, a stimulation may be delivered from the most proximal half of electrodes on the stimulation array, and stimulation level indicator 342b may then become highlighted, light up, change color, or otherwise be indicated.

A user interface 120 (e.g., a mapping mode GUI 300) may include one or more progress bars 345, 345'. Each progress bar 345, 345' may provide a textual or pictorial indication of the progress of one or more methods related to stimulation. For example, in one or more embodiments where stimulation indication window 340 corresponds to the left side of a patient's anatomy, progress bar 345 may indicate the overall progress of completing mapping operations (described in greater detail below) of the left side of a patient's anatomy. Similarly, where stimulation indication window 340' corresponds to the right side of a patient's anatomy, progress bar 345' may indicate the overall progress of completing mapping operations (described in greater detail below) of the right side of a patient's anatomy. In some embodiments, a progress bar 345, 345' may indicate the progress of one or more processes or sub-processes that are a part of mapping operations. Portions of a length of the progress bar 345, 345' may light up, or otherwise be indicated progressively. For example, a first portion of a length of progress bar 345, 345' may be lit up after a first process of mapping operations is complete, and a second portion of a length of the progress bar 345, 345', adjacent to the first portion of a length of the progress bar 345, 345' may be lit up after a second process of mapping operations is complete.

Still referring to FIG. 3, a user interface 120 (e.g., mapping mode GUI 300) may include one or more phase buttons 350a, 350b, 350c. Similar to phase buttons 250a-c of placement mode GUI 200, in some embodiments, each phase button 350a-c may refer to a phase of operation. For example, phase button 350a may be labeled as "Placement Mode" and may correspond to placement mode, phase button 350b may be labeled as "Mapping Mode" and may correspond to mapping mode, and phase button 350c may be labeled "Therapy Mode" and may correspond to therapy mode. Referring to the previous example, when in the LCU 100 is in mapping mode, phase button 350b of mapping mode GUI 300 may be highlighted, lit up, of a different color than phase buttons 350a and 350c, or otherwise indicated.

Each phase button 350a-c may be functionally similar to phase buttons 250a-c of placement mode GUI 200. For example, when selected, phase buttons 350*a-c* may cause the operation of LCU 100 to switch phases to the corresponding phase or vice versa (operating in a particular mode switches highlighting, color indications, etc. of the corresponding phase button 350*a-c*). For example, for an LCU 100, operating in mapping mode, when a user presses phase button 350*c*, the LCU 100 may switch operation from mapping mode to therapy mode. When LCU 100 switches phases of operation, the phase button 350*a-c* corresponding to the new phase may be highlighted, lit up, of a different color than other phase buttons 350*a-c*, or otherwise indicated.

Still referring to FIG. 3, a user interface 120 (e.g., a mapping mode GUI 300) may include one or more action buttons 360*a*, 360*b*, 360*c*, 360*d*, 360*e*, 360*f*, 360*g*. The one or more action buttons 360*a-g* may allow a user to instruct the LCU 100 to begin, resume, pause, start, modify, or end one or more processes related to stimulation. In one or more embodiments, a user interface 120 (e.g., a mapping mode GUI 300) may include one or more of: an "enable" action button, a "start" action button, a "response" action button, a "retry" action button, a "next" action button, a "stop" action button, a "completion" action button, an "end session" action button, or a combination thereof. The functions of various types of action buttons 360*a-g*, are described above in relation to action buttons 260*a-e* of placement mode GUI 200.

Referring now to FIG. 4, an exemplary user interface 120 for therapy mode is shown, e.g., a therapy mode GUI 400. Similar to placement mode GUI 200 and mapping mode GUI 300, therapy mode GUI 400 may be displayed on a touchscreen display, or other display means that allows for interactivity. In some embodiments, a user interface 120 may include placement mode GUI 200, mapping mode GUI 300, and therapy mode GUI 400.

Therapy mode GUI 400 may include a status bar 405, a notification box 410, an anatomical indication window 430, one or more stimulation intensity windows 441, 441' one or more stimulation intensity adjustment keys 442*a,b*, 442*a*', b', one or more therapy parameter windows 445*a-d*, one or more therapy parameter adjustment keys 446*a-d*, 446*a'-d'*, one or more phase buttons 450*a-c*, one or more action buttons 460*a-e*, one or more timed therapy status windows (e.g., delivered therapy status window 475 and scheduled therapy status window 470), or a combination thereof.

Still referring to FIG. 4, status bar 405 may function similarly to status bar 205 of placement mode GUI 200 or status bar 305 of mapping mode GUI 300. For example, status bar 405 may display information (e.g., via graphic, text, or a combination thereof) related to the operation of the LCU 100.

Further, notification box 410 may function similarly to notification box 210 of placement mode GUI 200 or notification box 310 of mapping mode GUI 300. For example, notification box 410 may display information relating to operations of the LCU 100, such as, for example, a summary of stimulations recently delivered to a patient, instructions to a user, or a summary of parameters of stimulation. Text or graphic instructions within notification box 410 may include instructions for the user to use LCU 100 through the therapy mode phase of operations.

Anatomical indication window 430 may be functionally similar to anatomical indication window 230 or anatomical indication window 330. For example, anatomical indication window 430 may display graphics or text indicative of one or more anatomical structures, delivered electrical stimulation, or electrical stimulation delivered to one or more anatomical structures. In one or more embodiments, anatomical indication window 430 may include one or more images of a patient, a single lung, a pair of lungs, a diaphragm, one or two hemi-diaphragms, one or more blood vessels (e.g., jugular vein, subclavian vein, superior vena cava, subclavian artery, aorta, carotid artery), one or more nerves (e.g., left phrenic nerve, right phrenic nerve, vagus nerve, one or more cervical nerves), one or more electrodes, one or more stimulation arrays, a catheter supporting one or more stimulation arrays, or a combination thereof. Anatomical indication window 430 may also include text indicative of one or more anatomical structures, delivered electrical stimulation, or electrical stimulation delivered to one or more anatomical structures, such as, for example, left and right side designations. Various parts of anatomical indication window 430 may light up, change color, or otherwise be indicated when stimulation is being applied to one or more afferents of the indicated part. For example, during therapy mode operations, stimulation may be delivered to nerves and/or muscles that are connected or associated with the left lung and/or the right lung. During the delivery of stimulation to the anatomical structures associated with the left lung and left hemi-diaphragm, a left lung part of anatomical indication window 430 and/or a left hemi-diaphragm may light up, change color, or otherwise be indicated. Similar indications may be made in anatomical indication window 430 to the right lung and/or right hemi-diaphragm parts when stimulation is delivered to anatomical structures associated with the right lung.

Still referring to FIG. 4, a therapy mode GUI 400 may include one or more stimulation intensity windows 441, 441'. Each stimulation intensity window 441, 441' may provide a numerical, textual, or pictorial indication of the stimulation intensity being delivered to one or more anatomical targets. For example, stimulation intensity window 441 may provide an indication of the stimulation intensity being delivered to one or more anatomical targets on the left side of the patient and stimulation intensity window 441' may provide an indication of the stimulation intensity being delivered to one or more anatomical targets on the right side of the patient. In some embodiments, a stimulation intensity window 441, 441' may display the charge of stimulation being delivered (e.g., an amplitude, a pulse width, a charge, or a percentage of the set fine threshold). In the example shown in FIG. 4, stimulation intensity window 441' indicates that 100% of the fine threshold is being delivered to one or more afferents of right-side respiratory structures, and stimulation intensity window 441 indicates that 95% of the fine threshold is being delivered to one or more afferents of left-side respiratory structures.

A therapy mode GUI 400 may also include one or more stimulation intensity adjustment keys 442*a,b*, 442*a*', b'. For example, the therapy mode GUI 400 may include one or more stimulation intensity adjustment keys 442*a,b*, 442*a*', b' that correspond to each stimulation intensity window 441, 441'. The stimulation adjustment keys 442*a,b*, 442*a*', b' may allow a user or other healthcare professional to adjust the intensity of stimulation being delivered. For example, stimulation intensity adjustment key 442*a* may increase the intensity of stimulation delivered to one or more muscles and/or nerves associated with left-side respiratory structures (e.g., increase the intensity to greater than 95% of the set fine threshold) and stimulation intensity adjustment key 442*b* may decrease the intensity of stimulation delivered to one or more muscles and/or nerves associated with left-side respiratory structures (e.g., decrease the intensity to less than 95% of the set fine threshold). Stimulation adjustment keys 442a' and 442b' may similar adjust the intensity of stimulation delivered to one or more muscles and/or nerves associated with right-side respiratory structures.

In addition to one or more stimulation intensity windows 441, 441', a therapy mode GUI 400 may include one or more therapy parameter windows 445a-d. Each therapy parameter window 445a, 445b, 445c, and 445d may display one or more properties related to delivered stimulation. For example, a therapy mode GUI 400 may include one or more therapy parameter windows 445a-d that display one or more of: stimulation amplitude, stimulation pulse width, stimulation frequency, pulse frequency, stimulation timing, number of stimulation pulses to be delivered in set a time interval, duration of time interval within which a set number of stimulation pulses are to be delivered.

A therapy mode GUI 400 may also include one or more therapy parameter adjustment keys 446a-d, 446a'-d'. For example, the therapy mode GUI 400 may include one or more therapy parameter adjustment keys 446a-d, 446a'-d' that correspond to each stimulation parameter window 445a-d. The therapy parameter adjustment keys 446a-d, 446a'-d' may allow a user or other healthcare profession to adjust the parameters of stimulation being delivered. For example, therapy parameter window 445a may described a number of stimulation pulses to be delivered in set a time interval. Therapy parameter adjustment key 446a may increase the number of stimulation pulses delivered to one or more muscles and/or nerves associated (e.g., increase the number to greater than 10) and therapy parameter adjustment key 446a' may decrease the number of stimulation pulses delivered to one or more muscles and/or nerves associated (e.g., decrease the number to less than 10). Stimulation adjustment keys 446b and 446b', 446c and 446c', 446d and 446d' may similarly adjust the parameters of stimulation indicated in the corresponding stimulation parameters windows 445b, 445c, and 445d.

Still referring to FIG. 4, a therapy mode GUI 400 may include one or more timed therapy status windows. For example, as described in greater detail below, a user or healthcare professional may program an LCU 100 in therapy mode to deliver a set number of stimulations over a given time interval. The user interface 120 (e.g., therapy mode GUI 400) may include one or more timed therapy status windows that indicate the status of the timed stimulation delivery. For example, therapy mode GUI 400 may include a delivered therapy status window 475 that displays or otherwise indicates how many stimulations have been delivered over the time interval. In some embodiments, therapy mode GUI 400 may also include a scheduled therapy status window 470 that indicates how many prescribed (e.g., programmed) stimulations have yet to be delivered.

Still referring to FIG. 4, a user interface 120 (e.g., therapy mode GUI 400) may include one or more phase buttons 450a, 450b, 450c). Similar to phase buttons 250 of placement mode GUI 200 and phase buttons 350 of mapping mode GUI 300, in some embodiments, each phase button 450 refers to a phase of operation. For example, phase button 450a may be labeled as "Placement Mode" and may correspond to placement mode, phase button 450b may be labeled as "Mapping Mode" and may correspond to mapping mode, and phase button 450c may be labeled "Therapy Mode" and may correspond to therapy mode. Referring to the previous example, when in the LCU 100 is in therapy mode, phase button 450c of therapy mode GUI 400 may be highlighted, lit up, of a different color than other phase buttons 450a and 450b, or otherwise indicated.

Each phase button 450 may be functionally similar to phase buttons 250 of placement mode GUI 200 or phase buttons 350 of mapping mode GUI 300. In some embodiments, when selected, a phase button 450 may cause the operation of LCU 100 to switch phases to the phase corresponding to the selected phase button 450. For example, for an LCU 100, operating in therapy mode, when a user presses phase button 450a, the LCU 100 may switch operation from therapy mode to placement mode. When LCU 100 switches phases of operation, the phase button 450 corresponding to the new phase may be highlighted, lit up, of a different color than other phase buttons 450, or otherwise indicated.

Still referring to FIG. 4, a user interface 120 (e.g., a therapy mode GUI 400) may include one or more action buttons 460 (e.g., action buttons 460a, 460b, 460c, 460d, 460e). The one or more action buttons 460 may allow a user to instruct the LCU 100 to begin, resume, pause, start, modify, or end one or more processes related to stimulation. In one or more embodiments, a user interface 120 (e.g., therapy mode GUI 400) may include one or more of: an "enable" action button, a "start" action button, a "response" action button, a "retry" action button, a "next" action button, a "stop" action button, a "completion" action button, an "end session" action button, or a combination thereof. The functions of various types of action buttons 460a-e, are described above in relation to action buttons 260a-e of placement mode GUI 200.

Placement Mode

An LCU 100 may be operated in placement mode, and, in some embodiments, a user may operate the LCU 100 through a placement mode GUI 200. Placement mode, may be used to confirm placement of one or more stimulation arrays. For example, a user or healthcare professional may place one or more stimulation arrays on or in a patient. A user may then initiate placement mode via, for example, selecting a phase button 250a-c corresponding to placement mode. In some embodiments, a user may navigate to a placement mode via one or more menus of a user interface 120. As described above, selection of a phase button 250a-c corresponding to placement mode may cause the user interface 120 to display a placement mode GUI 200. A user may then start one or more processes of placement mode by selecting an action button 260a-e of placement mode GUI 200.

In one or more embodiments, placement mode may include one or more processes for confirming placement of one or more stimulation arrays. After a user initiates placement mode (e.g., via an action button 260 of placement mode GUI 200), LCU 100 may induce one or more stimulation arrays to generate a stimulation pulse. For example, each electrode of one or more stimulation arrays may emit a stimulation pulse. In some embodiments, an LCU 100 may include multiple stimulation arrays (e.g., a stimulation array of electrodes), but less than the full complement of stimulation arrays may be used in placement mode (e.g., an LCU 100 may include a distal stimulation array and a proximal stimulation array, and may only use the proximal stimulation array in placement mode). Generally, one or more stimulation arrays (e.g., each electrode of one or more stimulation arrays) may generate stimulation pulses of increasing charge until the LCU 100 (e.g., via system health monitor 160) or a user detects that a nerve, muscle, or other anatomical stimulation target has been stimulated. Pulses emitted from various electrodes (or electrode combinations), each pulse having the same charge, may be referred to as an electrode sweep. In some embodiments, an electrode sweep includes each electrode of the one or more stimulation arrays emitting a stimulation, where each stimulation has the same charge.

As described previously, LCU 100 may detect stimulation of an anatomical target (via, e.g., one or more sensors in communication with system health monitor 160). Alternatively or in addition, a user may detect stimulation of an anatomical target (e.g., based on a physical response or appearance of a patient) and indicate via one or more action buttons 260*a*-*e* of a user interface 120 (e.g., placement mode GUI 200) that stimulation occurred. A user may also indicate that stimulation of the anatomical target did not occur (e.g., was not detected) via one or more action buttons 260*a*-*e* (e.g., a "response" action button or a "next" action button). If stimulation of an anatomical target cannot be detected during an electrode sweep, LCU 100 may increase the charge of the electrode sweep. In placement mode, like other operations of LCU 100, the LCU 100 may end the process (and/or prevent stimulation from being delivered) if a pre-determined maximum charge is exceeded. The pre-determined maximum charge may be set by the LCU 100 manufacturer or a user of the LCU 100. If stimulation of the anatomical target cannot be detected without exceeding the pre-determined maximum charge, then placement has failed. If placement fails, the user may adjust the position of one or more stimulation arrays in relation to the patient and/or retry placement mode operations.

Figure 5:
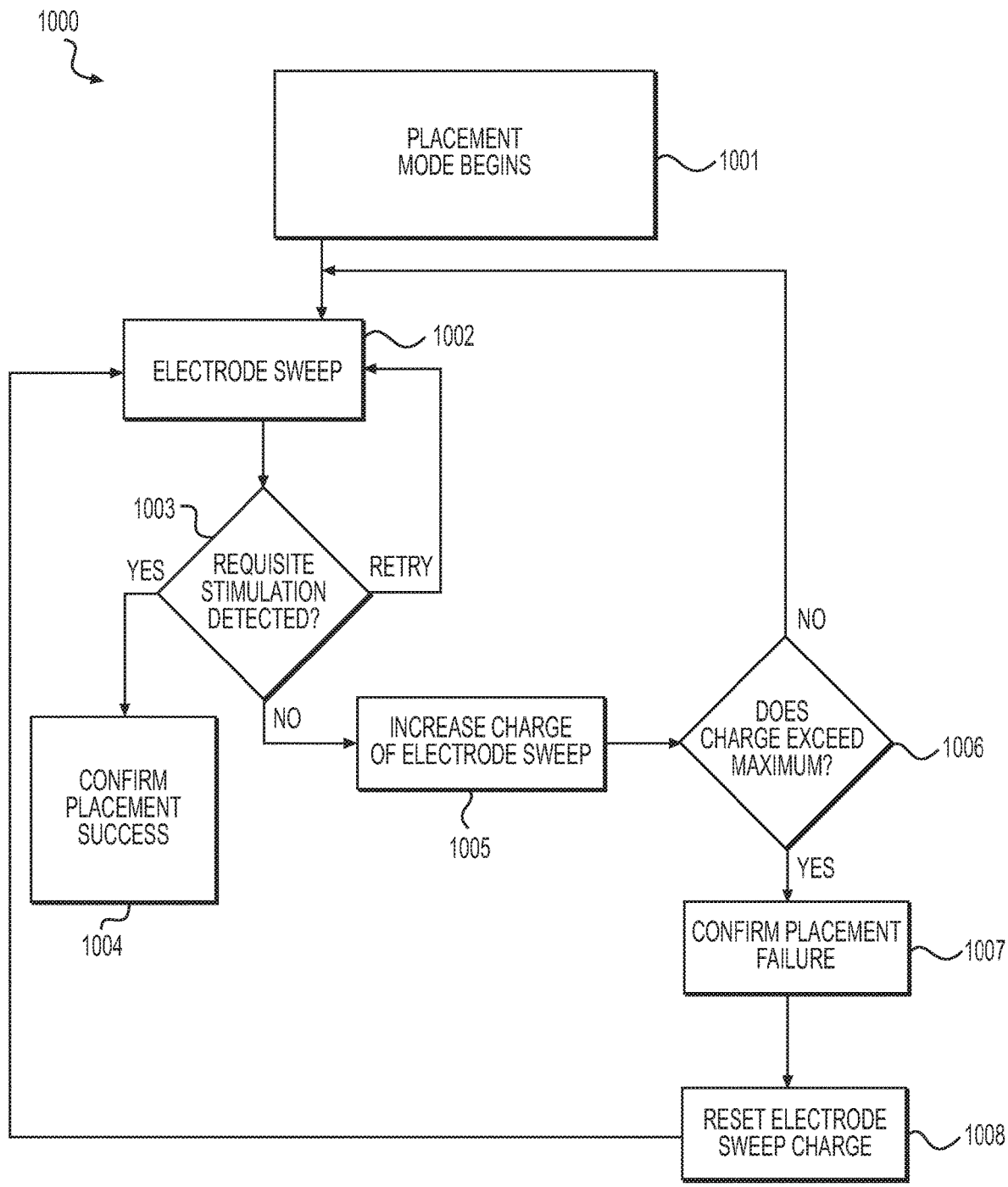
FIG. 5 is a flowchart of a method according to an embodiment of the present disclosure.

FIG. 5 shows an exemplary flow of a placement mode of an LCU 100, according to one or more embodiments. In the exemplary placement mode method 1000 shown in FIG. 5, diamond regions (e.g., steps 1003 and 1006) represent decision points (e.g., a decision by the LCU 100 or a user) while rectangular regions (e.g., steps 1001, 1002, 1004, 1005, 1007, 1008) represent other inflection or action/step points of the method. One or more components of placement mode GUI 200 (e.g., notification box 210) may provide instructions or other guidance for the user, to guide the user through one or more methods of placement mode, for example, placement mode method 1000.

Still referring to FIG. 5, a placement mode method 1000 may begin based on an input from a user via user interface 120, for example, a placement mode GUI 200 (step 1001). LCU 100 may then perform an electrode sweep using a plurality of electrodes (e.g., one or more electrode groups) of one or more stimulation arrays (step 1002). As described above, one or more indications may be made in anatomical indication window 230 that indicate stimulation is being delivered and/or one or more targets of delivered stimulation. For example, the stimulation may target afferents of one or more lung-accessories (e.g., nerves or muscles associated with lung movement, such as, for example, a phrenic nerve, a diaphragm, or a respiratory accessory muscle) and anatomical indication window 230 may include an indication that one or more lung-accessories is being stimulated (e.g., one or more lung or diaphragm pictograms may be indicated). One or more stimulation level indicators 242*a*-*f* of stimulation indication window 240 may also be indicated as stimulation is delivered. In some embodiments, more stimulation level indicators 242*a*-*f* are indicated as the charge of the electrode sweep is increased. For example, in an initial electrode sweep, only stimulation level indicator 242*a* of stimulation indication window 240 may be indicated. Each time the charge of the electrode sweep is increased, another stimulation level indicator 242*a*-*f* of stimulation indication window 240 (e.g., stimulation level indicator 242*b*) may be indicated. Once placement is confirmed, the most recently indicated stimulation level indicator 242*a*-*f* (e.g., stimulation level indicator 242*c*) may be indicated in a different manner (a different color, intensity, font, etc.), as to signal at what level of stimulation the requisite stimulation of one or more anatomical targets was achieved.

Referring again to FIG. 5, after an LCU 100 performs an electrode sweep, it may receive input on whether the requisite stimulation of anatomical target occurred (step 1003). As used herein, requisite stimulation may refer to a stimulation sufficient to cause a desired physiological result. In some embodiments, requisite stimulation for placement mode may include stimulation sufficient to cause contraction of a diaphragm or other lung-accessory. LCU 100 may receive input on whether the requisite stimulation of anatomical target occurred from one or more sensors in contact with the patient and in communication with system health monitor 160. In other embodiments, LCU 100 may receive input on whether the requisite stimulation of anatomical target occurred from a user (e.g., via a user interface 120, such as, for example, a placement mode GUI 200). In some embodiments, a user may indicate requisite stimulation of an anatomical target occurred via one or more action buttons 260*a*-*e* (e.g., a "response" action button or a "next" action button). In some embodiments, a user may select a "retry" action button which may induce the LCU 100 to repeat the most recent electrode sweep at the current charge level (step 1002). If an LCU 100 receives input that a requisite stimulation of an anatomical target was not detected, it may increase the charge of the electrode sweep (step 1005). If LCU 100 receives input that a requisite stimulation of an anatomical target was detected, it may progress to confirming placement success (step 1004). Confirmation of placement success may include displaying a notification to the user (e.g., a pop-up window or via notification box 210, anatomical indication window 230, or stimulation indication window 240) that one or more stimulation arrays are correctly placed.

Still referring to FIG. 5, after the charge of the electrode sweep is increased (step 1005), the LCU 100 may determine whether the charge of the electrode sweep exceeds the pre-determined maximum charge (step 1006). If the charge of the electrode sweep does not exceed the pre-determined maximum charge, LCU 100 may proceed with the next electrode sweep (step 1002). If, LCU 100 determines the charge of the electrode sweep would exceed the pre-determined maximum charge (step 1006), then the LCU 100 may confirm placement failure (step 1007). Confirmation of placement failure may include displaying a notification to the user (e.g., a pop-up window or via notification box 210) that placement has failed. Such a notification may instruct a user to alter placement of one or more stimulation arrays relative to the patient. After placement fails, LCU 100 may reset the electrode sweep charge to the charge level of the initial electrode sweep (e.g., the charge associated with stimulation level indicator 242*a*) or another charge level below the pre-determined maximum charge (step 1008). After the electrode sweep charge is reset, a user may have an option to retry one or more methods of placement mode. For example, a user may be able to, via one or more action buttons 260*a*-*e* of placement mode GUI 200, retry method 1000 of placement mode after repositioning one or more stimulation arrays.

An electrode sweep may include, for example, an electrical signal emitted from one or more of: each electrode of LCU 100, each electrode associated with one or more stimulation arrays, each electrode in a group of electrodes, a representative set of electrodes of a group of electrodes, a domain of electrode combinations, or a set of electrode combinations selected from the domain of electrode combinations. In some embodiments, a starting electrode sweep of a placement mode method 1000 may be delivered (e.g., delivered from each electrode or electrode combination involved in the electrode sweep) with a current of approximately 0.5 mA to approximately 3 mA and a pulse width of approximately 100 microseconds (μs) to approximately 1 millisecond (ms). For example, a starting electrode sweep of placement mode method 1000 may be delivered with a current of 0.5 mA, 0.7 mA, 1.0 mA, 1.5 mA, 2.0 mA, 2.5 mA, or 3.0 mA. Further, a starting electrode sweep of placement mode method 1000 may be delivered with at a pulse width of 100 μs, 125 μs, 150 μs, 175 μs, 200 μs, 225 μs, 250 μs, 275 μs, 300 μs, 350 μs, 400 μs, 450 μs, 500 μs, 600 μs, 700 μs, 800 μs, 900 μs, or 1 ms. According to one or more embodiments, for each electrode sweep, each electrode involved in the electrode sweep emits a stimulation with the programmed charge in series (e.g., consecutively, not concurrently). Each electrode sweep may have a duration of approximately 0.1 ms to approximately 2.0 s, such as, for example, 0.1 ms, 0.2 ms, 0.5 ms, 1.0 ms, 5.0 ms, 10 ms, 15 ms, 20 ms, 25 ms, 40 ms, 50 ms, 60 ms, 75 ms, 90 ms, 0.1 s, 0.3 s, 0.5 s, 0.7 s, 0.9 s, 1.0 s, 1.25 s, 1.50 s, 1.75 s, or 2.0 s.

Each increase in electrode sweep charge may be at a consistent, constant interval, inconsistent, differing intervals, variable intervals, or arbitrary increments, and may occur as an increase in amplitude and/or an increase in pulse width. For example, each increase in electrode sweep charge may include an amplitude increase of approximately 0.5 mA to approximately 5 mA, such as, for example, 0.5 mA, 1.0 mA, 1.5 mA, 2.0 mA, 2.5 mA, 3.0 mA, 3.5 mA, 4.0 mA, 4.5 mA, or 5.0 mA. In some embodiments, an increase in electrode sweep charge includes an increase in pulse width, such as, for example, 25 μs, 50 μs, 75 μs, 100 μs, 125 μs, 150 μs, 175 μs, 200 μs, A manufacturer or user of LCU 100 may set a pre-determined maximum charge. A pre-determined maximum charge for one phase of operation (e.g., placement mode) may be different than a pre-determined maximum charge for another phase of operation (e.g., mapping mode). For example, LCU 100 may be programmed in terms of maximum current, maximum pulse width, maximum charge, or a combination thereof. In some embodiments, a pre-determined maximum charge (e.g., a pre-determined maximum charge for placement mode) may include a maximum current of approximately 3 mA to approximately 20 mA, such as, for example, 3 mA, 5 mA, 7 mA, 10 mA, 13.5 mA, 17 mA, or 20 mA; a maximum pulse width of approximately 300 μs to approximately 1 ms, such as, for example, 300 μs, 500 μs, 750 μs, or 1 ms; and/or a maximum charge of approximately 1.0 microCoulombs (μC) to approximately 20 μC, such as, for example 1.0 μC, 5 μC, 10 μC, 15 μC, or 20 μC.

Mapping Mode

In mapping mode, the application controller may iteratively deliver stimulation to the electrode combinations of a catheter (e.g., an intravenous catheter) or other stimulation delivery system. The application controller may further request user feedback in order to identify suitable stimulation parameters (e.g., left electrode combination, right electrode combination, threshold current) for therapy. In other embodiments, the application controller may receive feedback from sensors including, for example, sensors configured to monitor airway pressure, airway flowrate, tidal volume, transpulmonary pressure, blood gas levels (e.g., blood $O_2$ levels or blood $CO_2$ levels), heart rate, breathing rate and timing, impedance (e.g., sensors configured for electrical impedance tomography), lung gas distribution electromyographic activity, or transdiaphragmatic pressure, via system health monitor 160. In another embodiment, the application controller may receive feedback from another medical device such as a mechanical ventilator, respiratory support device, extra-corporeal membrane oxygenation (ECMO) system, heart rate or respiratory monitor, etc., for example, via system health monitor 160. The LCU 100 may deliver a limited number of pulses to various combinations of portions of a stimulation array (e.g. electrode combinations) on the stimulation device (e.g. catheter). When an electrode combination in proximity to a nerve (such as, for example, a phrenic nerve) is activated, it causes brief contractions (e.g., twitches) of a subject's muscle (such as, for example, a diaphragm). As described herein, one or more components of LCU 100 (e.g., user interface 120) may interactively guide a user to activate mapping phase and gather feedback in order to identify suitable electrode combinations, threshold charges, or both, for use in therapy mode.

Figure 6:
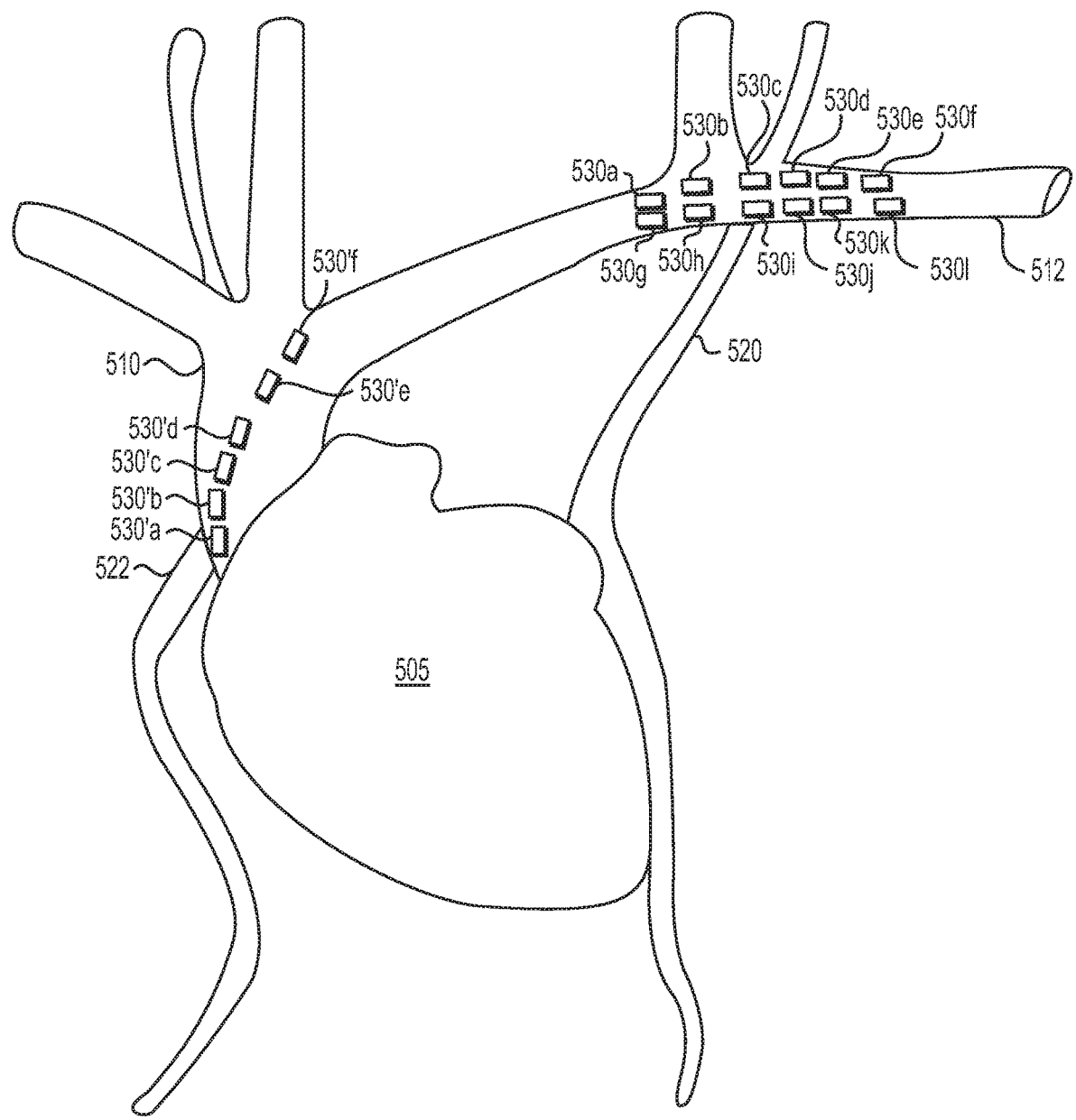
FIG. 6 illustrates the anatomy of selected tissues and anatomical lumens in a patient, along with an exemplary electrode array placed according to one or more embodiments of the present disclosure.

One exemplary arrangement of stimulation arrays and anatomical targets is shown in FIG. 6. Although FIG. 6 shows a suitable arrangement of one or more stimulation arrays, including at least 18 electrodes positioned in two groups, in relation to various anatomical structures, it is merely one example for the purposes of illustrating the function of an LCU 100 operating in mapping mode. Any suitable configuration of one or more stimulation arrays, such that electrodes are in proximity to nerves and/or muscles associated with breathing, may be used with the systems and methods described herein. For example, embodiments of the present disclosure may be used in combination with one or more systems, catheters, apparatuses, and electrodes described in U.S. Pat. Nos. 9,242,088, 9,333,363, 9,776,005, and/or 10,039,920; the disclosures of which are hereby incorporated by reference.

FIG. 6 shows parts of a circulatory system, including a left subclavian vein 512, a superior vena cava 510, and a heart 505. These parts of the circulatory system may be proximate to one or more nerves, such as, for example, a left phrenic nerve 520 and a right phrenic nerve 522. In some embodiments, one or more stimulation arrays may be placed in or near vasculature (e.g., a part of the circulatory system) and/or proximate to one or more nerves (e.g., a left phrenic nerve 520 and a right phrenic nerve 522). The one or more stimulation arrays may include one or more electrode groups, where each group of electrodes is configured to be placed near an anatomical stimulation target. For example, as shown in FIG. 6, a first group of electrodes 530a-1 may be positioned proximate a left phrenic nerve 520, and a second group of electrodes 530'a-f may be positioned proximate a right phrenic nerve 522. Each electrode group may include one or more electrodes (e.g., the second group of electrodes 530' shown in FIG. 6 includes electrodes 530'a, 530'b, 530'c, 530'd, 530'e, and 530'f). Various parts shown in FIG. 6 and their reference numerals may be referred to in the discussion below. For example, parts of FIG. 6 may be referred to in relation to processes of an LCU 100 in mapping mode, and the methods shown in FIGS. 7-9. However, it should be understood that this is merely one exemplary arrangement of electrodes and anatomical stimulation targets, and that the methods described below may be used in conjunction with any arrangement of stimulation arrays near anatomical stimulation targets.

In one or more embodiments, a mapping mode may include one or more processes for selecting, identifying, and/or determining one or more stimulation parameters (e.g., determining one or more stimulation parameters that will be used in therapy mode). For example, processes of mapping mode may determine a threshold charge (e.g., an amplitude, pulse width, or both) of stimulation and which electrode 530a-1, 530'a-f or electrode combination to use to deliver stimulation (e.g., deliver stimulation during therapy mode).

In at least one embodiment, a mapping mode may include at least three general processes: (1) coarse threshold assessment, (2) electrode identification, and (3) fine threshold assessment. In embodiments where one or more stimulation arrays include more than one group of electrodes, these processes may be performed for each group of electrodes. For example, a mapping mode for an LCU 100 including at least two groups of electrodes may include: (1) a first coarse threshold assessment (e.g., including a left electrode sweep), (2) a second coarse threshold assessment (e.g., including a right electrode sweep), (3) a first electrode identification, (4) a first fine threshold identification, (5) a second electrode identification, and (6) a second fine threshold identification. In some embodiments, the first group of electrodes and associated processes of a mapping mode (e.g., a first coarse threshold assessment, a first electrode identification, and a first fine threshold identification) may be associated with a left-most anatomical target (e.g., a proximal anatomical target), where the second group of electrodes and associated processes of a mapping mode (e.g., a second coarse threshold assessment, a second electrode identification, and a second fine threshold identification) may be associated with a right-most anatomical target (e.g, a distal anatomical target). References to a first process or a second process are explanatory and not meant to denote a preferred order of operation. In some embodiments, an electrode group near a right-most anatomical target may be used in one or more processes of mapping mode before an electrode group near a left-most anatomical target are used in one or more processes of mapping mode.

In some embodiments, a device or system configured for a mapping mode may proceed through each of the three general processes in the sequential order described herein (e.g., coarse threshold assessment, electrode identification, and fine threshold assessment). In other embodiments, a device or system configured for a mapping mode may proceed through all three general processes in a different order. In still other embodiments, one or more processes may be performed without performing the other processes of a mapping mode (e.g., performing either all stages corresponding to the left side, all stages corresponding to the right side, all stages corresponding to electrode identification, or all stages corresponding to threshold identification).

As described previously, electrodes 530a-1, 530'a-f may represent electrodes or electrode combinations for monopolar, bipolar, or tripolar electrical stimulation. As used herein, a stimulation being transmitted by an electrode 530a-1, 530'a-f may refer to an electrical signal being transmitted by a single electrode on the catheter to a ground reference that is at a distance from the anode to generate the large electrical field (monopolar electrical stimulation), an electrical signal being transmitted from a anode electrode to cathode electrode on the catheter (bipolar electrical stimulation), or an electrical signal being transmitted from one or more electrodes to one or more other electrodes (multipolar electrical stimulation) (e.g., from a cathode to two anodes, from two cathodes to an anode, or from a cathode to three or more anodes). As any of these electrode combinations and configurations are contemplated, for clarity when referring to one or more processes of mapping mode operations, such types of electrical signal transmission may all be referred to as a stimulation being transmitted by an electrode combination. For example, referring to FIG. 6, in some embodiments, a process of mapping mode may include a stimulation delivered between electrode 530c and 530i. In describing one or more processes of mapping mode below, this may be referred to as a stimulation delivered by electrode 530c or a stimulation delivered by electrode combination 530c and 530i.

In a coarse threshold assessment process (e.g., a process including a left electrode sweep or a right electrode sweep), a series of stimulations are repeated with different amplitudes, pulse widths, or charges to determine a coarse threshold of a level of stimulation suitable or desired for therapy. In some embodiments, a coarse threshold assessment may be performed for each group of electrodes 530a-1, 530'a-f of the one or more stimulation arrays. For example, a first coarse threshold assessment for the first group of electrodes 530a-1, proximate a left phrenic nerve 520; and a second coarse threshold assessment for the second group of electrodes 530'a-f, proximate a right phrenic nerve 522.

A user may then initiate mapping mode via, for example, selecting a phase button 250, 350, 450 corresponding to mapping mode. In some embodiments, a user may navigate to mapping mode via one or more menus of a user interface 120. As described above, selection of a phase button 250, 350, 450 corresponding to mapping mode may cause the user interface 120 to display a mapping mode GUI 300. A user may then start one or more processes of mapping mode by selecting an action button 360 of mapping mode GUI 300.

After a user initiates mapping mode (e.g., via an action button 360a-g of mapping mode GUI 300), LCU 100 may guide a user through one or more processes of mapping mode, such as for example, one or more coarse threshold assessments, one or more electrode identification (e.g., one or more electrode combination identifications), and/or one or more fine threshold identification (e.g., of a level of stimulation suitable or desired for therapy).

Figure 7:
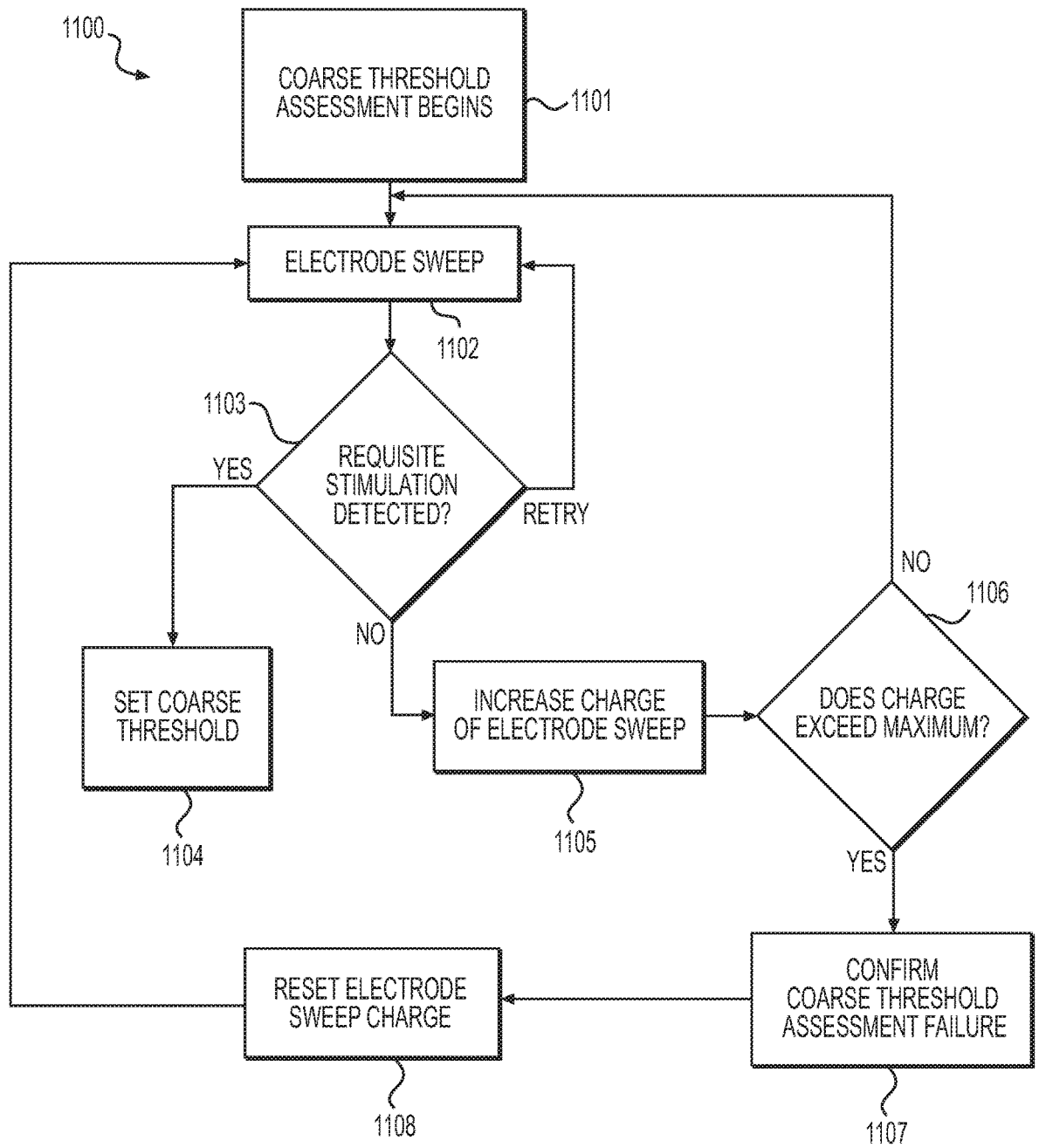
FIG. 7 is a flowchart of a method according to an embodiment of the present disclosure.

FIG. 7 shows an exemplary flow of a coarse threshold assessment process of mapping mode of an LCU 100, according to one or more embodiments. In the exemplary mapping mode coarse threshold assessment process 1100 shown in FIG. 7, diamond regions (e.g., steps 1103 and 1106) represent decision points (e.g., a decision by the LCU 100 or a user) while rectangular regions (e.g., steps 1101, 1102, 1104, 1105, 1107, 1108) represent other inflection or action/step points of the method. One or more components of mapping mode GUI 300 (e.g., notification box 310) may provide instructions or other guidance for the user, to guide the user through one or more methods or processes of mapping mode, for example, coarse threshold process 1100, electrode identification process 1200, or fine threshold process 1300.

Still referring to FIG. 7, a mapping mode process, such as, for example, coarse threshold assessment process 1100 may begin based on an input from a user via user interface 120, for example, a mapping mode GUI 300 (step 1101). LCU 100 may then perform an electrode sweep using a plurality of electrodes disposed on one or more stimulation arrays (step 1102). As described above, one or more indications may be made in anatomical indication window 330 that indicate stimulation is being delivered and/or indicate one or more targets of delivered stimulation. For example, the stimulation may target afferents of one or more lung-accessories (e.g., nerves or muscles associated with lung movement, such as, for example, a left phrenic nerve 520, a right phrenic nerve 522, a diaphragm, or a respiratory accessory muscle) and anatomical indication window 330 may include an indication that one or more lung-accessories is being stimulated (e.g., one or more lung or diaphragm pictograms may be indicated). One or more stimulation level indicators 342a-f, 342a'-f' of stimulation indication window 340, 340' may also be indicated as stimulation is delivered. In some embodiments, more stimulation level indicators 342a-f, 342a'-f' are indicated as the charge of the electrode sweep is increased. For example, in an initial electrode sweep, only stimulation level indicator 342a of stimulation indication window 340 may be indicated. Each time the charge of the electrode sweep is increased, another stimulation level indicator 342a-f, 342a'-f' of stimulation indication window 340, 340' (e.g., stimulation level indicator 342b) may be indicated.

As alluded to above, an electrode sweep may include, for example, an electrical signal emitted from each electrode of LCU 100, an electrical signal emitted from each electrode associated with one or more stimulation arrays, an electrical signal emitted from each electrode in a group of electrodes, an electrical signal emitted from a representative set of electrodes of a group of electrodes, an electrical signal emitted from a domain of electrode combinations, or an electrical signal emitted from a set of electrode combinations selected from the domain of electrode combinations. In some embodiments, a starting electrode sweep of a coarse threshold assessment process 1100 may be delivered (e.g., delivered from each electrode or electrode combination involved in the electrode sweep) with a current of approximately 0.5 mA to approximately 3 mA and a pulse width of approximately 100 microseconds (µs) to approximately 1 millisecond (ms). For example, a starting electrode sweep of coarse threshold assessment process 1100 may be delivered with a current of 0.5 mA, 0.7 mA, 1.0 mA, 1.5 mA, 2.0 mA, 2.5 mA, or 3.0 mA. By way of further example, a starting electrode sweep of coarse threshold assessment process 1100 may be delivered with at a pulse width of 100 µs, 125 µs, 150 µs, 175 µs, 200 µs, 225 µs, 250 µs, 275 µs, 300 µs, 350 µs, 400 µs, 450 µs, 500 µs, 600 µs, 700 µs, 800 µs, 900 µs, or 1 ms. Each electrode sweep may have a duration of approximately 0.1 ms to approximately 2.0 s, such as, for example, 0.1 ms, 0.2 ms, 0.5 ms, 1.0 ms, 5.0 ms, 10 ms, 15 ms, 20 ms, 25 ms, 40 ms, 50 ms, 60 ms, 75 ms, 90 ms, 0.1 s, 0.3 s, 0.5 s, 0.7 s, 0.9 s, 1.0 s, 1.25 s, 1.50 s, 1.75 s, or 2.0 s.

Each increase in electrode sweep charge may be at a consistent, constant interval, inconsistent, differing intervals, variable intervals, or arbitrary increments, and may occur as an increase in amplitude and/or an increase in pulse width. For example, each increase in electrode sweep charge may include an amplitude increase of approximately 0.5 mA to approximately 5 mA, such as, for example, 0.5 mA, 1.0 mA, 1.5 mA, 2.0 mA, 2.5 mA, 3.0 mA, 3.5 mA, 4.0 mA, 4.5 mA, or 5.0 mA. In some embodiments, an increase in electrode sweep charge includes an increase in pulse width, such as, for example, 25 µs, 50 µs, 75 µs, 100 µs, 125 µs, 150 µs, 175 µs, 200 µs.

In some embodiments, such as embodiments where one or more stimulation arrays include a plurality of groups of electrodes, stimulation indication window 340 (e.g., including stimulation level indicators 342a-f) may correspond to methods, processes, and stimulations associated with a left-most, or most proximal, anatomical stimulation target or group of electrodes; and stimulation indication window 340' (e.g., including stimulation level indicators 342a'-f) may correspond to methods, processes, and stimulations associated with a right-most, or most distal, anatomical stimulation target or group of electrodes.

Once a process of mapping mode is completed, such as, for example, a coarse threshold is confirmed, an electrode 530 (or electrode combination) is identified, or a fine threshold is confirmed, the most recently indicated stimulation level indicator 342 (e.g., stimulation level indicator 342c') may be indicated in a different manner, as to signal at what level of stimulation the requisite stimulation of one or more anatomical targets was achieved.

In mapping mode, like other operations of LCU 100, the LCU 100 may end the current process (and/or prevent stimulation from being delivered) if a pre-determined maximum charge is exceeded. The pre-determined maximum charge may be set by the LCU 100 manufacturer or a user of the LCU 100. If requisite stimulation of the anatomical target cannot be detected without exceeding the pre-determined maximum charge, then mapping has failed. If mapping fails, the user may adjust one or more stimulation arrays in relation to the patient, retry placement mode operations, and/or retry mapping mode operations.

Referring again to FIG. 7, after an LCU 100 performs an electrode sweep, it may receive input on whether the requisite stimulation of anatomical target occurred (step 1103). As noted above, requisite stimulation may refer to a stimulation sufficient to cause a desired physiological result. In some embodiments, requisite stimulation for mapping mode may include stimulation sufficient to cause contraction of a diaphragm or other lung-accessory. LCU 100 may receive input on whether the requisite stimulation of anatomical target occurred from one or more sensors in contact with the patient and in communication with system health monitor 160. In other embodiments, LCU 100 may receive input on whether the requisite stimulation of anatomical target occurred from a user (e.g., via a user interface 120, such as, for example, a mapping mode GUI 300). In some embodiments, a user may indicate requisite stimulation of an anatomical target occurred via one or more action buttons 360a-g (e.g., a "response" action button or a "next" action button). In some embodiments, a user may select a "retry" action button which may induce the LCU 100 to repeat the most recent electrode sweep at the current charge level (step 1102).

If an LCU 100 receives input that a requisite stimulation of an anatomical target was not detected, it may increase the charge of the electrode sweep (step 1105). If LCU 100 receives input that a requisite stimulation of an anatomical target was detected, it may progress to setting the coarse threshold and/or confirming a coarse threshold assessment (step 1104). Confirmation of a coarse threshold assessment may include displaying a notification to the user (e.g., a pop-up window or via notification box 310, anatomical indication window 330, or stimulation indication window 340) that a coarse threshold was identified. Further, setting coarse threshold may include saving information regarding a coarse threshold for use in one or more other processes or modes.

Still referring to FIG. 7, after the charge of the electrode sweep is increased (e.g., the amplitude and/or pulse width of the component stimulation pulses of the sweep are increased) (step 1105), the LCU 100 may determine whether the charge of the electrode sweep exceeds the pre-determined maximum charge (step 1106).

If the charge of the electrode sweep does not exceed the pre-determined maximum charge, LCU 100 may proceed with the next electrode sweep (step 1102). If LCU 100 determines the charge of the electrode sweep exceeds the pre-determined maximum charge (step 1106), then the LCU 100 may confirm coarse threshold assessment failure (step 1107). Confirmation of coarse threshold assessment failure may include displaying a notification to the user (e.g., a pop-up window or via notification box 310, anatomical indication window 330) that coarse threshold assessment has failed. Such a notification may instruct a user to alter placement of one or more stimulation arrays relative to the patient, reperform one or more processes of placement mode, and/or retry coarse threshold assessment (e.g., coarse threshold assessment process 1100). After coarse threshold assessment fails, LCU 100 may reset the electrode sweep charge to the charge level of the initial electrode sweep (e.g., the charge associated with stimulation level indicator 342*a*) or another charge level below the pre-determined maximum charge (step 1108). After the electrode sweep charge is reset, a user may have an option to retry one or more methods or processes of mapping mode. For example, a user may be able to, via one or more action buttons 360 of mapping mode GUI 300, retry process 1100 of mapping mode.

A manufacturer or user of LCU 100 may set a pre-determined maximum charge. As explained above, a pre-determined maximum charge for one phase of operation (e.g., mapping mode) may be different than a pre-determined maximum charge for another phase of operation (e.g., therapy mode). For example, LCU 100 may be programmed in terms of maximum current, maximum pulse width, maximum charge, or a combination thereof. In some embodiments, a pre-determined maximum charge (e.g., a pre-determined maximum charge for mapping mode) may include a current of approximately 3 mA to approximately 20 mA, such as, for example, 3 mA, 5 mA, 7 mA, 10 mA, 13.5 mA, 17 mA, or 20 mA; a pulse width of approximately 300 µs to approximately 1 ms, such as, for example, 300 µs, 500 µs, 750 µs, or 1 ms; and/or a charge of 1.0 microCoulombs (µC) to 20 µC, such as, for example 1.0 µC, 5 µC, 10 µC, 15 µC, or 20 µC.

In some embodiments, after a coarse threshold is set (e.g., step 1104 of exemplary coarse threshold assessment process 1100), an LCU 100 or a user operating an LCU 100, may initiate one or more processes for electrode identification. For example, a user may initiate a process for electrode identification via one or more action buttons 360 of a mapping mode GUI 300.

Figure 8:
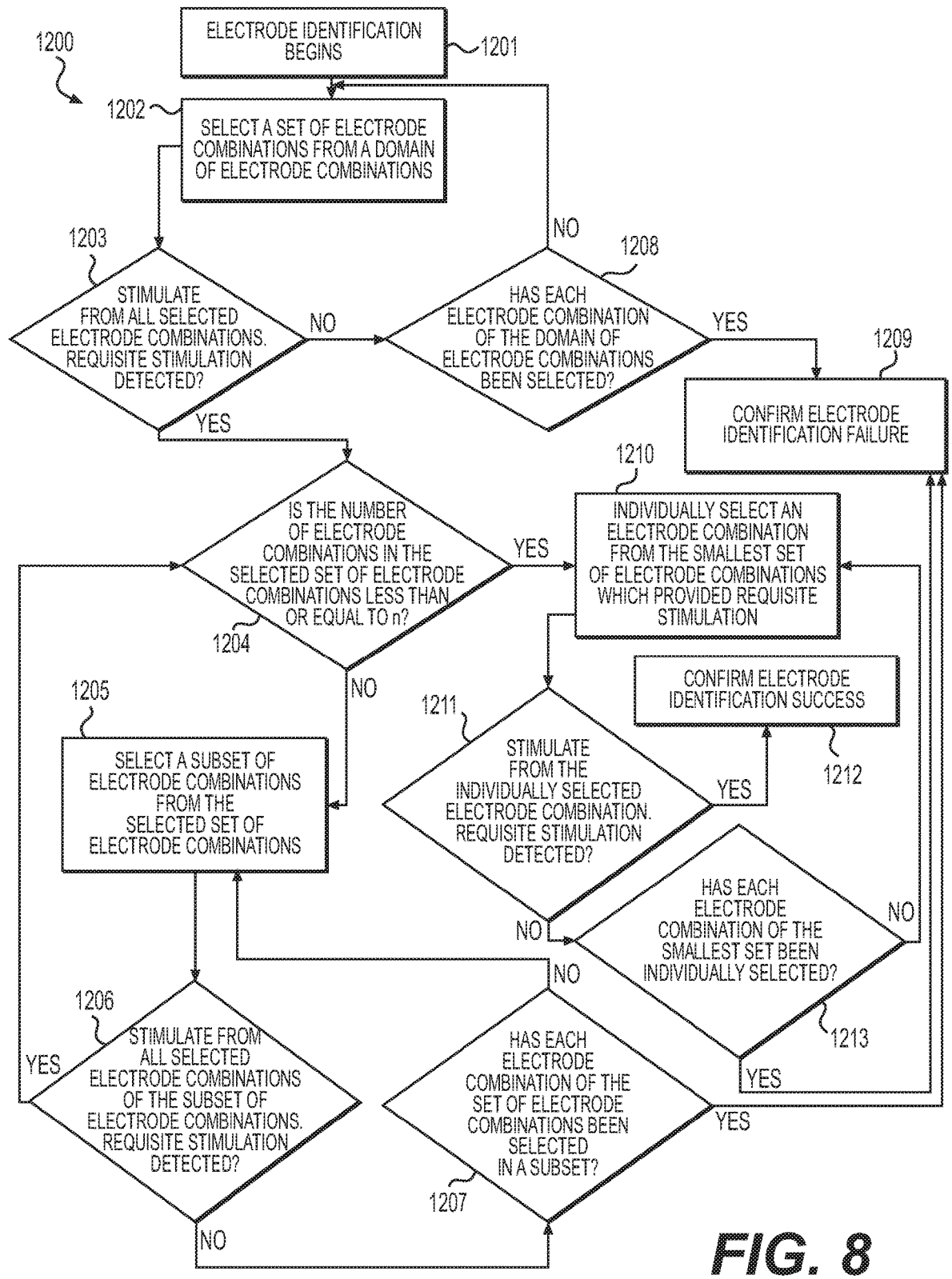
FIG. 8 is a flow chart of a method according to an embodiment of the present disclosure.

Referring to FIG. 8, one or more electrode identification processes (e.g, electrode identification process 1200) may be used to identify an electrode 530 or combination of electrodes 530 (e.g., an electrode combination), of the one or more stimulation arrays, that are best configured to deliver stimulation to one or more anatomical targets, are configured to deliver requisite stimulation at a lower charge than other electrodes 530 or electrode combinations, are closest to one or more anatomical targets, or a combination thereof. For example, a user (e.g., a healthcare professional) may, after placing one or more stimulation arrays on or in a patient and performing placement mode operations, perform an electrode identification process to identify which electrodes should be used for therapy mode operations.

In an electrode identification process (e.g., left electrode identification, right electrode identification, electrode identification process 1200), stimulation may be delivered to a series of electrodes 530 or combinations of electrodes 530 (e.g., electrode combinations) while physiological responses are observed (e.g., by a healthcare professional, a user, or system health monitor 160), to determine an optimal electrode combination for therapy mode. In some embodiments, the stimulation delivered during an electrode identification process may have a charge equal to the set coarse threshold.

FIG. 8 shows an exemplary flow of an electrode identification process of mapping mode of an LCU 100, according to one or more embodiments. In the exemplary mapping mode electrode identification process 1200 shown in FIG. 8, diamond regions (e.g., steps 1203, 1204, 1206, 1207, 1208, 1211, and 1213) represent decision points (e.g., a decision by the LCU 100 or a user) while rectangular regions (e.g., steps 1201, 1202, 1205, 1209, 1210, 1212) represent other inflection or action/step points of the process.

Still referring to FIG. 8, a mapping mode process, such as, for example, electrode identification process 1200, may begin based on an input from a user via user interface 120, for example, a mapping mode GUI 300 (step 1201). LCU 100 may then select a set of electrodes or a set of electrode combinations from a domain of electrodes or electrode combinations (step 1102). In one or more embodiments, a domain of electrodes may refer every electrode of a group of electrodes (e.g., a group of electrodes of one or more stimulation arrays). A domain of electrode combinations may refer to every possible electrode combination of a group of electrodes, every possible electrode combination out of available group of electrodes for bipolar electrical stimulation, every possible electrode combination out of available group of electrodes for tripolar electrical stimulation, or a listing of electrode combinations that are stored, programmed, or otherwise accessed by LCU 100 (e.g., a lookup table stored in a memory accessible by the LCU 100, such as, for example mass storage device 112). In some embodiments, an LCU 100 may have access to a list of likely electrode combinations. The list of most likely electrode combinations may include electrode combinations for monopolar, bipolar, tripolar, and other multipolarelectrical stimulation, such as, for example, combinations of electrodes that are proximate to each other and/or combinations of electrodes where the path of stimulation from a cathode to an anode is parallel to an anatomical target (e.g., a pair of electrodes that form a line parallel to a target nerve).

In some embodiments, selecting a set of electrode combinations from a domain of electrode combinations (step 1202) includes selecting half of the electrode combinations from the domain of electrode combinations (e.g., electrodes 530*a*, 530*b*, 530*c*, 530*g*, 530*h*, and 530*i*). In other embodiments, selecting a set of electrode combinations from a domain of electrode combinations includes selecting less than half of the electrode combinations from the domain of electrode combinations (e.g., electrodes 530*a*, 530*b*, 530*g*, and 530*h*). After a set of electrode combinations is selected, LCU 100 may stimulate from each electrode combination of the selected set of electrode combinations and may wait for input (e.g., from a sensor in communication with system health monitor 160 or via user interface 120) on whether requisite stimulation was detected (step 1203).

As described above, one or more indications may be made in anatomical indication window 330 that indicate stimulation is being delivered and/or indicate one or more targets of delivered stimulation. For example, the stimulation may target afferents of one or more lung-accessories (e.g., nerves or muscles associated with lung movement, such as, for example, a left phrenic nerve 520, a right phrenic nerve 522, a diaphragm, or a respiratory accessory muscle) and anatomical indication window 330 may include an indication that one or more lung-accessories is being stimulated (e.g., one or more lung or diaphragm pictograms may be indicated). One or more stimulation level indicators 342*a-f*, 342*a'-f'* of stimulation indication window 340, 340' may also be indicated as stimulation is delivered. In some embodiments, more stimulation level indicators 342a-f, 342a'-f are indicated as electrode combinations are tested. For example, in an initial stimulation of electrode identification process 1200, only stimulation level indicator 342a of stimulation indication window 340 may be indicated. Each time another set or subset of electrode combinations deliver stimulation, another stimulation level indicator 342a-f of stimulation indication window 340 (e.g., stimulation level indicator 342b) may be indicated.

Referring again to FIG. 8, after an LCU 100 stimulates from each electrode combination of the selected set of electrode combinations, it may receive input on whether the requisite stimulation of anatomical target occurred (step 1203). As noted above, requisite stimulation may refer to a stimulation sufficient to cause a desired physiological result. In some embodiments, requisite stimulation for mapping mode may include stimulation sufficient to cause contraction of a diaphragm or other lung-accessory. LCU 100 may receive input on whether the requisite stimulation of anatomical target occurred from one or more sensors in contact with the patient and in communication with system health monitor 160. In other embodiments, LCU 100 may receive input on whether the requisite stimulation of anatomical target occurred from a user (e.g., via a user interface 120, such as, for example, a mapping mode GUI 300). In some embodiments, a user may indicate requisite stimulation of an anatomical target occurred via one or more action buttons 360a-g (e.g., a "response" action button or a "next" action button). In some embodiments, a user may select a "retry" action button which may induce the LCU 100 to repeat the stimulation from each electrode combination of the selected set of electrode combinations.

If an LCU 100 receives input that a requisite stimulation of an anatomical target was not detected, LCU may then determine whether each electrode combination of the domain of electrode combinations had been selected at some point in the electrode identification process 1200 (step 1208). If each electrode combination of the domain of electrode combinations had been selected and delivered stimulation, but no requisite stimulation was detected, the LCU 100 may confirm electrode identification failure (step 1209). Confirmation of electrode identification failure may include displaying a notification to the user (e.g., a pop-up window or via notification box 310, anatomical indication window 330, or stimulation identification window 340) that electrode identification has failed. Such a notification may instruct a user to alter placement of one or more stimulation arrays relative to the patient, reperform one or more processes of placement mode or mapping mode (e.g., coarse threshold assessment process 1100).

If, at step 1208 of electrode identification process 1200, the LCU determines that not every electrode combination of the domain of electrode combinations had been selected, it may select a different set of electrode combinations of the domain of electrode combinations (step 1202). In embodiments where the first selected set of electrode combinations from the domain of electrode combinations was half of the domain of electrode combinations (e.g., electrodes 530a, 530b, 530c, 530g, 530h, and 530i), the second selected set of electrode combinations from the domain of electrode combinations may include the other half of the domain of electrode combinations (e.g., electrodes 530d, 530e, 530f, 530j, 530k, and 530l). According to one or more embodiments, after the initial selection of a set of electrode combinations from the domain of electrode combinations (e.g., electrodes 530a, 530b, 530g, and 530h), subsequent selections of sets of electrode combinations from the domain of electrode combinations may include electrode combinations that had not previously delivered stimulation as part of the electrode identification process 1200 (e.g., 530c, 530d, 530i, and 530j).

If, at step 1203 of electrode identification process 1200, LCU 100 receives input that a requisite stimulation of an anatomical target was detected, it may progress to narrowing the selected set of electrode combinations. For example, after determining a selected set of electrodes that deliver requisite stimulation (e.g., electrodes 530a, 530b, 530c, 530g, 530h, and 530i), LCU 100 may determine whether the number of electrode combinations of the set is less than or equal to n (step 1204), where n is an integer greater than or equal to 2, that may be set, programmed, or adjusted by an LCU 100 manufacturer, user, or healthcare professional. By way of non-limiting example, n may be set to 2, 3, 4, 5, 6, 7, 8, 9, 10, 11, 12, 13, 14, or 15. If the number of electrode combinations in the set is greater than n, LCU 100 may select a subset of electrode combinations from the selected set of electrode combinations (step 1205) (e.g., electrodes 530b, 530c, and 530i).

The efficiency and/or thoroughness of an electrode identification may be adjusted by the selection of n. For example, for relatively small values of n, an electrode identification process may be quicker than electrode identification processes with large values of n. Larger values of n may result in more time-intensive electrode identification processes, however, large n-value processes may be able to identify electrode combinations which are able to be used at lower fine thresholds than the quicker small n-value processes.

After LCU 100 selects a subset of electrode combinations from the selected set of electrode combinations (e.g., electrodes 530b, 530c, and 530i) (step 1205), LCU 100 may deliver stimulation from each electrode combination of the subset of electrode combinations (step 1206). After LCU 100 delivers stimulation from each electrode combination of the subset of electrode combinations, it may receive input on whether the requisite stimulation of anatomical target occurred (step 1206). If, at step 1206 of electrode identification process 1200, LCU 100 receives input that a requisite stimulation of an anatomical target was detected, it may progress to narrowing the selected subset of electrode combinations. For example, after determining a selected subset of electrodes deliver requisite stimulation (e.g., electrodes 530b, 530c, and 530i), LCU 100 may determine whether the number of electrode combinations of the subset is less than or equal to n (step 1204). If the number of electrode combinations in the subset that was found to deliver requisite stimulation is greater than or equal to n, LCU 100 may then continue to narrow down the subset, for example, by selecting a smaller subset of electrodes from the subset of electrodes found to deliver requisite stimulation (e.g., 530c and 530i) (step 1205).

If, at step 1206 of electrode identification process 1200, LCU 100 receives input that a requisite stimulation of an anatomical target was not detected, it may determine whether each electrode combination of the set of electrode combinations has been selected as part of a subset (step 1207). If each electrode of the set of electrode combinations has not been selected as part of a subset, then LCU 100 may select another subset of electrode combinations from the set of electrode combinations initially found to deliver requisite stimulation (e.g., electrodes 530a, 530g, and 530h) (step 1205). In some embodiments, the second selected subset may exclusively include electrode combinations not selected in the first subset. In other embodiments, the first subset and second subset may each have some of the same electrode combinations (e.g., a first subset of electrodes 530b, 530c, and 530i; and a second subset of electrodes 530b, 530h, and 530i). For example, the second subset may include half of the electrode combinations that were in the first subset (e.g., the distal most half or the proximal most half). According to one or more embodiments, LCU 100 may have access to a lookup table or other reference that informs LCU 100 which electrode combinations should be grouped together in subsets.

Returning to step 1207 of electrode identification process 1200, if each electrode of the set of electrode combinations has been selected as part of a subset, then LCU 100 may confirm failure of electrode identification (step 1209). As described above, confirmation of electrode identification failure may include displaying a notification to the user (e.g., a pop-up window or via notification box 310, anatomical indication window 330, or stimulation identification window 340) that electrode identification has failed. Such a notification may instruct a user to alter placement of one or more stimulation arrays relative to the patient, reperform one or more processes of placement mode or mapping mode (e.g., coarse threshold assessment process 1100).

If, at step 1204 of electrode identification process 1200, LCU 100 determines that the number of electrode combinations is less than or equal to n (e.g., if n=3, and a set of electrode combinations including electrodes 530b, 530c, and 530i was found to cause requisite stimulation), LCU 100 may progress to individually testing electrode combinations. For example, LCU 100 may individually select an electrode combination (e.g., electrode 530c) from the smallest set (e.g., the smallest subset) of electrode combinations which provided requisite stimulation (e.g., electrodes 530b, 530c, and 530i) (step 1210).

After individually selecting an electrode combination (e.g., electrode 530c) from the smallest set of electrode combinations that provided requisite stimulation e.g., electrodes 530b, 530c, and 530i), LCU 100 may deliver stimulation from the individually selected electrode combination (step 1211). After LCU 100 delivers stimulation from the individually selected electrode combinations, it may receive input on whether the requisite stimulation of anatomical target occurred (step 1211). If, at step 1211 of electrode identification process 1200, LCU 100 receives input that a requisite stimulation of an anatomical target was not detected, it may determine whether each electrode combination of the smallest set of electrode combinations (e.g., the set or subset including n or less electrode combinations) (e.g., electrodes 530b, 530c, and 530i) has been individually selected (step 1213).

If, at step 1211 of electrode identification process 1200, LCU 100 receives input that a requisite stimulation of an anatomical target was detected, it may confirm electrode identification (step 1212). Confirmation of electrode identification may include displaying a notification to the user (e.g., a pop-up window or via notification box 310, anatomical indication window 330, or stimulation indication window 340) that an electrode or electrode combination was identified. Further, confirming electrode identification may include saving information regarding the identified electrode or electrode combination for use in one or more other processes or modes.

In some embodiments, after completing an electrode identification process (e.g., left electrode identification, right electrode identification, electrode identification process 1200), an LCU 100 may begin a fine threshold assessment, a more precise determination of the threshold amount of charge that is appropriate or desired for stimulation. A user may initiate a fine threshold assessment via user interface 120 (e.g., via one or more action buttons 360a-g of a mapping mode GUI 300). Generally, a fine threshold assessment may include using a coarse threshold as a starting point, and by stimulating one or more anatomical targets with the one or more identified electrode combinations (e.g., one or more electrode combinations identified via one or more electrode combination identification processes 1200), assessing the lowest charge of stimulation that induces the desired physiological response.

Figure 9:
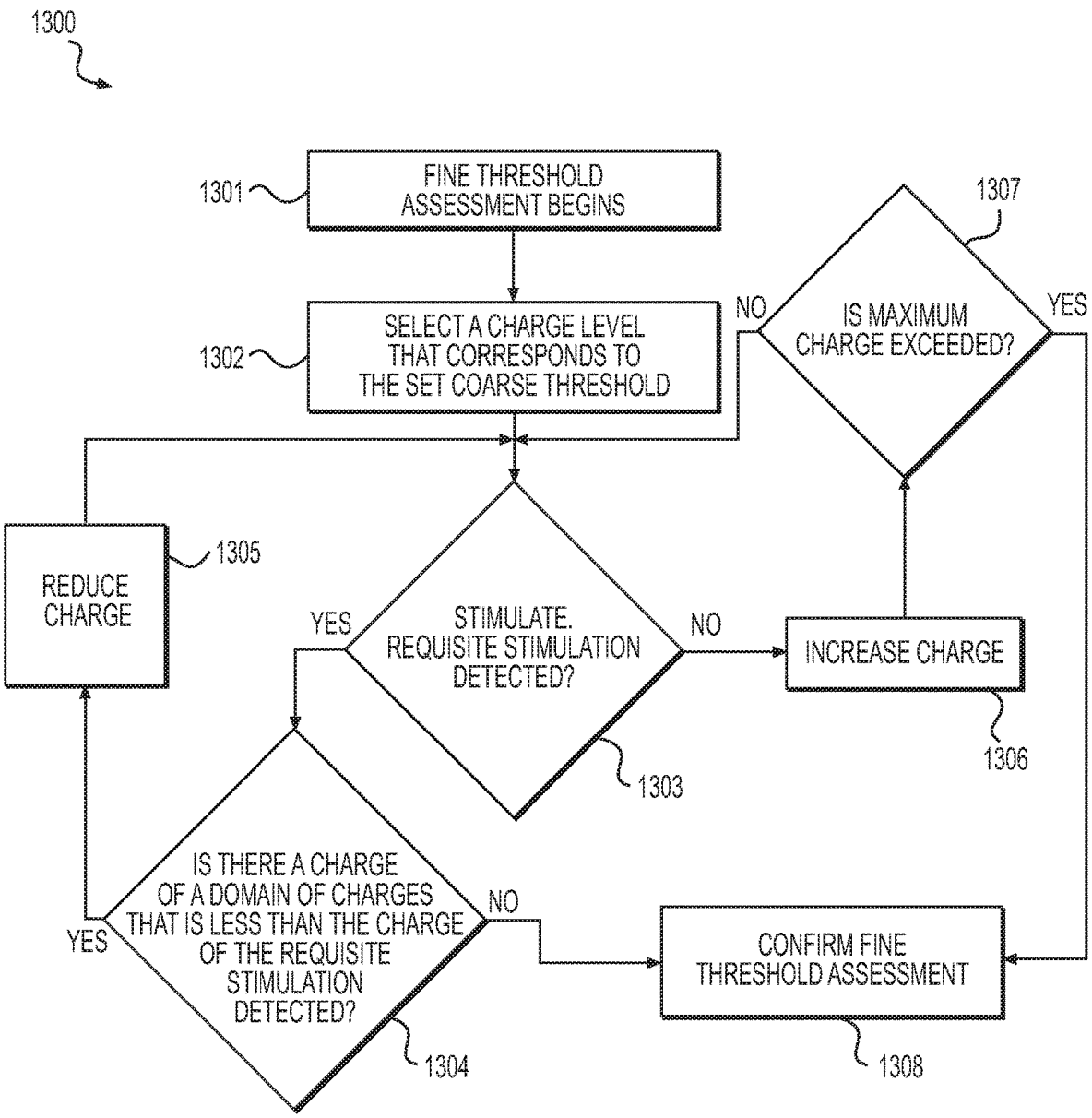
FIG. 9 is a flow chart of a method according to an embodiment of the present disclosure.

FIG. 9 shows an exemplary flow of a fine threshold assessment process of mapping mode of an LCU 100, according to one or more embodiments. In the exemplary mapping mode fine threshold assessment process 1300 shown in FIG. 9, diamond regions (e.g., steps 1303, 1304, and 1307) represent decision points (e.g., a decision by the LCU 100 or a user) while rectangular regions (e.g., steps 1301, 1302, 1104, 1105, 1107, and 1108) represent other inflection points or actions/steps of the method.

Still referring to FIG. 9, a mapping mode process, such as, for example, fine threshold assessment process 1300, may begin based on an input from a user via user interface 120, for example, a mapping mode GUI 300 (step 1301). LCU 100 may then select a charge level that corresponds to the set coarse threshold (step 1302). In some embodiments, the charge level that corresponds to the set coarse threshold is less than the coarse threshold. For example, if a coarse threshold is identified as 1.0 mA current with a 300 μs pulse width, the selected charge of step 1302 may have an amplitude less 1.0 mA and/or a pulse width shorter than 300 μs. An LCU 100 may have access to a lookup table, formula, or other reference that identifies charge levels by corresponding coarse thresholds.

After LCU 100 selects a charge level that corresponds to the set coarse threshold, it may deliver stimulation at that charge (e.g., via the electrode combination identified in an electrode identification process 1200) (step 1303). As described above, one or more indications may be made in anatomical indication window 330 that indicate stimulation is being delivered and/or indicate one or more targets of delivered stimulation. For example, the stimulation may target afferents of one or more lung-accessories (e.g., nerves or muscles associated with lung movement, such as, for example, a left phrenic nerve 520, a right phrenic nerve 522, a diaphragm, or a respiratory accessory muscle) and anatomical indication window 330 may include an indication that one or more lung-accessories is being stimulated (e.g., one or more lung or diaphragm pictograms may be indicated). One or more stimulation level indicators 342a-f, 342a'-f of stimulation indication window 340, 340' may also be indicated as stimulation is delivered. In some embodiments, more stimulation level indicators 342a-f, 342a'-f are indicated as the charge of the stimulation is adjusted. For example, in an initial stimulation, only stimulation level indicator 342a of stimulation indication window 340 may be indicated. Each time the charge of the stimulation is increased or decreased, another stimulation level indicator 342a-f of stimulation indication window 340 (e.g., stimulation level indicator 342b) may be indicated.

Referring still to FIG. 9, after an LCU 100 delivers stimulation, it may receive input on whether the requisite stimulation of anatomical target occurred (step 1303). As noted above, requisite stimulation may refer to a stimulation sufficient to cause a desired physiological result. In some embodiments, requisite stimulation for mapping mode may include stimulation sufficient to cause contraction of a diaphragm or other lung-accessory. LCU 100 may receive input on whether the requisite stimulation of anatomical target occurred from one or more sensors in contact with the patient and in communication with system health monitor 160. In other embodiments, LCU 100 may receive input on whether the requisite stimulation of anatomical target occurred from a user (e.g., via a user interface 120, such as, for example, a mapping mode GUI 300). In some embodiments, a user may indicate requisite stimulation of an anatomical target occurred via one or more action buttons 360*a-g* (e.g., a "response" action button or a "next" action button). In some embodiments, a user may select a "retry" action button 360*a-g* which may induce the LCU 100 to repeat the most recent stimulation at the current charge level (step 1303).

If an LCU 100 receives input that a requisite stimulation of an anatomical target was not detected, it may increase the charge of the stimulation (step 1306). Each increase or decrease in stimulation sweep charge may be at a consistent, constant interval, inconsistent, differing intervals, variable intervals, or arbitrary increments or decrements, and may occur as an increase or decrease in amplitude and/or an increase or decrease in pulse width. For example, each adjustment in stimulation charge may include an amplitude adjustment (either increase or decrease) of approximately 0.1 mA to approximately 5 mA, such as, for example, 0.1 mA, 0.2 mA, 0.3 mA, 0.4 mA, 0.5 mA, 1.0 mA, 1.5 mA, 2.0 mA, 2.5 mA, 3.0 mA, 3.5 mA, 4.0 mA, 4.5 mA, or 5.0 mA. In some embodiments, an adjustment in stimulation charge includes an increase or decrease in pulse width, such as, for example, 25 μs, 50 μs, 75 μs, 100 μs, 125 μs, 150 μs, 175 μs, 200 μs.

In a fine threshold assessment process 1300 of mapping mode, like other operations of LCU 100, the LCU 100 may end the current process (and/or prevent stimulation from being delivered) if a pre-determined maximum charge is exceeded. In some embodiments, the maximum charge for a fine threshold assessment process 1300 is the set coarse threshold (e.g., a coarse threshold identified in a coarse threshold assessment process 1100). After charge is increased (step 1306), an LCU 100 may determine whether the maximum charge is exceeded. If after increasing the charge of stimulation, the maximum charge is exceeded, fine threshold assessment may be confirmed and the fine threshold assessment process may end (step 1308).

If, at step 1303 of a fine threshold assessment process 1300, LCU 100 receives input that a requisite stimulation of an anatomical target was detected (step 1303), it may progress to determining whether there is a charge of a domain of charges that is less than charge that resulted in an indication of requisite stimulation (step 1304). In some embodiments, an LCU 100 may determine a domain of charges based on a coarse threshold assessment. For example, for each potential coarse threshold charge, the LCU 100 may be able to access, lookup, or otherwise recall a corresponding domain of potential fine threshold charges. In some embodiments, the maximum for a given domain of potential charges is less than or equal to the corresponding coarse threshold assessment.

If LCU 100 determines that there is a charge of the domain of charges that is less than the charge of requisite stimulation detected (step 1304), LCU 100 may reduce the charge of stimulation (step 1305). After the charge of stimulation is reduced, LCU 100 may stimulate at the reduced charge (e.g., via the electrode combination identified in an electrode identification process 1200) and receive input on whether requisite stimulation was detected (step 1303). If LCU 100 determines that there is not a charge of the domain of charges that is less than the charge that included requisite stimulation (step 1304), LCU 100 may confirm fine threshold assessment (step 1308).

Confirmation of a fine threshold assessment may include displaying a notification to the user (e.g., a pop-up window or via notification box 310, anatomical indication window 330, or stimulation indication window 340) that a fine threshold was identified. Further, confirming a fine threshold may include saving information regarding the fine threshold for use in one or more other processes or modes. In some embodiments, when a charge of stimulation exceeds the maximum charge, leading to confirmation of fine threshold assessment (step 1308), the fine threshold may be set at the maximum charge or a charge below the maximum charge that was found to be requisite stimulation.

As described above, one or more progress bars 345, 345' may track, display, or otherwise indicate progress or status of mapping mode, or one or more processes of mapping mode. For example, progress bar 345 may indicate the progress of mapping mode operations on the left side of patient's anatomy while progress bar 345' may indicate the progress of mapping mode operations on the right side of a patient's anatomy. In some embodiments, one or more segments of a progress bar 345 may change color, become filled-in, or otherwise be indicated each time a stimulation is delivered and/or an input is received by the LCU 100. In some embodiments, one or more segments of a progress bar 345 may change color, become filled-in, or otherwise be indicated only when a mapping mode process (e.g., a coarse threshold assessment process 1100, an electrode identification process 1200, or a fine threshold assessment process 1300) has been completed.

Therapy Mode

In therapy mode, one or more stimulation arrays may deliver stimulation to one or more therapeutic anatomical targets. In some embodiments, stimulation may be delivered via an electrode combination identified in an electrode identification process (e.g., electrode identification process 1200). Stimulation may be delivered at a charge equal to the set fine threshold (e.g., a fine threshold set as part of a fine threshold assessment process 1300). One or more other parameters of the stimulation (e.g., electrode combinations, pulse width, amplitude) may have been determined during one or more mapping mode processes and/or selected based on user input.

A user may adjust one or more parameters of stimulation via, for example, stimulation intensity adjustment keys 442*a,b*, 442*a'*, b' or stimulation parameters adjustment keys 446*a-d*, 446*a'-d'*. For example, a stimulation intensity may be set to 100% of the set fine threshold (as indicated in a stimulation intensity window 441'). As a patient is weaned off respiratory support, a user or healthcare professional may want to reduce the intensity of stimulation. Stimulation intensity adjustment keys 442*a,b*, 442*a'*, b' may be used to reduce the intensity of stimulation to a lower percentage of the set fine threshold In some embodiments, a user or healthcare professional may, via therapy mode GUI 400, prescribe, program, or set a number of therapeutic stimulations to be delivered over a set time interval. The exact parameters of this timed stimulation delivery may be monitored and/or adjusted via stimulation parameter windows 445*a-d*, stimulation parameter adjustment keys 446*a-d*, 446*a'-d'*, one or more action buttons 460*a-e*, delivered therapy status window 475, and/or scheduled therapy status window 470. For example, one or more stimulation parameter windows 445*a-d* (e.g., stimulation parameter window 445*a*), may display how many stimulations are to be delivered within the set time interval. In some embodiments, stimulation adjustment key 446*a* would allow a user to increase the number of stimulations (e.g., to more than 10) to be delivered within the set time interval and stimulation adjustment key 446*a*' would allow a user to decrease the number of stimulations (e.g., to fewer than 10) to be delivered within the set time interval. By way of another example, one or more stimulation parameter windows 445*a-d* (e.g., stimulation parameter window 445*d*) may display how the time interval (e.g., in second, minutes, or hours) over which the number of stimulations (e.g., shown in stimulation window 445*a*) will be delivered. In this example, stimulation adjustment key 446*d*, when selected, would increase the time interval, and stimulation adjustment key 446*d*', when selected, would decrease the time interval.

In addition to timing and delivery of timed stimulation delivery, stimulation parameter windows 445*a-d* may display one or more other parameters of stimulation, such as, for example, stimulation amplitude, stimulation pulse width, stimulation charge, stimulation frequency. The stimulation adjustment keys 446*a-d*, 446*a*'-*d*' may allow a user to adjust the one or more stimulation parameters displayed in stimulation parameter windows 445*a-d*. For example stimulation adjustment keys 446*a* and 446*a*' may adjust the stimulation parameter shown in stimulation parameter window 445*a*, stimulation adjustment keys 446*b* and 446*b*' may adjust the stimulation parameter shown in stimulation parameter window 445*b*, stimulation adjustment keys 446*c* and 446*c*' may adjust the stimulation parameter shown in stimulation parameter window 445*c*, and stimulation adjustment keys 446*d* and 446*d*' may adjust the stimulation parameter shown in stimulation parameter window 445*d*.

Further technical modes of the LCU may include data retention and management, touchscreen calibration, date and time adjustment, software and FPGA version information tracking, internal communication logging, cloud data communication/access/storage/sharing, and WiFi/RFID/etc. interface. In some embodiments, these technical modes are not accessible by a general permissions user. According to one or more embodiments, these technical modes may be accessed via user interface 120.

What is claimed is:

1. A system for stimulating body tissue, the system comprising:
    at least one sensor configured to be affixed to, or inserted in, a body to measure airway pressure, airway flowrate, transpulmonary pressure, tidal volume, lung gas distribution, transdiaphragmatic pressure, or a combination thereof;
    a stimulation array;
    a user interface; and
    a control unit including a processor and a non-transitory computer readable medium storing instructions that, when executed by the processor, causes the processor to identify an electrode combination of the stimulation array;
    wherein identifying an electrode combination of the stimulation array includes receiving an input via the user interface, the at least one sensor, or both, and the input relates to whether a requisite stimulation was detected.

2. The system of claim 1, wherein the stimulation array is supported by an intravascular catheter.

3. The system of claim 1, wherein identifying an electrode combination of the stimulation array further includes:
    selecting a first set of electrode combinations from a domain of electrode combinations;
    stimulating from all electrode combinations of the first set of electrode combinations; and
    relating a corresponding input to each electrode combination of the first set of electrode combinations.

4. The system of claim 3, wherein identifying an electrode combination of the stimulation array further includes:
    selecting a second set of electrode combinations, wherein the second set of electrode combinations is a subset of the first set of electrode combinations, and each electrode combination of the second set of electrode combinations corresponds to one input that the requisite stimulation was detected.

5. The system of claim 4, wherein identifying an electrode combination of the stimulation array further includes:
    individually selecting an electrode combination from the second set of electrode combinations;
    stimulating from the individually selected electrode combination; and
    relating a second corresponding input to the individually selected electrode combination.

6. The system of claim 1, wherein the stimulation array includes at least two groups of electrodes; and
    identifying an electrode combination includes identifying an electrode combination for each group of electrodes; and
    the instructions stored in the non-transitory computer readable medium further cause the processor to determine a threshold charge for each group of electrodes.

7. The system of claim 1, wherein the user interface comprises:
    an anatomical indication window;
    at least two action buttons; and
    one or more stimulation level indication windows; and
    wherein the instructions stored in the non-transitory computer readable medium, when executed by the processor, cause the processor to assess a position of the stimulation array, and determine a threshold charge for use in stimulating the body tissue;
    wherein receiving an input via the user interface, the at least one sensor, or both, includes:
    prompting a user, via the user interface, the one or more sensors, or both, to provide feedback on whether requisite stimulation was detected; and
    receiving input on whether the requisite stimulation was detected via the user interface, the one or more sensors, or both.

8. The system of claim 7, wherein identifying the electrode combination of the stimulation array further includes:
    selecting a first set of electrode combinations from a domain of electrode combinations;
    stimulating from all electrode combinations of the first set of electrode combinations;
    relating a corresponding input to each electrode combination of the first set of electrode combinations;
    based on the corresponding inputs, selecting a second set of electrode combinations, wherein the second set of electrode combinations is a subset of the first set of electrode combinations;
    stimulating from all electrode combinations of the second set of electrode combinations;
    relating a second corresponding input to each electrode combination of the second set of electrode combinations; and
    based on the second corresponding inputs, selecting the electrode combination.

9. The system of claim 8, wherein the stimulation array includes at least two groups of electrodes;
   identifying the electrode combination includes identifying an electrode combination for each group of electrodes; and
   determining the threshold charge includes identifying a threshold charge for each group of electrodes.

10. The system of claim 7, wherein the instructions stored in the non-transitory computer readable medium cause the processor, when determining a threshold charge, to determine a coarse threshold charge and a fine threshold charge.

11. The system of claim 10, wherein the instructions stored in the non-transitory computer readable medium cause the processor, when determining a coarse threshold charge to:
   perform an electrode sweep at a first charge;
   receive a first input on whether a requisite stimulation was detected;
   if the first input indicates requisite stimulation was detected, set the coarse threshold charge at a charge of the most recent electrode sweep, ending the determination of the coarse threshold charge; or
   if the first input indicates the requisite stimulation was not detected, perform an electrode sweep at a second charge greater than the first charge;
   receive a second input on whether the requisite stimulation was detected; and
   if the second input indicates the requisite stimulation was detected, set the coarse threshold charge at a charge of the most recent electrode sweep; or
   if the second input indicates the requisite stimulation was not detected, perform an electrode sweep at a third charge greater than the second charge.

12. The system of claim 11, wherein while the electrode sweep is performed at the first charge, a first portion of the stimulation level indication window is indicated; and
   while the electrode sweep is performed at the second charge, the first portion and a second portion of the stimulation level indication window are indicated.

13. The system of claim 10, wherein the instructions stored in the non-transitory computer readable medium cause the processor, when determining a fine threshold charge to:
   select a charge level that corresponds to a determined coarse threshold;
   determine a domain of charges based on the determined coarse threshold;
   deliver stimulation at the charge level corresponding to the determined coarse threshold;
   receive a first input on whether the requisite stimulation was detected; and
   if the first input indicates the requisite stimulation was detected, deliver stimulation at a charge level of the domain of charges that is less than the determined coarse threshold; or
   if the first input indicates the requisite stimulation was not detected, deliver stimulation at a charge level of the domain of charges that is greater than the determined coarse threshold.

14. The system of claim 7, wherein a portion of the anatomical indication window is indicated while stimulation is delivered, and wherein the portion corresponds to a tissue receiving the delivered stimulation.

15. The system of claim 7, wherein instructions executed by the processor, cause the processor to, after the threshold charge is determined:
   prompt the user, via the user interface, to select a charge, out of a set of charges, for stimulating tissue, wherein the set of charges is determined by the processor based on the determined threshold charge.

16. A system for stimulating body tissue, the system comprising:
   at least one sensor configured to be affixed to, or inserted in, a body to measure one or more physiological parameters of the body;
   a stimulation array;
   a user interface; and
   a control unit including a processor and a non-transitory computer readable medium storing instructions that, when executed by the processor, causes the processor to identify an electrode combination of the stimulation array;
   wherein identifying an electrode combination of the stimulation array includes:
      selecting a first set of electrode combinations;
      stimulating from all electrode combinations of the first set of electrode combinations;
      for each stimulation from an electrode combination of the first set of electrode combinations, receiving an input via the user interface, the at least one sensor, or both, and the input relates to whether a requisite stimulation was detected;
      relating a corresponding input to each electrode combination of the first set of electrode combinations; and
      selecting a second set of electrode combinations, wherein the second set of electrode combinations is a subset of the first set of electrode combinations, and each electrode combination of the second set of electrode combinations corresponds to one input that the requisite stimulation was detected.

17. The system of claim 16, wherein the instructions stored in the non-transitory computer readable medium, when executed by the processor, cause the processor to:
   determine a threshold charge for use in stimulating the body tissue; and
   after the threshold charge is determined, prompt the user, via the user interface, to select a charge, out of a set of charges, for stimulating tissue, wherein the set of charges is determined by the processor based on the determined threshold charge.

18. A system for stimulating body tissue, the system comprising:
   at least one sensor configured to be affixed to, or inserted in, a body to measure one or more physiological parameters of the body;
   a stimulation array;
   a user interface comprising:
      an anatomical indication window;
      one or more stimulation level indication windows; and
   a control unit including a processor and a non-transitory computer readable medium storing instructions that, when executed by the processor, causes the processor to identify an electrode combination of the stimulation array;
   wherein identifying an electrode combination of the stimulation array includes:
      prompting a user, via the user interface, to provide feedback on whether a requisite stimulation was detected; and
      receiving an input on whether the requisite stimulation was detected via the user interface.

19. The system of claim 18, wherein a portion of the anatomical indication window is indicated while stimulation is delivered, and wherein the portion corresponds to a tissue receiving the delivered stimulation.

20. The system of claim 18, wherein the instructions stored in the non-transitory computer readable medium, when executed by the processor, cause the processor to determine a coarse threshold charge and a fine threshold charge.

\* \* \* \* \*